US012023341B2

(12) United States Patent
Bierbach et al.

(10) Patent No.: US 12,023,341 B2
(45) Date of Patent: Jul. 2, 2024

(54) PLATINUM-ACRIDINE COMPOUNDS AND METHODS OF TREATING CANCERS

(71) Applicant: Wake Forest University, Winston-Salem, NC (US)

(72) Inventors: Ulrich Bierbach, Winston-Salem, NC (US); Shenjie Zhang, Winston-Salem, NC (US); Xiyuan Yao, Winston-Salem, NC (US); Ikeer Y. Mancera-Ortiz, High Point, NC (US); Noah H. Watkins, Lewisville, NC (US)

(73) Assignee: Wake Forest University, Winston-Salem, NC (US)

( * ) Notice: Subject to any disclaimer, the term of this patent is extended or adjusted under 35 U.S.C. 154(b) by 33 days.

(21) Appl. No.: 17/235,382

(22) Filed: Apr. 20, 2021

(65) Prior Publication Data

US 2021/0330679 A1 Oct. 28, 2021

Related U.S. Application Data

(60) Provisional application No. 63/012,596, filed on Apr. 20, 2020.

(51) Int. Cl.

| | |
|---|---|
| ***C07F 15/00*** | (2006.01) |
| ***A61K 31/165*** | (2006.01) |
| ***A61K 31/19*** | (2006.01) |
| ***A61K 31/4406*** | (2006.01) |
| ***A61K 31/444*** | (2006.01) |
| ***A61K 31/455*** | (2006.01) |
| ***A61K 31/496*** | (2006.01) |
| ***A61K 31/519*** | (2006.01) |
| ***A61K 31/5377*** | (2006.01) |
| ***A61K 31/555*** | (2006.01) |
| ***A61K 31/706*** | (2006.01) |
| ***A61K 38/15*** | (2006.01) |
| ***A61P 35/00*** | (2006.01) |

(52) U.S. Cl.

CPC .......... *A61K 31/555* (2013.01); *A61K 31/165* (2013.01); *A61K 31/19* (2013.01); *A61K 31/4406* (2013.01); *A61K 31/444* (2013.01); *A61K 31/455* (2013.01); *A61K 31/496* (2013.01); *A61K 31/519* (2013.01); *A61K 31/5377* (2013.01); *A61K 31/706* (2013.01); *A61K 38/15* (2013.01); *A61P 35/00* (2018.01); *C07F 15/0093* (2013.01)

(58) Field of Classification Search

CPC . C07F 15/0093; A61K 31/165; A61K 31/444; A61K 31/519

See application file for complete search history.

(56) References Cited

U.S. PATENT DOCUMENTS

| | | | | |
|---|---|---|---|---|
| 6,001,872 | A | 12/1999 | Farrell et al. | |
| 8,906,896 | B2 * | 12/2014 | Bierbach | A61K 31/47 546/10 |
| 9,090,640 | B2 * | 7/2015 | Bierbach | C07F 15/0093 |
| 9,765,103 | B2 * | 9/2017 | Bierbach | A61P 35/00 |
| 10,377,784 | B2 | 8/2019 | Bierbach et al. | |
| 10,925,831 | B2 | 2/2021 | Bierbach et al. | |
| 11,591,357 | B2 * | 2/2023 | Bierbach | C07F 15/0093 |
| 2017/0081293 | A1 | 3/2017 | Bierbach et al. | |
| 2017/0210772 | A1 | 7/2017 | Bierbach et al. | |
| 2019/0290685 | A1 | 9/2019 | Bierbach et al. | |

FOREIGN PATENT DOCUMENTS

| | | | | |
|---|---|---|---|---|
| WO | 99/64019 | A1 | 12/1999 | |
| WO | 2013/033430 | A1 | 3/2013 | |
| WO | 2019/046278 | * | 3/2019 | A01N 43/62 |
| WO | 2019/046278 | A1 | 3/2019 | |

OTHER PUBLICATIONS

Baruah H. et al. "Platinum-intercalator conjugates: from DNA-targeted cisplatin derivatives to adenine binding complexes as potential modulators of gene regulation", Curr Top Med Chem. 2004;4(15):1537-49, 13 pages.

Ding S. et al. "Using fluorescent post-labeling to probe the subcellular localization of DNA-targeted platinum anticancer agents," Angew Chem Int Ed Engl. Mar. 18, 2013;52(12):3350-4, 8 pages.

Graham L.A. et al. "Synthesis, aqueous reactivity, and biological evaluation of carboxylic acid ester-functionalized platinum-acridine hybrid anticancer agents," J Med Chem. Sep. 13, 2012;55(17):7817-27, 26 pages.

Qiao X et al. "Investigating the cellular fate of a DNA-targeted platinum-based anticancer agent by orthogonal double-click chemistry," J Biol Inorg Chem. Mar. 2014;19(3):415-426, 18 pages.

* cited by examiner

*Primary Examiner* — Pancham Bakshi

(74) *Attorney, Agent, or Firm* — Fox Rothschild LLP

(57) ABSTRACT

Platinum-acridines and analogs thereof as cytotoxic agents for cancer treatment. Also provided methods of using hMATE1 (SLC47A1) as a biomarker to identify tumors that are likely to respond to the agents, and epigenetically sensitizing tumor tissue to anticancer drugs targeting this membrane transporter.

25 Claims, 3 Drawing Sheets

Specification includes a Sequence Listing.

P8A1

Azide-modified platinum(IV) prodrug example 1:

Y = hydroxide
Y' = 2-azidoacetate

Azide-modified platinum(IV) prodrug example 2:

Y = acetate
Y' = 2-azidoacetate

DBCO-maleimide extended payload, example 1

DBCO-PEG-maleimide extended payload, example 2

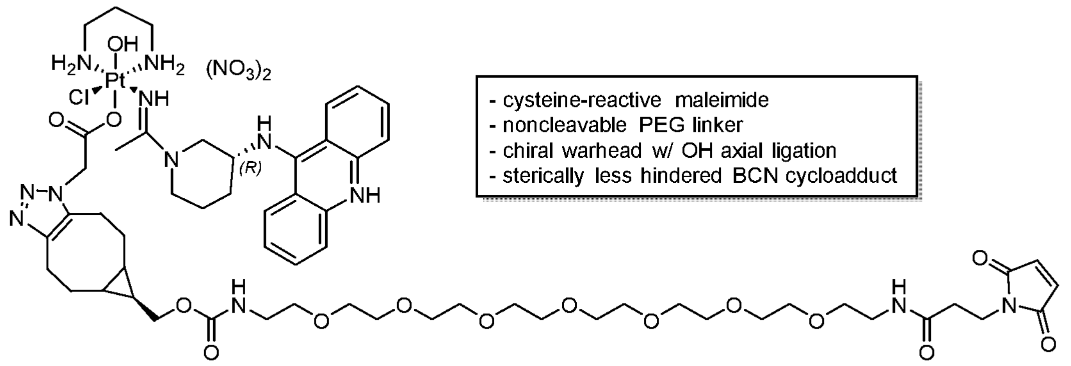

- cysteine-reactive maleimide
- noncleavable PEG linker
- chiral warhead w/ OH axial ligation
- sterically less hindered BCN cycloadduct + isomers

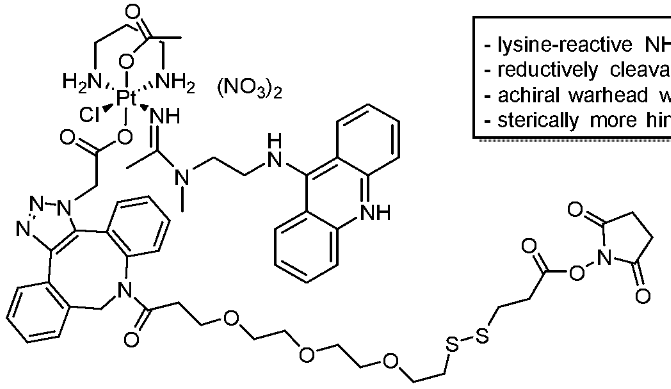

- lysine-reactive NHS ester
- reductively cleavable PEG-disulfide linker
- achiral warhead w/ OAc axial ligation
- sterically more hindered DBCO cycloadduct + isomers

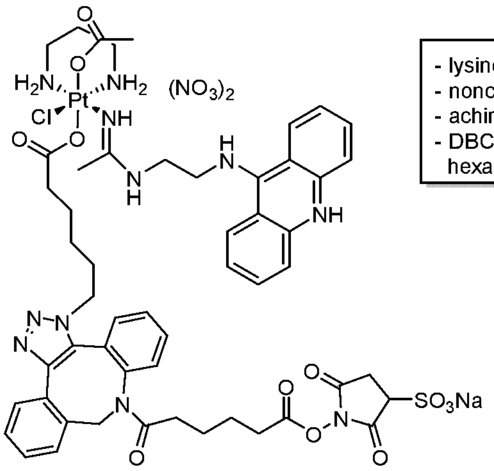

- lysine-reactive sulfo-NHS ester w/ enhanced water solubility
- noncleavable C6 alkyl linker
- achiral warhead w/ OAc axial ligation
- DBCO is click-conjugated with azide in an extended-chain 6-azido hexanoato axial ligand + isomers

Figure 2 i. 1 eq. of 2-azidoacetic acid NHS ester; DMF, r.t., dark, 2 h; precipitation with diethyl ether, exhaustive washing with diethylether to remove NHS; Yield: 90%, characterized by $^1$H NMR and LC-ESI-MS (water/MeOH/0.1% formic acid), analytical purity: 95% ii. 100-fold excess acetic anhydride in DMF, r.t., dark, 16 h, precipitation with diethyl ether; exhaustive washing with diethylether to remove acetic anhydride; Yield: 90%, characerized by $^1$H NMR and LC-ESI-MS (water/MeOH/0.1% formic acid), analytical purity: 94% iii. 1 eq. of DBCO(DIBAC)-maleimide, DMF, r.t. dark, 16 h, precipitation, crude product has 94% purity (by LC-ESI-MS). Yield: 92%; additional purification by preparative-scale reverse-phase chromatography

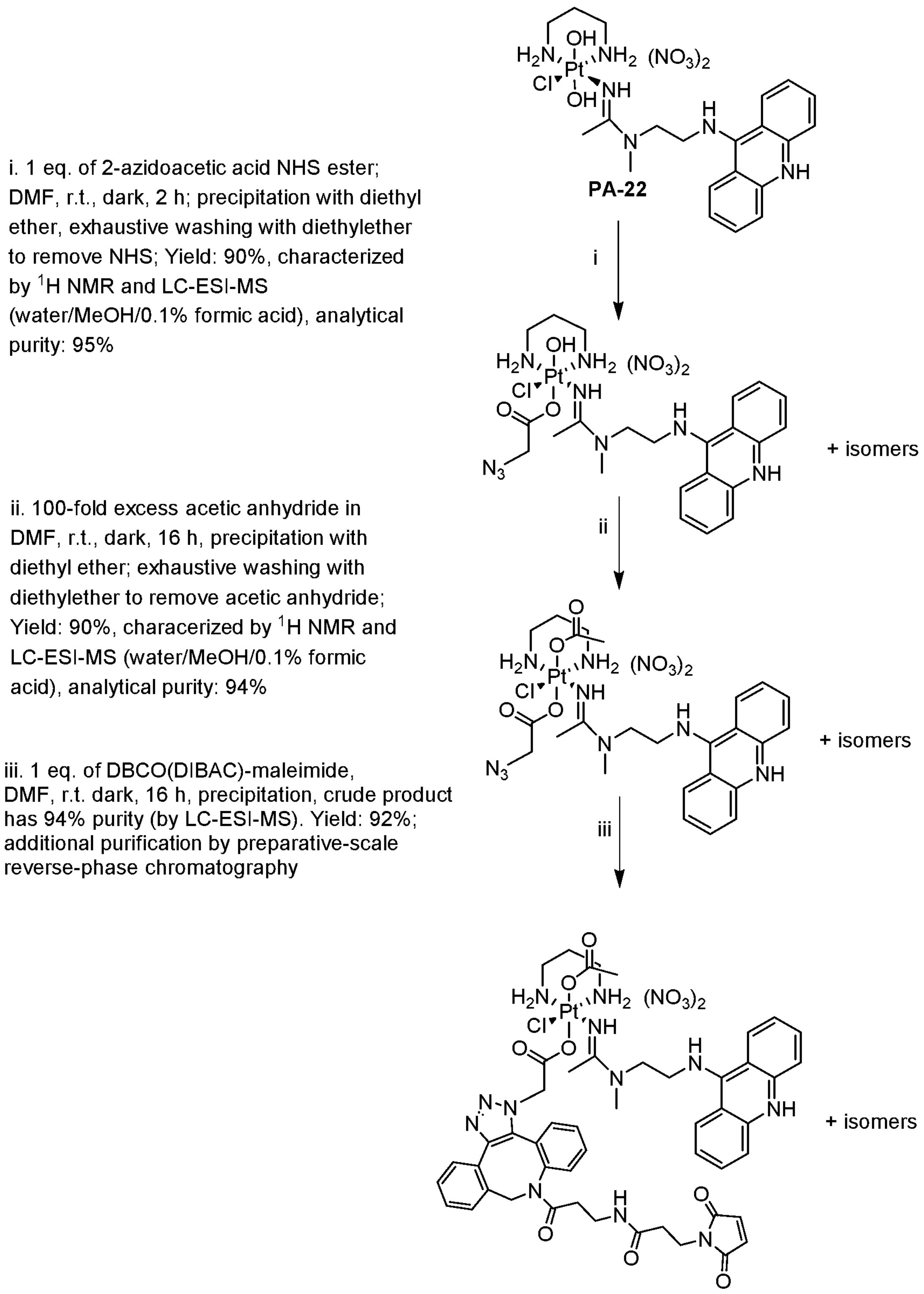

Figure 3

PLATINUM-ACRIDINE COMPOUNDS AND METHODS OF TREATING CANCERS

CROSS REFERENCE TO RELATED APPLICATIONS

This application claims the benefit of U.S. Provisional Patent Application No. 63/012,596 filed on Apr. 20, 2020, the contents of which are hereby incorporated by reference herein.

FIELD OF THE INVENTION

This patent document discloses functionalized forms of highly cytotoxic platinum-acridine anticancer agents and methods of epigenetically sensitizing tumor tissue to the anticancer agents.

BACKGROUND OF THE INVENTION

Aggressive, metastatic tumors, such as non-small-cell lung cancer (NSCLC), require innovative treatment options that result in a longer-lasting response and reduced mortality rates, with multifactorial tumor resistance remaining the most common cause of therapeutic failure and disease progression. Classical chemotherapy, most notably platinum-based regimens, continues to be a standard of care for NSCLC and other advanced solid tumors despite the promise of the newer molecularly targeted therapies and immuno-oncology (IO) drugs.

Platinum anticancer agents such as cisplatin, carboplatin and oxaliplatin presently in clinical use are among the most widely used anticancer agents in the world. In particular, these platinum drugs have been known to exhibit superior antitumor activities against genitourinal cancers such as testicular, ovarian, and bladder cancers as well as colorectal cancer.

However, like other low-molecular-weight anticancer agents such as paclitaxel, doxorubicin, etc., platinum anticancer agents administered systemically attack not only tumor cells and tissues but also normal cells and tissues equally without tumor selectivity, which cause severe toxicities such as nephrotoxicity, neurotoxicity, etc. In addition, their acquired cross-resistance and low water-solubility seriously limit their utility for cancer treatment.

Given these limitations, there is a continued interest in new pipelines of mechanistically unique agents and synergistic treatment strategies, which includes novel pharmacophores that overcome the drawbacks of current platinum drugs and other chemotherapies.

SUMMARY OF THE INVENTION

Platinum-acridines and analogs disclosed in this patent document are advantageous over classical platinum drugs in terms of the DNA damage and the cellular response they cause. In addition, using hMATE1 as a pan-cancer biomarker to identify tumors that are likely to respond to these compounds, a personalized treatment approach can be developed. Further, the chemosensitizing properties of hMATE1 in combination with its epigenetic regulation present a new strategy for tackling intractable tumors with platinum-acridines and other oncology drugs targeting this membrane transporter.

An aspect of this patent document provides a compound represented by Formula I,

Formula I

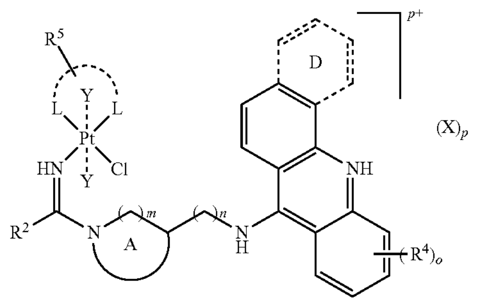

wherein, each L independently represents monodentate $NH_3$ or an amine ligand wherein the nitrogen coordinates to Pt, further wherein the two amine ligands optionally link up to form a diamine ligand (chelate);

X represents nitrate or halide;

Each Y independently represents a ligand selected from the group consisting of halide, hydroxide, pseudohalide, acetate, and

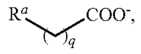

wherein q is an integer from 1 to 6 inclusive, wherein $R^a$ represents (a) $C_{2-4}$alkyl, OH, SH, $NH_2$, COOH, amino acids, CN, an alkyne-containing group, $N_3$, $(OCH_2CH_2)_rOC_{1-4}$alkyl, $(NHCH_2CH_2)_rNHC_{1-4}$alkyl, wherein r is an integer from 1 to 4 inclusive;

(b) extended linker-conjugate L-E, wherein E is terminal functional group capable of forming a new bond with another nucleophile or electrophile; non-limiting examples of E include amino acid-reactive moieties such as maleimide, self-stabilizing maleimide, dibromomaleimide, next generation maleimides (NGM), 2'-pyridyldithio variant, SMCC, aromatic or vinyl sulfone, acrylate, haloacetyl, N-hydroxysuccinimidyl esters (NHS, sulfo-NHS), anhydrides, fluorophenyl esters, and activated lactams;

or (c) extended linker-conjugate L-M, wherein M is a targeting moiety, such as a peptide, protein, synthetic polymer, aptamer, or nanoparticle wherein L in (b) and (c) is a linker comprising a linkage formed from azide and alkyne;

o is 0, 1, 2 or 3;

p is 1 or 2;

m is 0, 1, 2 or 3;

n is 0, 1, 2 or 3;

D is an optional aromatic ring;

$R^1$, $R^2$ and $R^3$ each independently represents a $C_{1-10}$ alkyl, wherein one or more carbons of the $C_{1-10}$ alkyl is optionally (a) replaced with a moiety selected from the group consisting of amino, oxygen, sulfur, amide, ester, carbamate, sulfonamide, sulfonyl, carbonate, ketone, and disulfide; or (b) substituted with a moiety selected from the group consisting of hydroxy, imino, oxo, cyano, $C_{1-10}$ alkoxy, $C_{1-10}$ alkylthio, $C_{1-6}$ alkylsulfonyl, and di-$C_{1-10}$ alkylamine;

$R^4$ is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, or (mono-, di-, or trihalogeno)methyl;

$R^5$ represents an optional substituent of L and is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, (mono-, di-, or trihalogeno) methyl, or $C_{1-10}$ alkoxy;

provided that the compound meets one of (i), (ii) and (iii):

(i) $R^1$ and $R^3$ link up to form a 4 to 8 membered ring;

(ii) $R^2$ and $R^3$ link up to form a 5 to 8 membered ring;

(iii) at least one of the two Ys is present and is selected from the group consisting of OH, chloride, acetate and

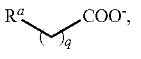

wherein q is an integer from 1 to 6 inclusive, $R^a$ represents $C_{1-4}$alkyl, OH, SH, $NH_2$, COOH, CN, an alkyne-containing group, $N_3$, $(OCH_2CH_2)_rOC_{1-4}$alkyl or $(NHCH_2CH_2)_r$-$NHC_{1-4}$alkyl, wherein r is an integer from 1 to 4 inclusive;

(iv) at least one of the two Ys is present and is L-E, and (v) at least one of the two Ys is present and is L-M;

provided the compound is not

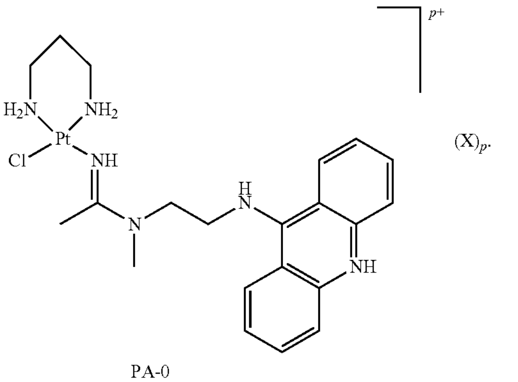

PA-0

In some embodiments, $R^1$ and $R^3$ link up to form a 4 to 8 membered ring as represented by Formula II.

Formula II

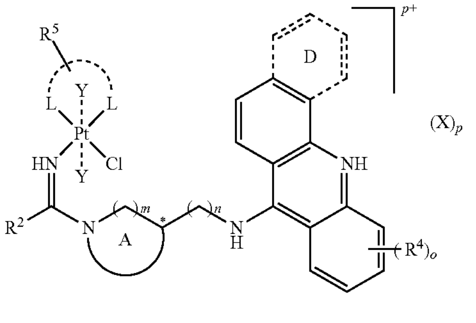

In some embodiments, $R^2$ and $R^3$ link up to form a 5 to 8 membered ring and the compound is represented by Formula III.

Formula III

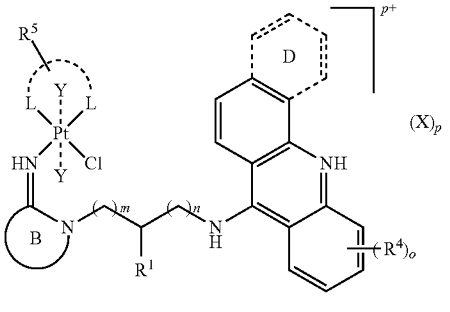

In some embodiments, the compound is

Formula III-A

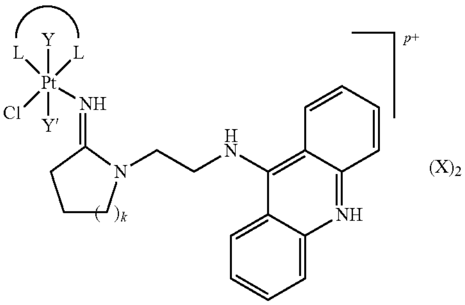

or

Formula III-B

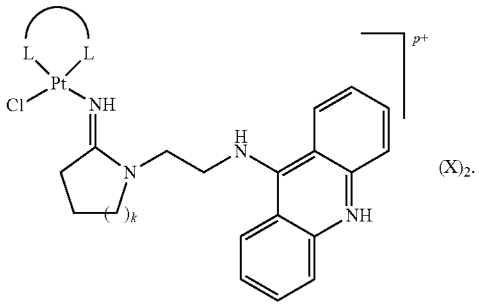

Another aspect provides a pharmaceutical composition of the compound of Formula I. Also provided is a method of treating cancer comprising administering to a subject in need thereof a therapeutically effective amount of the compound.

Another aspect provides a method of preparing the compound of Formula I-A or Formula I-B from the corresponding intermediate I-C where Y is absent by treating the intermediate with suitable oxidizing agent to convert Pt(II) to Pt(IV). Further reactions to replace or modify ligand Y can be performed if necessary.

Another aspect of the patent document provides a method of treating a cancer in a subject, comprising:

(a) obtaining a biological sample from the subject;

(b) detecting expression of MATE1 in the biological sample;

(c) administer to the subject of a therapeutically effective amount of a compound of Formula I', wherein, Formula I'

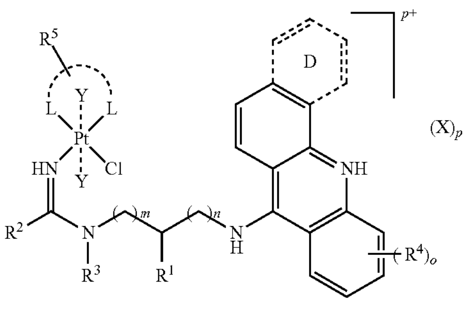

each L independently represents monodentate $NH_3$ or an amine ligand wherein the nitrogen coordinates to Pt, further wherein the two amine ligands optionally link up to form a diamine ligand (chelate);

X represents nitrate or halide;

Each Y independently represents a ligand selected from the group consisting of halide, hydroxide, pseudohalide, acetate, and

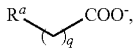

wherein q is an integer from 1 to 6 inclusive, $R^a$ represents OH, SH, $NH_2$, COOH, amino acids, CN, an alkyne-containing group, $N_3$, $(OCH_2CH_2)_rOC_{1-4}$alkyl or $(NHCH_2CH_2)_rNHC_{1-4}$alkyl, wherein r is an integer from 1 to 4 inclusive;

is 0, 1, 2 or 3;

p is 1 or 2;

m is 0, 1, 2 or 3;

n is 0, 1, 2 or 3;

D is an optional aromatic ring;

$R^1$, $R^2$ and $R^3$ each independently represents a $C_{1-10}$ alkyl, wherein one or more carbons of the $C_{1-10}$ alkyl is optionally (a) replaced with a moiety selected from the group consisting of amino, oxygen, sulfur, amide, ester, carbamate, sulfonamide, sulfonyl, carbonate, ketone, and disulfide; or (b) substituted with a moiety selected from the group consisting of hydroxy, imino, oxo, cyano, $C_{1-10}$ alkoxy, $C_{1-10}$ alkylthio, $C_{1-6}$ alkylsulfonyl, and di-$C_{1-10}$ alkylamine;

$R^4$ is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, or (mono-, di-, or trihalogeno)methyl;

$R^5$ represents an optional substituent of L and is selected from the group consisting of halogen, cyano, nitro, $C_{1-10}$ alkylthio, $C_{2-10}$ alkenyl, $C_{2-10}$alkynyl, $C_{1-10}$ alkoxy, $C_{1-10}$ dialkylamino, $C_{1-10}$ alkyl, (mono-, di-, or trihalogeno)methyl, or $C_{1-10}$ alkoxy.

Another aspect of the patent document provides a kit for treating a cancer, comprising the compound of Formula I' and an instruction manual for detecting the expression of MATE1.

BRIEF DESCRIPTION OF THE DRAWINGS

FIG. 2 shows exemplary compounds of Formula I.

FIG. 3 shows an exemplary synthesis of compounds with a linker derived from click chemistry.

DETAILED DESCRIPTION

Figure 1:
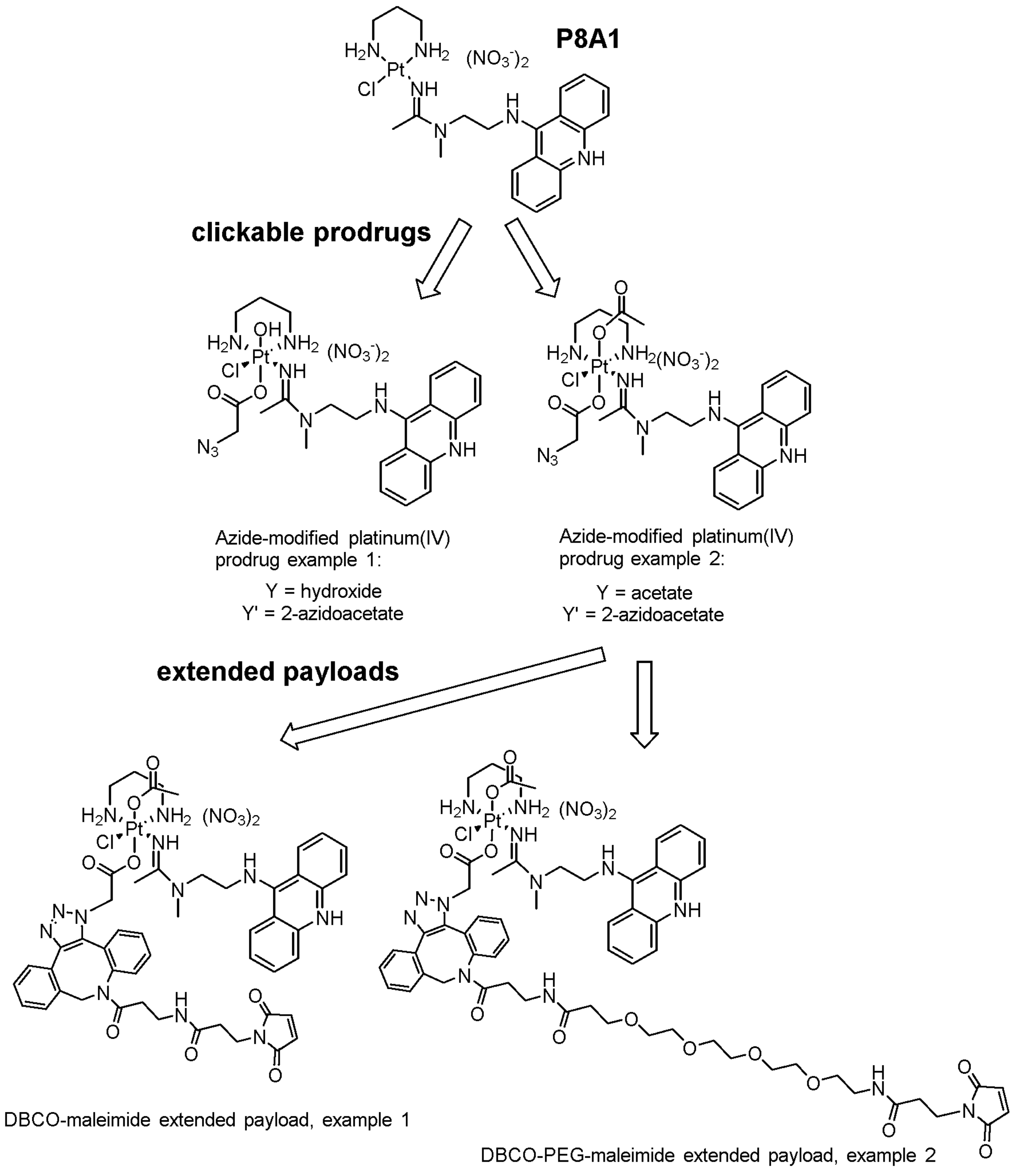
FIG. 1 shows an exemplary synthesis of compounds with a linker derived from click chemistry.

Various embodiments of this patent document provide platinum-acridine compounds and analogs thereof for cancer treatment. This novel approach is designed based on the guiding principle that rapid formation of unique DNA adducts would overcome tumor resistance to DNA-targeted drugs, including conventional platinum-based pharmaceuticals.

Platinum-acridines and analogs thereof bind to DNA via a mechanism that involves intercalation and platination nucleobase nitrogen, a more severe form of DNA damage than the cross-links observed for cisplatin. On a per-adduct basis, the hybrid agents are more potent inhibitors of DNA synthesis than cisplatin, which induce replication fork arrest and a high level of DNA double-strand breaks requiring specialized DNA repair modules. They are also more efficient inhibitors of RNA polymerase II (Pol II) and have been demonstrated to target the cell's nucleoli, the sites of ribosomal DNA (rDNA) transcription. These mechanisms most likely contribute to the high cytotoxicity of platinum-acridines and their analogs, for instance in NSCLC cell lines, which respond to low-nanomolar concentrations of these agents. The results from mechanistic studies in cell-free systems, human cancer cells, and chemical genomic fitness profiling in *S. Cerevisiae* are consistent with nuclear DNA as the principal target of these agents, which suggests that platinum-acridines overcome chemoresistance to cisplatin at the DNA level. Most compellingly, platinum-acridines maintain up to 1000-fold higher activity than cisplatin in notoriously DNA repair-proficient NSCLC, even though the hybrid adducts are repaired more rapidly than the classical cross-links in these cells.

Besides demonstrating a complete lack of similarity of the compound's antitumor profile with that of the classical platinum drugs, the platinum-acridines and their analogs are also associated with a critical cellular target. As is further illustrated in the examples, human multidrug and toxin extrusion protein hMATE1 (SLC47A1) has been validated as a predictive marker of chemosensitivity to platinum-acridines and their analogs. This epigenetically activatable transporter thus serves as a target for personalized cancer treatment.

As a person of skill in the art would understand, the present invention encompasses any reasonable combinations of the illustrated embodiments disclosed herein, which would provide a beneficial effect to a cancer patient.

The terminology used in the description of the invention herein is for describing particular embodiments only and is not intended to be limiting of the invention. As used herein, the singular forms "a," "an," and "the" are intended to include the plural forms as well, and vice versa, unless the context clearly indicates otherwise.

The term "about," as used herein, is intended to mean up to ±10% of an indicated value. Any ranges mentioned in the specification or the claims are to be understood as including the range itself and anything subsumed therein, including both endpoints.

The term "alkyl" refers to monovalent or divalent saturated alkane radical groups particularly having up to about 18 carbon atoms, more particularly as a lower alkyl, from 1 to 8 carbon atoms and still more particularly, from 1 to 6 carbon atoms. The hydrocarbon chain may be either straightchained or branched. The term "C1-C10 alkyl" refers to alkyl groups having 1, 2, 3, 4, 5, 6, 7, 8, 9 or 10 carbon atoms. Similarly, the term "C1-C6 alkyl" refers to alkyl groups having 1, 2, 3, 4, 5, or 6 carbon atoms. Non-limiting examples include groups such as methyl, ethyl, n-propyl, isopropyl, n-butyl, iso-butyl, tert-butyl, n-hexyl, n-octyl, tert-octyl and the like.

The term "aryl" refers to a monovalent or divalent aromatic hydrocarbon group derived by the removal of one hydrogen atom from a single carbon atom of a parent aromatic ring system. Typical aryl groups include, but are not limited to, groups derived from aceanthrylene, acephenanthrylene, anthracene, azulene, benzene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenyl, phenanthrene, picene, and the like. Particularly, an aryl group comprises from 6 to 14 carbon atoms.

The term "amino" or "amine" when describing a group instead of a neutral molecules refers to a primary group ($—NH_2$), a secondary amino (e.g. monoalkyl-NH radical) or a tertiary amino group (dialkyl-N radical). In the context of an alkyl being interrupted by an amino group, the amino can also refer to a di-radical.

The term "alkyne-containing group" refers to an alkyne which can be a terminal alkyne or a strained alkyne such as DBCO.

The term "amino acid" includes histidine, isoleucine, leucine, lysine, methionine, phenylalanine, threonine, tryptophan, valine, alanine, asparagine, aspartic acid, glutamic acid, serine, arginine, cysteine, glutamine, glycine, proline, tyrosine and derivatives thereof.

The term "biologically active moiety" refers to an organic structure that facilitates the absorption or delivery of a platinum-containing compound or enhances the therapeutic activity of the compound.

The term "pharmaceutically acceptable carrier" includes any and all solvents, dispersion media, coatings, antibacterial and antifungal agents, isotonic and absorption delaying agents, and the like that are physiologically compatible. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences. Preferably, the carrier is suitable for intravenous, intramuscular, subcutaneous, parenteral, spinal or epidermal administration (e.g., by injection or infusion). The therapeutic compounds may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19).

The term "cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

The term "halogen" refers to F, Cl, Br, or I.

The term "pseudohalide" refers to univalent anions (or functional groups) which form hydracids with hydrogen and form insoluble salts with Ag (silver) such as cyanides, cyanates, isocyanates, rhodanides (i.e. thiocyanates and isothiocyanates), selenocyanogens, tellurorhodanides and azides.

The term "therapeutically effective amount" refers to an amount of a compound or a conjugate effective to prevent, alleviate or ameliorate symptoms of disease or prolong the survival of the subject being treated. Determination of a therapeutically effective amount is well within the capability of those skilled in the art, especially in light of the detailed disclosure provided herein.

The term "pharmaceutical composition" refers to a mixture of a compound or a conjugate disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. In some embodiments, pharmaceutically acceptable salts of the compounds disclosed herein are provided.

The term "physiologically acceptable" or "pharmaceutically acceptable" refers to a carrier or diluent that does not abrogate the biological activity and properties of the compound.

The term "subject" refers to a mammalian animal or a human.

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In some embodiments, "treating" or "treatment" refers to delaying the onset of the disease or disorder, or even preventing the same.

Compounds

An aspect of the invention provides a compound or a pharmaceutically acceptable salt thereof. The compound is represented with the following general Formula I:

I

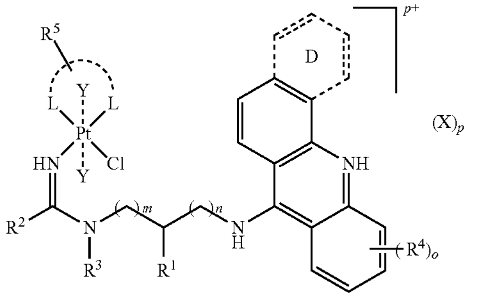

wherein, each L independently represents monodentate $NH_3$ or an amine ligand wherein the nitrogen coordinates to Pt, further wherein the two amine ligands optionally link up to form a diamine ligand (chelate);

X represents nitrate or halide;

Each Y independently represents a ligand selected from the group consisting of halide, hydroxide, pseudohalide, acetate, and

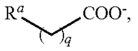

wherein q is an integer from 1 to 6 inclusive, wherein $R^a$ represents (a) $C_{2-4}$alkyl, OH, SH, $NH_2$, COOH, amino acids, CN, an alkyne-containing group, $N_3$, $(OCH_2CH_2)_rOC_{1-4}$alkyl, $(NHCH_2CH_2)_rNHC_{1-4}$alkyl, wherein r is an integer from 1 to 4 inclusive;

(b) L-E, wherein E is terminal electrophilic functional group such as maleimide-based moiety, self-stabilizing maleimide, dibromomaleimide, next generation maleimides (NGM), 2'-pyridyldithio variant, SMCC, aromatic or vinyl sulfone, acrylate, haloacetyl, N-hydroxysuccinimidyl esters (e.g. NHS, sulfo-NHS), anhydrides, fluorophenyl esters, and activated lactams;

or (c) L-M, wherein M is a targeting moiety, such as a peptide, protein, synthetic polymer, aptamer, or nanoparticle;

wherein L in (b) and (c) is a linker comprising a linkage formed from azide and alkyne;

wherein when Y is present, Pt is Pt(IV), and when Y is void, Pt is Pt(II);

o is 0, 1, 2 or 3 p is 1 or 2;

m is 0, 1, 2 or 3;

n is 0, 1, 2 or 3;

D is an optional aromatic ring;

$R^1$, $R^2$ and $R^3$ each independently represents a $C_{1-10}$ alkyl, wherein one or more carbons of the $C_{1-10}$ alkyl is optionally (a) replaced with a moiety selected from the group consisting of amino, oxygen, sulfur, amide, ester, carbamate, sulfonamide, sulfonyl, carbonate, ketone, and disulfide; or (b) substituted with a moiety selected from the group consisting of hydroxy, imino, oxo, cyano, $C_{1-10}$ alkoxy, $C_{1-10}$ alkylthio, $C_{1-6}$ alkylsulfonyl, and di-$C_{1-10}$ alkylamine;

$R^4$ is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, or (mono-, di-, or trihalogeno)methyl;

$R^5$ represents an optional substituent of L and is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, (mono-, di-, or trihalogeno) methyl, or $C_{1-10}$ alkoxy.

In some embodiments, it is also provided that the compound meets at least one of (i), (ii), (iii), (iv) and (v):

(i) $R^1$ and $R^3$ link up to form a 4 to 8 membered ring;

(ii) $R^2$ and $R^3$ link up to form a 5 to 8 membered ring; and (iii) at least one of the two Ys is selected from the group consisting of Cl, OH, acetate, and

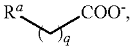

wherein q is an integer from 1 to 6 inclusive, $R^a$ represents $C_{1-4}$alkyl, OH, SH, $NH_2$, COOH, CN, an alkyne-containing group, $N_3$, $(OCH_2CH_2)_rOC_{1-4}$alkyl or $(NHCH_2CH_2)_rNHC_{1-4}$alkyl, wherein r is an integer from 1 to 4 inclusive;

(iv) at least one of the two Ys is present and is L-E, and (v) at least one of the two Ys is present and is L-M.

In some embodiments, the compound is not

PA-0

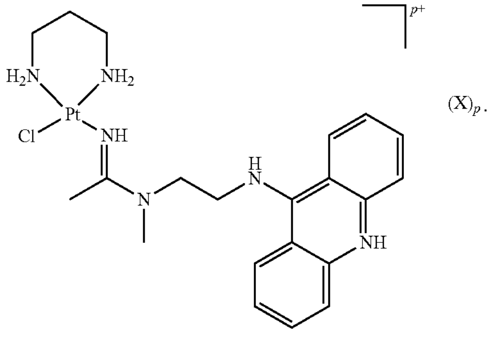

Non-limiting examples of ligand L include pyridine, $NH_3$, $NH_2R^b$, $NH(R^b)_2$, or $N(R^b)_3$, herein each $R^b$ is independently $C_1$-$C_6$alkyl. Two Ls may also link up to form a bidentate ligand.

Examples of bidentate ligand L include the following:

a

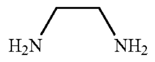

b

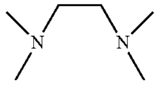

c

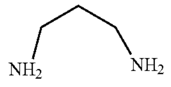

-continued

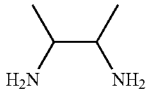

d

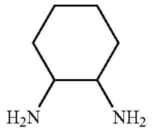

e

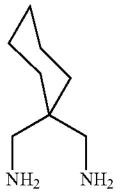

f

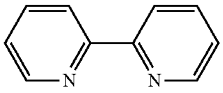

g

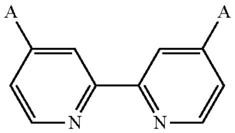

h

In some embodiments, the two L ligands link up to form $NH_2—(CH_2)_v—NH_2$, wherein v is 1, 2, 3, 4 or 5.

Additional examples of diamine ligands include the following:

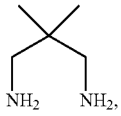,

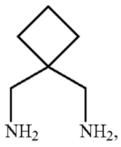,

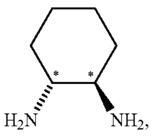,

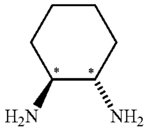 and 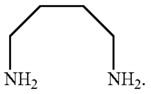.

In some embodiments, D is void and p is 2.

In some embodiments, the two Ys are the same. In some embodiments, the two Ys are the same and are selected from chloride, hydroxide or acetate. When $R^a$ in

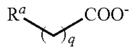

is an amino acid, it may attach to the $(CH_2)_q$ moiety via the amino group or carboxylic acid group. In some embodiments, one of the two Ys is chloride and the other is

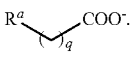.

In some embodiments, the compound is represented by Formula II, wherein $R^1$ and $R^3$ link up to form a 4 to 8 membered ring A. In some embodiments, m is 1 and n is 0. The carbon with asterisk has an R or S configuration. Alternatively, the compound is a racemic mixture of R and S isomers. In some embodiments, the D ring is not present (void).

Formula II

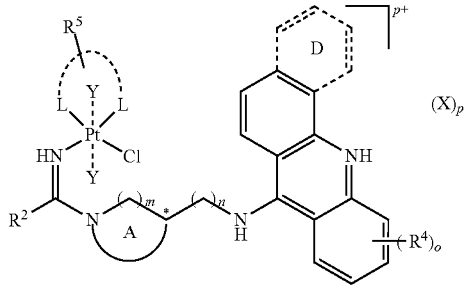

In some embodiments, the compound is represented by Formula II-A. In some embodiments, the compound is represented by Formula II-B. In some embodiments, the D ring is not present (void)

Formula II-A

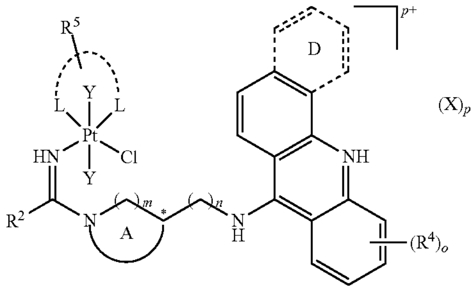

Formula II-B

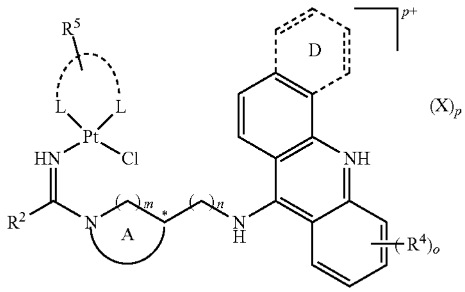

In some embodiments, ring A is a 5 or 6-membered ring. In some embodiments, m is 1 and n is 0. In some embodiments, ring A is

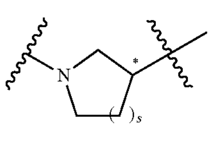, wherein s is 1 or 2. In some embodiments, the asterisked carbon in ring A has R configuration. In some embodiments, the asterisked carbon in ring A has S configuration.

Non-limiting examples of compound of Formula I includes the following. Further exemplary embodiments include Pt(IV) compounds prepared from the following compounds, wherein the corresponding Pt(IV) compounds have Y selected from the group consisting of Cl, OH, and

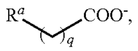

wherein q is an integer from 1 to 6 inclusive, $R^a$ represents $C_{1-4}$alkyl, OH, SH, $NH_2$, COOH, CN, an alkyne-containing group, $N_3$, $(OCH_2CH_2)_rOC_{1-4}$alkyl or $(NHCH_2CH_2)_r$-$NHC_{1-4}$alkyl, wherein r is an integer from 1 to 4 inclusive.

PA-1

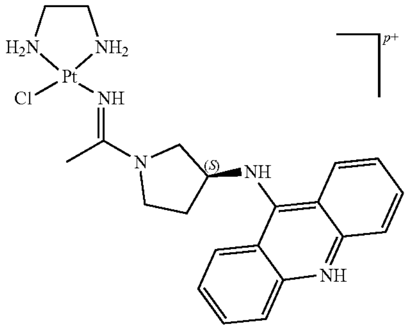

$(X)_p$,

PA-2

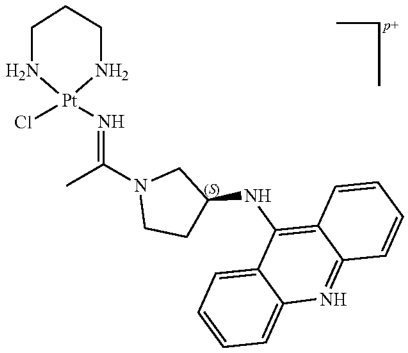

$(X)_p$,

PA-3

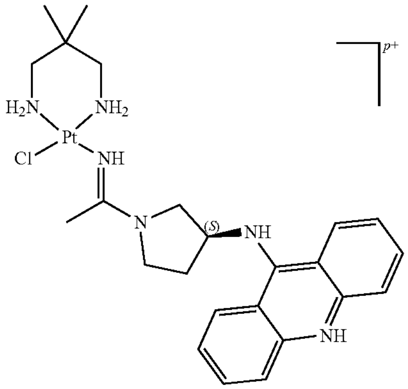

$(X)_p$,

-continued

PA-4

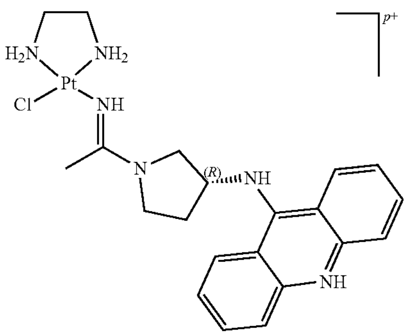

$(X)_p$,

PA-5

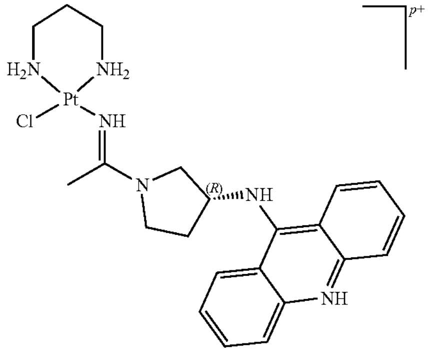

$(X)_p$,

PA-6

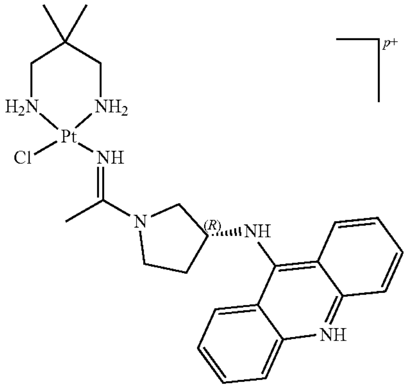

$(X)_p$,

PA-7

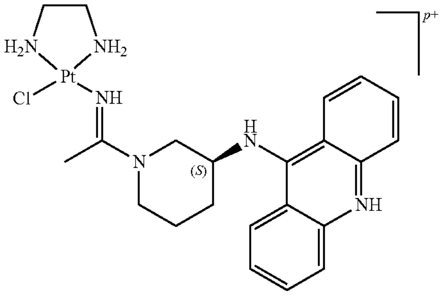

$(X)_p$,

-continued
PA-8
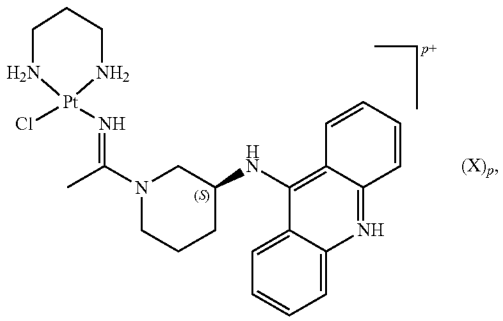
PA-9
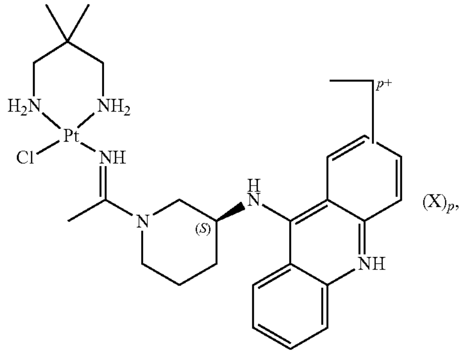
PA-10
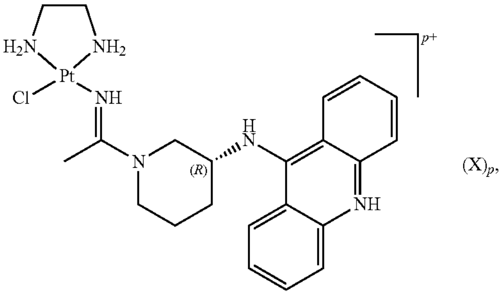
PA-11
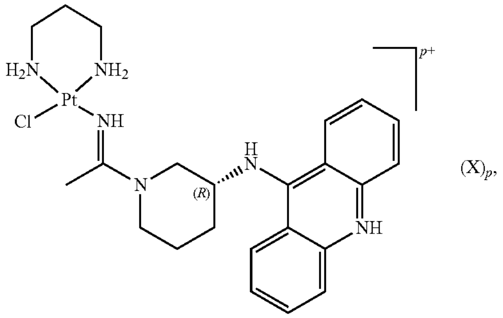
-continued
PA-12
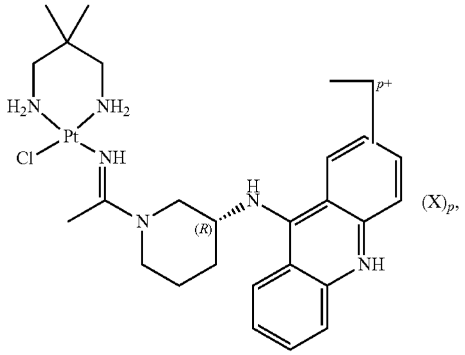
PA-13
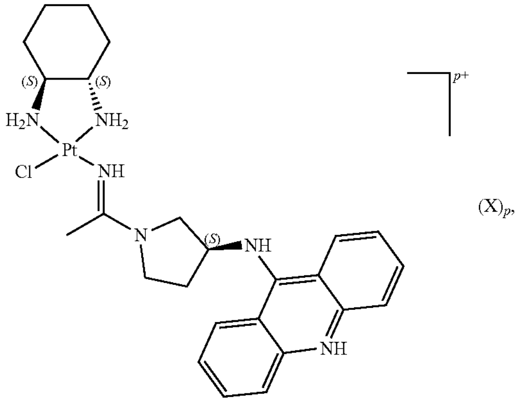
PA-14
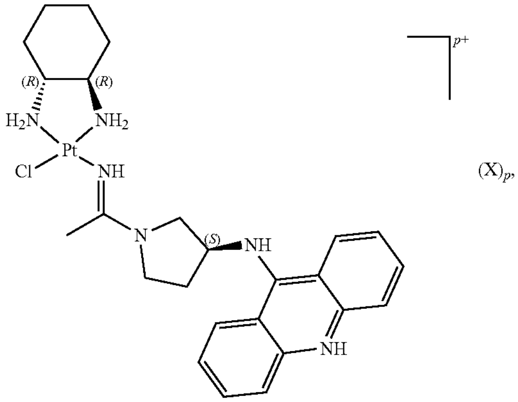
PA-15
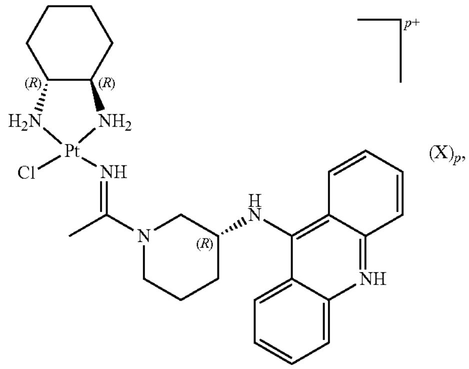

-continued
PA-16
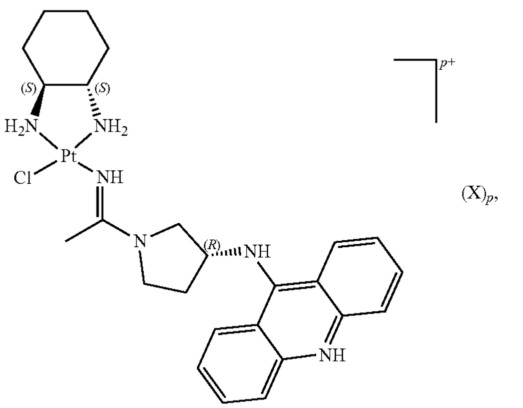
PA-17
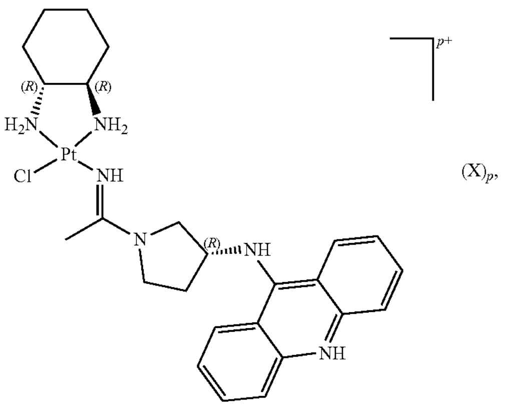
PA-18
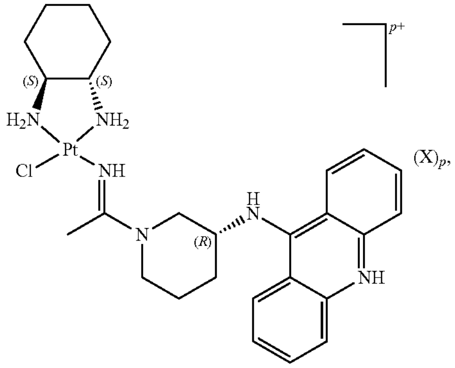
PA-19
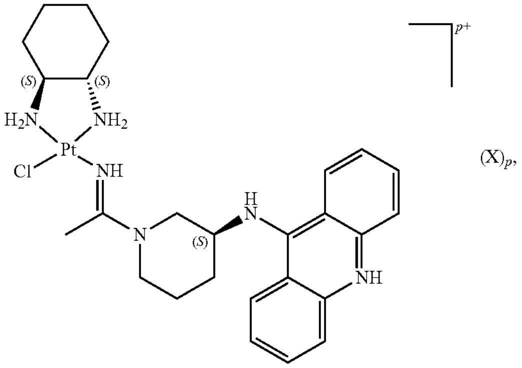
-continued
PA-20
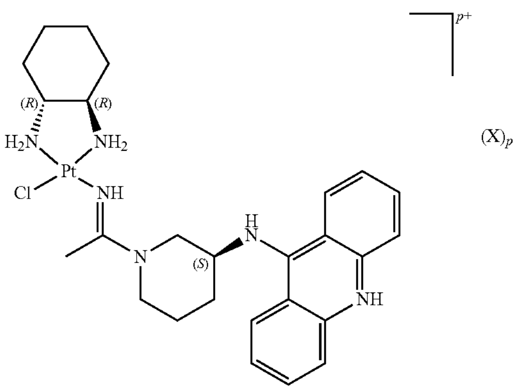
and
PA-0
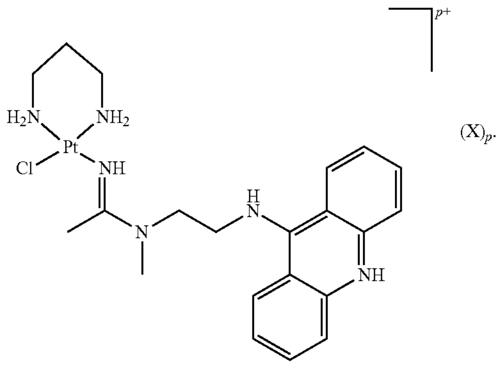
In some embodiments, the above illustrated compounds have p as 2 and X as nitrate.
In some embodiments, the compound of Formula I is represented by Formula III, wherein $R^2$ and $R^3$ link up to form a 5 to 8 membered ring. In some embodiments, ring B is a 5 or 6-membered ring.
Formula III
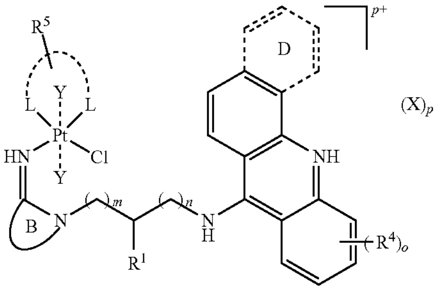
In some embodiments, ring B is
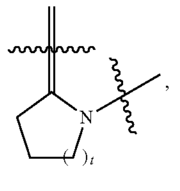
wherein t is 1 or 2.

In some embodiments of Formula III, the compound is represented by Formula III-A or Formula III-B.

Formula III-A

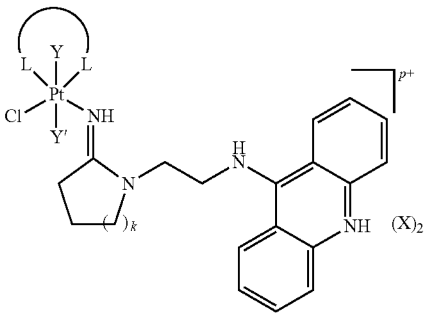

or

Formula III-B

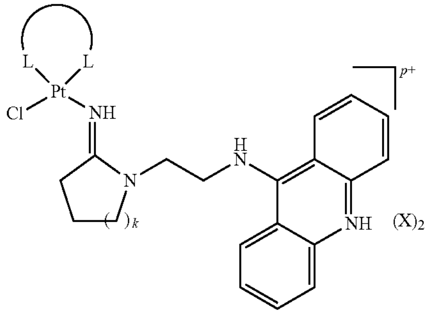

In some embodiments, the compound of Formula I' includes the following

PA-21

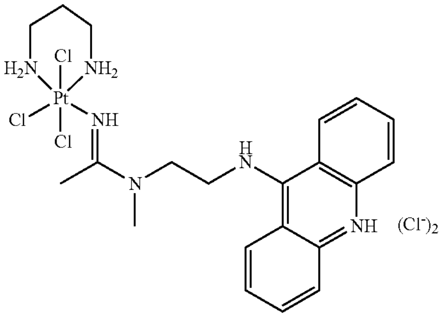

PA-22

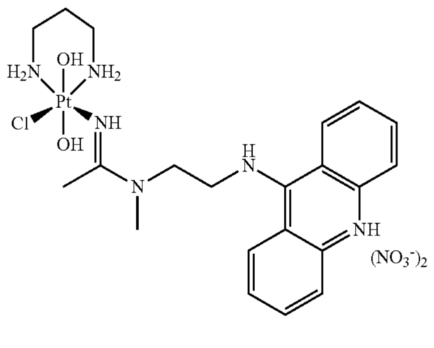

-continued

PA-23

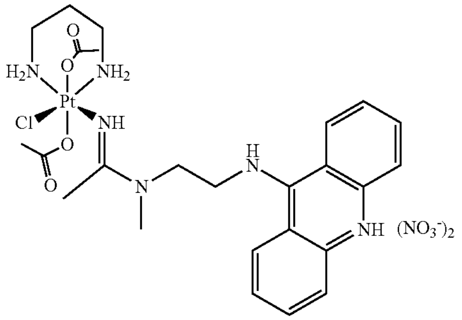

In some embodiments of the compound of Formula I, at least one of the two Ys is present and is L-E. In some embodiments, two Ys are present and only one is L-E. In some embodiments, E is a maleimido-based moiety or a haloacetyl-based moiety. Non-limiting examples of suitable precursors for maleimido-based moiety include maleimide, N-succinimidyl 4-(maleimidomethyl)cyclohexanecarboxylate (SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimidobutyric acid N-succinimidyl ester (GMBS), ε-maleimidcaproic acid N-hydroxysuccinimide ester (EMCS), m-maleimidobenzoyl-N-hydroxysuccinimide ester(MBS), N-(α-maleimidoacetoxy)-succinimide ester (AMAS), succinimidyl-6-(β-maleimidopropionamido) hexanoate (SMPH), N-succinimidyl 4-(p-maleimidophenyl)-butyrate (SMPB), and N-(p-maleimidophenyl)isocyanate (PMPI). Non-limiting examples of suitable precursors for haloacetyl-based moiety (e.g. bromo or iodo acetamide) include N-succinimidyl-4-(iodoacetyl)-aminobenzoate (SIAB), N-succinimidyl iodoacetate (SIA), N-succinimidyl bromoacetate (SBA), or N-succinimidyl 3-(bromoacetamido)propionate (SBAP). Additional examples of groups for forming a linkage include carbonyl, 2-amino-benzaldehyde or 2-amino-acetophenone group, hydrazide, oxime, potassium acyltrifluoroborate, O-carbamoylhydroxylamine, trans-cyclooctene, tetrazine, and triarylphosphine. In addition to thiol/maleimide and azide/alkyne site specific conjugation group pair used in this invention, as will be appreciated by those of ordinary skill, other known pairs of site-specific conjugation groups, such as thiol/2'-pyridyldithio pair; thiol/sulfone pair; DBCO/azide pair; trans-cyclooctenes/tetrazines pair; carbonyl/hydrazide pair; carbonyl/oxime pair; azide/triarylphosphine pair; potassium acyltrifluoroborates/O-carbamoylhydroxylamines pair, can be similarly designed and used as alternatives for the same purpose if desired. The foregoing list of site-specific conjugation group pairs is merely illustrative and not intended to restrict the type of site-specific conjugation group pairs suitable for use herein. The condition to form a ring structure through azide-alkyne click chemistry is well-known in the field of organic chemistry.

In some embodiments, the alkyne for forming the linkage is selected from dibenzocyclooctynes (DIBO, DBCO (DIBAC), BARAC), bicyclooctanonyne (BCN), and difluorocyclooctyne (DIFO). The positions of the alkyne and azide are interchangeable in the precursors.

In some embodiments, the linker may include one or more components including Linker chains and/or linkages (internal or terminal) may be independently selected from $—(CH_2)_aC(O)NR^x—$, $—C(O)NR^x—$, $—(CH_2)_aC(O)NR^x(CH_2)_b—$, $—(CH_2)_a—$, $—(CH_2)_aO(CH_2CH_2O)_c—$, $—(CH_2)_a$heterocyclyl-, $—(CH_2)_aC(O)—$, and $—(CH_2)_aNR^x—$, $—CR^x{=}N—NR^x—$, $—CR^x{=}N—O—$, $—CR^x{=}N—NR_y—CO—$, $—N{=}N—CO—$, $—S—S—$, and any combination thereof, wherein a, b, and c are each an integer selected from 0 to 25, all subunits (e.g. 0, 1, 2, 3, 4, 5, 6, 7, 8, 9, 10, ect.) included; and $R^x$ and $R^y$ independently represent hydrogen or a C1-C10 alkyl.

In some embodiments, the linker L further includes $(CH_2)_xO(CH_2CH_2O)_y$, wherein x is an integer selected from 0 to 25 and n is an integer selected from 1 to 25.

The linker may contain a degradable/cleavable linkage. Non-limiting examples include disulfide, carbonate, hydrazide, hydrazone, dipeptides (Val-Cit, Val-Ala), and self-immolative para-aminobenzyl carbamate (PABC). The degradation of the linkage can promote the release of a therapeutic agent or diagnostic agent. It may also assist with clearance of the compound from the blood circulation. The linkage may be hydrolytically, enzymatically, or photonically degradable. Exemplary degradable bonds for the linkage include enzyme-sensitive peptide linker bonds, self-immolative linker bonds, acid and base-sensitive linker bonds, pH sensitive linker bonds, multifunctional organic linking agent bonds, multifunctional inorganic crosslinking agent bonds and peptidic backbone bonds. In some embodiments, the linkage is degradable by hydrolysis. Hydrolysis involves chain scission when water is added to the conjugate. Anhydrides, esters and amides are all susceptible to hydrolysis. For example, PEG can be functionalized with degradable ester linkages using lactide or glycolide segments.

In some embodiments, the linker contains an enzymatically cleavable linkage. These enzymatic cleavage sites can be used to allow degradation and/or to introduce the ability to release any bound therapeutic molecule. The preparation of sequence-specific enzymatic degradation of peptides incorporated into hydrogels are well known in the art (e.g. Hubbell-West, J. L.; Hubbell, J. A. Macromolecules 1999, 32, 241-244). For example, matrix metalloproteinase (MMP) sensitive linkages can be readily introduced into hydrogels via Michael addition of cysteine-functionalized peptides across acrylates, maleimides and vinyl sulfones.

In some embodiments, the linker contains a photonically cleavable linkage. For example, photodegradation of hydrogels can be introduced by using an ortho-nitrobenzyl (o-NB) linker group.

Non-limiting example compounds are shown below. Additional examples are provided in FIG. 2.

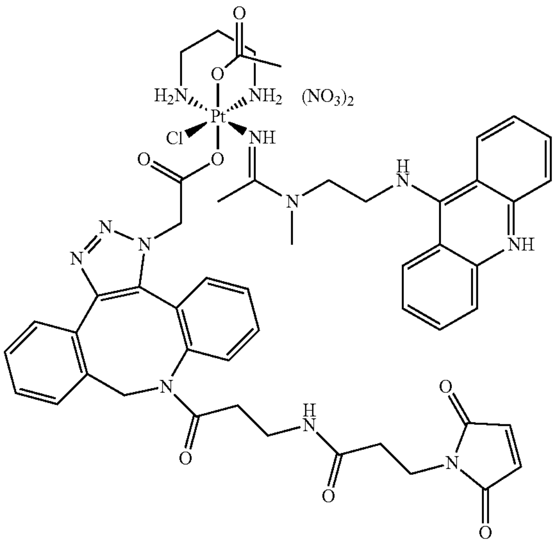

or

-continued

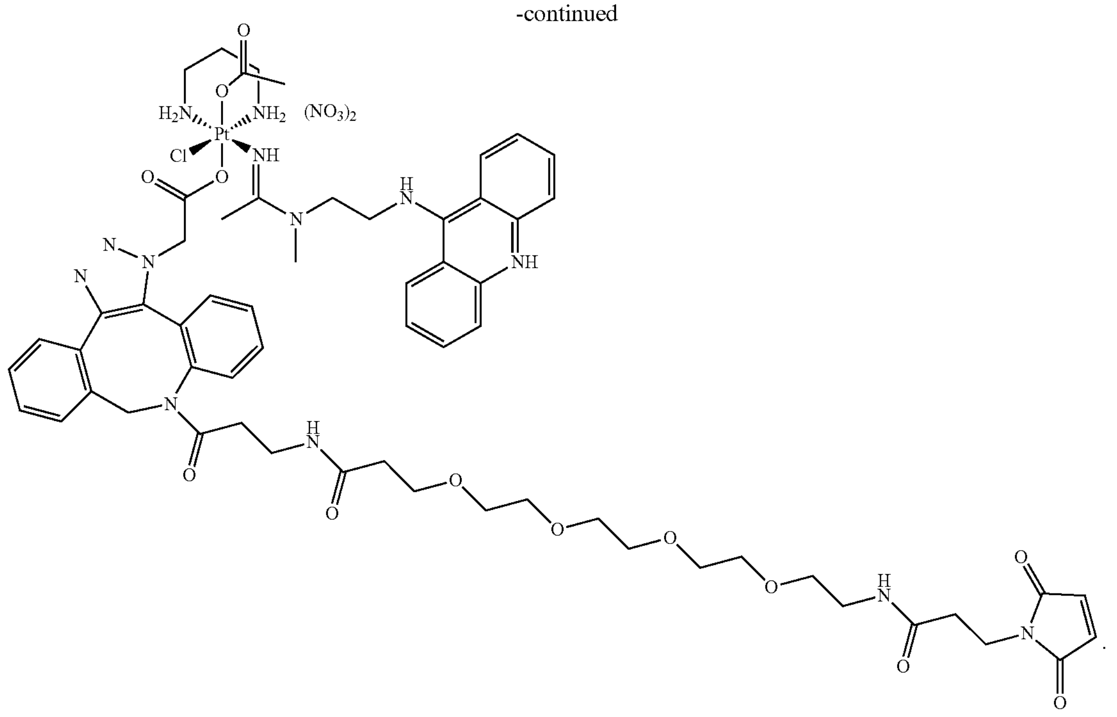

In some embodiments of the compound of Formula I, at least one of the two Ys is present and is L-M. In some embodiments, two Ys are present and only one is L-M. In some embodiments, M is a peptide, protein, synthetic polymer, aptamer, or nanoparticle. In some embodiments, M is an antibody or an antigen-binding portions thereof. In some embodiments, M is a monoclonal antibody such as human monoclonal antibodies that bind to different antigens or epitopes. Preferably the antibodies are human antibodies, although the antibodies can also be, for example, murine antibodies, chimeric antibodies, humanized antibodies, or a combination thereof. Non-limiting examples of M include IgG1, IgG2, and IgG4 based antibodies, anti-CD22, anti-CD33, anti-CD19 and anti-CD3 antibodies (e.g. targeted at HER2, TROP2, NECTIN4), and fragments thereof. The scope of L is as described above. M can be conjugated to L via the reaction between a functional group (e.g thiol or amino) of M and the terminal functional group E (e.g. maleimido-based moiety) of L.

Monoclonal antibody techniques allow for the production of specifically binding agents in the form of specifically binding monoclonal antibodies or fragments thereof. For creating monoclonal antibodies, or fragments thereof, one can use conventional hybridoma techniques. Alternatively monoclonal antibodies, or fragments thereof, can be obtained by the use of phage libraries of scFv (single chain variable region), specifically human scFv (see e.g. U.S. Pat. No. 5,885,793, WO 92/01047, WO 99/06587).

In one embodiment, at least one of the recognition binding moieties is a monovalent antibody fragment. In one embodiment the monovalent antibody fragment is derived from a monoclonal antibody. Monovalent antibody fragments include, but are not limited to Fab, Fab'-SH, single domain antibody, $F(ab')_2$, Fv, and scFv fragments. Thus, in one embodiment the monovalent antibody fragment is selected from the group comprising Fab, Fab'-SH, single domain antibody, $F(ab')_2$, Fv, and scFv fragments. In one embodiment at least one of the recognition binding moieties of the multi-specific molecules disclosed herein is a single domain antibody, or scFv or a Fab-fragment, or a Fab'-fragment of a monoclonal antibody.

One or more of the recognition binding moiety in the multi-specific molecules can also be diabodies or single-domain antibodies. Diabodies are antibody fragments with two antigen-binding sites that may be bivalent or bispecific (see e.g. EP 0 404 097, WO 93/01161, Hudson, P. J., et al., Nat. Med. 9 (2003) 129-134, and Holliger, P., et al., Proc. Natl. Acad. Sci. USA 90 (1993) 6444-6448). Triabodies and tetrabodies as described in Hudson, P. J., et al., Nat. Med. 9 (2003) 129-134 can also be used for a recognition binding moiety in the multi-specific molecules. Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; U.S. Pat. No. 6,248,516).

A recognition binding moiety in the multi-specific molecules can be an Fv, which is a minimum antibody fragment that contains a complete antigen-binding site and is devoid of constant region. For a review of scFv, see, e.g., Plueckthun, in The Pharmacology of Monoclonal Antibodies, vol. 113, Rosenburg and Moore (eds.), (Springer-Verlag, New York, 1994), pp. 269-315, WO 93/16185, U.S. Pat. Nos. 5,571,894, 5,587,458. Generally, six hyper variable regions (HVRs) confer antigen-binding specificity to an antibody. However, even a single variable domain (or half of an Fv comprising only three HVRs specific for an antigen) has the ability to recognize and bind its antigen.

In one embodiment the monovalent antibody fragments is a two-chain Fv species consisting of a dimer of one heavy- and one light-chain variable domain in tight, non-covalent association. In one embodiment the monovalent antibody fragments is a single-chain Fv (scFv) species consisting of one heavy-chain and one light-chain variable domain covalently linked by a flexible peptide linker.

A Fab fragment of an antibody contains the heavy-chain and light-chain variable domains as well as the constant domain of the light chain and the first constant domain (CH1) of the heavy chain. A Fab' fragments differ from a Fab fragment by the addition of a few residues at the carboxy terminus of the heavy chain CH1 domain including one or more cysteines from the antibody hinge region. Fab'-SH denotes a Fab' in which the cysteine residue(s) of the constant domains bear a free thiol group.

Various techniques have been developed for the production of antibody fragments. Traditionally, antibody fragments can be obtained via proteolytic digestion of full length antibodies (see, e.g., Morimoto, K., et al., J. Biochem. Biophys. Meth. 24 (1992) 107-117, Brennan, M., et al., Science 229 (1985) 81-83). For example, papain digestion of full length antibodies results in two identical antigen-binding fragments, called "Fab" fragments, each with a single antigen-binding site, and a residual "Fc" fragment. For a review of certain antibody fragments, see Hudson, P. J., et al., Nat. Med. 9 (2003) 129-134.

Antibody fragments can also be produced directly by recombinant means. Fab, Fv and scFv antibody fragments can all be expressed in and secreted from e.g. *E. coli*, thus, allowing the facile production of large amounts of these fragments. Antibody fragments can be isolated from antibody phage libraries according to standard procedures. Alternatively, Fab'-SH fragments can be directly recovered from *E. coli*. (Carter, P., et al., Bio/Technology 10 (1992) 163-167). Mammalian cell systems can be also used to express and, if desired, secrete antibody fragments.

A number of therapeutic antibodies directed against cell surface molecules and/or their ligands are known. These antibodies can be used for the selection and construction of tailor-made specific recognition binding moiety in the multispecific molecules. Examples include Blinatumomab/BLINCYTO Rituxan/MabThera/Rituximab, H7/Ocrelizumab, Zevalin/Ibrizumomab, Arzerra/Ofatumumab (CD20), HLL2/Epratuzumab, Inotuzomab (CD22), Zenapax/Daclizumab, Simulect/Basiliximab (CD25), Herceptin/Trastuzumab, Pertuzumab (Her2/ERBB2), Mylotarg/Gemtuzumab (CD33), Raptiva/Efalizumab (Cd11a), Erbitux/Cetuximab (EGFR, epidermal growth factor receptor), IMC-1121B (VEGF receptor 2), Tysabri/Natalizumab (α4-subunit of α4β1 and α4β7 integrins), ReoPro/Abciximab (gpIIb-gpIIa and αvβ3-integrin), Orthoclone OKT3/Muromonab-CD3 (CD3), Benlysta/Belimumab (BAFF), Tolerx/Oteliximab (CD3), Soliris/Eculizumab (C5 complement protein), Actemra/Tocilizumab (IL-6R), Panorex/Edrecolomab (EpCAM, epithelial cell adhesion molecule), CEA-CAMS/Labetuzumab (CD66/CEA, carcinoembryonic antigen), CT-11 (PD-1, programmed death-1 T-cell inhibitory receptor, CD-d279), H224G11 (c-Met receptor), SAR3419 (CD19), IMC-A12/Cixutumumab (IGF-1R, insulin-like growth factor 1 receptor), MEDI-575 (PDGF-R, platelet-derived growth factor receptor), CP-675, 206/Tremelimumab (cytotoxic T lymphocyte antigen 4), RO5323441 (placenta growth factor or PGF), HGS1012/Mapatumumab (TRAIL-R1), SGN-70 (CD70), Vedotin (SGN-35)/Brentuximab (CD30), and ARH460-16-2 (CD44).

A number of cell surface markers and their ligands are known. For example cancer cells have been reported to express at least one of the following cell surface markers and or ligands, including but not limited to, carbonic anhydrase IX, alpha-fetoprotein, alpha-ctinin-4, A3 (antigen specific for A33 antibody), ART-4, B7-1, B7-H1, Ba-733, BAGE, BrE3-antigen, CA125, CAMEL, CAP-1, CASP-8/m, CCCL19, CCCL21, CD1, CD1a, CD2, CD3, CD4, CDS, CD8, CD1-1A, CD14, CD15, CD16, CD18, CD19, CD20, CD21, CD22, CD23, CD25, CD29, CD30, CD32b, CD33, CD37, CD38, CD40, CD4OL, CD45, CD46, CD54, CD55, CD59, CD64, CD66a-e, CD67, CD70, CD74, CD79a, CD80, CD83, CD95, CD126, CD133, CD137, CD138, CD147, CD154, CDC27, CDK-4/m, CDKN2A, CTLA-4, CXCR4, CXCR7, CXCL12, HIF-1-α, colon-specific antigen-p (CSAp), CEA (CEACAMS), CEACAM6, c-met, DAM, EGFR, EGFRvIII, EGP-1, EGP-2, ELF2-M, Ep-CAM, Flt-1, Flt-3, folate receptor, G250 antigen, GAGE, GROB, HLA-DR, HM1.24, human chorionic gonadotropin (HCG) and its subunits, HER2/neu, HMGB-1, hypoxia inducible factor (HIF-1), HSP70-2M, HST-2 or 1a, IGF-1R, IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, insulin-like growth factor-1 (IGF-1), KC4-antigen, KS-1-antigen, KS 1-4, LAGS, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUCS, MUM-1/2, MUM-3, NCA66, NCA95, NCA90, pancreatic cancer mucin, PD-1 and its receptor, PD-L1, PD-L2, placental growth factor, p53, PLAGL2, prostatic acid phosphatase, PSA, PRAME, PSMA, P1GF, ILGF, ILGF-1R, IL-6, IL-25, RSS, RANTES, T101, SAGE, 5100, survivin, survivin-2B, TAC, TAG-72, tenascin, TIM3(T-cell immunoglobulin and mucin-domain containing-3), TRAIL receptors, TNF-α, Tn-antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi et al., Clin. Cancer Res. 12 (2006) 5023-5032; Parmiani et al, J. Immunol. 178 (2007) 1975-1979; Novellino et al., Cancer Immunol. Immunother. 54 (2005) 187-207). Thus, antibodies recognizing such specific cell surface receptors or their ligands can be used for specific and selective recognition binding moieties in the multi-specific molecules of this invention, targeting and binding to a number/multitude of cell surface markers or ligands that are associated with a disease.

In some embodiments, for the treatment of cancer/tumors multispecific binding molecules/multi-specific antibodies are used that target tumor-associated antigens (TAAs), such as those reported in Herberman, "Immunodiagnosis of Cancer", in Fleisher ed., "The Clinical Biochemistry of Cancer", page 347 (American Association of Clinical Chemists, 1979) and in U.S. Pat. Nos. 4,150,149; 4,361,544; and 4,444,744.

Reports on tumor associated antigens include Mizukami et al., Nature Med. 11 (2005) 992-997; Hatfield et al., Curr. Cancer Drug Targets 5 (2005) 229-248; Vallbohmer et al., J. Clin. Oncol. 23 (2005) 3536-3544; and Ren et al., Ann. Surg. 242 (2005) 55-63), each incorporated herein by reference with respect to the TAAs identified. Where the disease involves a lymphoma, leukemia or autoimmune disorder, targeted antigens may be selected from the group consisting of CD4, CDS, CD8, CD14, CD15, CD19, CD20, CD21, CD22, CD23, CD25, CD33, CD37, CD38, CD40, CD4OL, CD46, CD54, CD67, CD74, CD79a, CD80, CD126, CD138, CD154, CXCR4, B7, MUC1 or 1a, HM1.24, HLA-DR, tenascin, VEGF, P1GF, ED-B fibronectin, an oncogene, an oncogene product (e.g., c-met or PLAGL2), CD66a-d, necrosis antigens, IL-2, T101, TAG, IL-6, MIF, TRAIL-R1 (DR4) and TRAIL-R2 (DRS).

Antibodies against the above-mentioned antigens can be used as the binding sites or moieties to make bispecific antibodies of this invention. The antibodies can be conjugated to the terminal functional group E in the linker moiety via chemistry known in the field. A number of bispecific antibodies can be made against two different targets.

Examples of the antigen pairs include CD19/CD3, BCMA/CD3, different antigens of the HER family in combination (EGFR, HER2, HER3), IL17RA/IL7R, IL-6/IL-23, IL-1β/IL-8, IL-6 or IL-6R/IL-21 or IL-21R, ANG2/VEGF, VEGF/PDGFR-beta, Vascular Endothelial Growth Factor (VEGF) acceptor 2/CD3, PSMA/CD3, EPCAM/CD3, combinations of antigens selected from a group consisting of VEGFR-1, VEGFR-2, VEGFR-3, FLT3, c-FMS/CSF1R, RET, c-Met, EGFR, Her2/neu, HER3, HER4, IGFR, PDGFR, c-KIT, BCR, integrin and MMPs with a water-soluble ligand is selected from the group consisting of VEGF, EGF, PIGF, PDGF, HGF, and angiopoietin, ERBB-3/C-MET, ERBB-2/C-MET, EGF receptor 1/CD3, EGFR/HER3, PSCA/CD3, C-MET/CD3, ENDOSIALIN/CD3, EPCAM/CD3, IGF-1R/CD3, FAPALPHA/CD3, EGFR/IGF-1R, IL 17A/F, EGF receptor 1/CD3, and CD19/CD16. Additional examples of bispecific antibodies can have (i) a first specificity directed to a glycoepitope of an antigen selected from the group consisting of Lewis x-, Lewis b- and Lewis y-structures, Globo H-structures, KH1, Tn-antigen, TF-antigen and carbohydrate structures of Mucins, CD44, glycolipids and glycosphingolipids, such as Gg3, Gb3, GD3, GD2, Gb5, Gm1, Gm2, and sialyltetraosylceramide and (ii) a second specificity directed to an ErbB receptor tyrosine kinase selected from the group consisting of EGFR, HER2, HER3 and HER4. GD2 in combination with a second antigen binding site is associated with an immunological cell chosen from the group consisting of T-lymphocytes NK cell, B-lymphocytes, dendritic cells, monocytes, macrophages, neutrophils, mesenchymal stem cells, neural stem cells.

As used herein, the term "conservative sequence modifications" refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include:

- amino acids with basic side chains (e.g., lysine, arginine, histidine),
- acidic side chains (e.g., aspartic acid, glutamic acid),
- uncharged polar side chains (e.g., glycine, asparagine, glutamine, serine, threonine, tyrosine, cysteine, tryptophan),
- nonpolar side chains (e.g., alanine, valine, leucine, isoleucine, proline, phenylalanine, methionine),
- beta-branched side chains (e.g., threonine, valine, isoleucine) and
- aromatic side chains (e.g., tyrosine, phenylalanine, tryptophan, histidine).

Thus, one or more amino acid residues within the CDR regions of an antibody of the invention can be replaced with other amino acid residues from the same side chain family and the altered antibody can be tested for retained function using the functional assays described herein.

A recognition binding moiety of the invention can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al).

Such framework sequences can be obtained from public DNA databases or published references that include germline antibody gene sequences. For example, germline DNA sequences for human heavy and light chain variable region genes can be found in the "VBase" human germline sequence database (available at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" J. Mol. Biol. 227:776-798; and Cox, J. P. L. et al. (1994) "A Directory of Human Germ-line $V_H$ Segments Reveals a Strong Bias in their Usage" Eur. J. Immunol. 24:827-836; the contents of each of which are incorporated herein by reference. As another example, the germline DNA sequences for human heavy and light chain variable region genes can be found in the GenBank database.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. The numbering of residues in the Fc region is that of the EU index of Kabat.

In still another embodiment, the glycosylation of an antibody can be modified. Glycosylation can be altered to, for example, increase or decrease the affinity of the antibody for antigen or an Fc receptor. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such an approach is described in further detail in U.S. Pat. Nos. 8,008,449 and 6,350,861.

A peptide or protein can be conjugated to the linker using a variety of agents or groups such as N-succinimidyl-3-(2-pyridyldithio) propionate (SPDP), succinimidyl-4-(N-maleiimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido components (such as bis(p-azidobenzoyl) hexane diamine), bis-diazonium derivatives (such as bis-(p-diazoniumbenzoyl)-ethylene diamine), diisocyanates (such as toluene 2,6-diisocyanate), and bis-active fluorine components (such as 1,5-difluoro-2,4-dinitrobenzene). For example, an acid-labile linker, peptidase-sensitive linker, photolabile linker, dimethyl linker, or disulfide-containing linker (Chari, R. V., et al., Cancer Res. 52 (1992) 127-131, U.S. Pat. No. 5,208,020) can be used. Additional examples of cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Method of Synthesis

Synthesis of Compounds of Formula I-A

Another aspect of the patent document provides a method of synthesizing a compound of Formula I-A. The substituents of Formula I-A are defined as follows:

Formula I-A

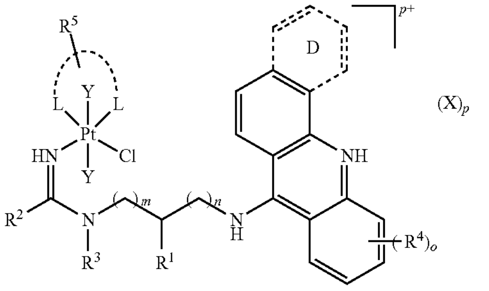

each L independently represents monodentate $NH_3$ or an amine ligand wherein the nitrogen coordinates to Pt, further wherein the two amine ligands optionally link up to form a diamine ligand (chelate);

X represents nitrate or halide;

each Y independently represents hydroxide, acetate or

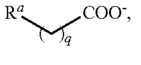

wherein q is an integer from 1 to 6 inclusive, $R^a$ represents $C_{1-4}$alkyl, OH, SH, $NH_2$, COOH, amino acids, CN, an alkyne-containing group, $N_3$, $(OCH_2CH_2)_rOC_{1-4}$alkyl or $(NHCH_2CH_2)_rNHC_{1-4}$alkyl, wherein r is an integer from 1 to 4 inclusive;

o is 0, 1, 2 or 3;

p is 1 or 2;

m is 0, 1, 2 or 3;

n is 0, 1, 2 or 3;

$R^1$, $R^2$ and $R^3$ each independently represents a $C_{1-10}$ alkyl, wherein one or more carbons of the $C_{1-10}$ alkyl is optionally (a) replaced with a moiety selected from the group consisting of amino, oxygen, sulfur, amide, ester, carbamate, sulfonamide, sulfonyl, carbonate, ketone, and disulfide; or (b) substituted with a moiety selected from the group consisting of hydroxy, imino, oxo, cyano, $C_{1-10}$ alkoxy, $C_{1-10}$ alkylthio, $C_{1-6}$ alkylsulfonyl, and di-$C_{1-10}$ alkylamine;

Wherein optionally, (i) $R^1$ and $R^3$ link up to form a 4 to 8 membered ring; or (ii) $R^2$ and $R^3$ link up to form a 5 to 8 membered ring;

$R^4$ is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, or (mono-, di-, or trihalogeno)methyl;

$R^5$ represents an optional substituent of L and is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, (mono-, di-, or trihalogeno) methyl, or $C_{1-10}$ alkoxy;

D represents an optional aromatic ring (e.g. phenyl ring fused to acridine ring).

The method includes treating an intermediate of Formula I-C with an oxidizing agent. The substituents of Formula I-C are the same as defined for Formula I-A except the absence of Y in I-C.

I-C

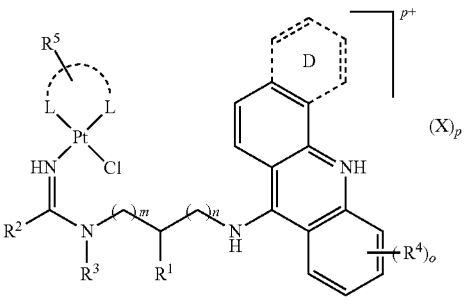

The amount and condition of the oxidation reaction can be modified depending on the specific agent and substrate. In some embodiments, the oxidizing agent is $H_2O_2$, ROOH, ROOR (R=alkyl, aryl, e. g. tert-butyl) or any combination thereof. In some embodiments, the reaction proceeds in an aqueous solution. In some embodiments, the reaction proceeds in a non-aqueous solution. Suitable solvents include for example polar protic solvent or polar aprotic solvent. Examples of polar protic solvent include water, methanol, ethanol, propanol and any combination thereof. Examples of polar aprotic solvent include DMF, DMSO, THF, dioxane, NMP and any combination thereof.

In some embodiments, the oxidizing agent is $H_2O_2$. In some embodiments, after oxidizing I-C to introduce two Ys as OH, one of the two OH is coupled to $CH_3COOH$,

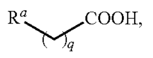

or the corresponding acid anhydride, wherein q is an integer from 1 to 6 inclusive, $R^a$ represents $C_{1-4}$alkyl, OH, SH, $NH_2$, COOH, amino acids, CN, an alkyne-containing group, $N_3$, $(OCH_2CH_2)_rOC_{1-4}$alkyl or $(NHCH_2CH_2)_rNHC_{1-4}$alkyl, wherein r is an integer from 1 to 4 inclusive. A coupling agent is generally present for the reaction with an acid. Nonlimiting examples of coupling agents include dicyclohexylcarbodiimide (DCC), BOP, PyBOP, and HBTU. Suitable solvents include DMF, DMSO and other polar nonprotic solvents.

In some embodiments, the oxidizing agent is tert-butyl peroxide and the reaction proceeds in the presence of $CH_3COOH$,

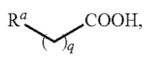

or the corresponding acid anhydride, and wherein one of the two Ys is OH and the other Y is acetate or

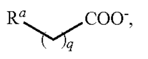

Other substituents are as described above. Suitable solvents include DMF, DMSO and other polar nonprotic solvents. In some embodiments, the reaction proceeds at room temperature.

Another aspect of the patent document provides a method of synthesizing a compound of Formula I-B. The substituents of Formula I-B are defined as follows:

Formula I-B

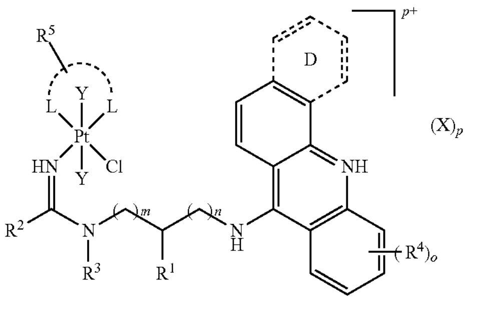

each L independently represents monodentate $NH_3$ or an amine ligand wherein the nitrogen coordinates to Pt, further wherein the two amine ligands optionally link up to form a diamine ligand (chelate);

X represents nitrate or halide;

each Y independently represents a halide;

o is 0, 1, 2 or 3;

p is 1 or 2;

m is 0, 1, 2 or 3;

n is 0, 1, 2 or 3;

$R^1$, $R^2$ and $R^3$ each independently represents a $C_{1-10}$ alkyl, wherein one or more carbons of the $C_{1-10}$ alkyl is optionally (a) replaced with a moiety selected from the group consisting of amino, oxygen, sulfur, amide, ester, carbamate, sulfonamide, sulfonyl, carbonate, ketone, and disulfide; or (b) substituted with a moiety selected from the group consisting of hydroxy, imino, oxo, cyano, $C_{1-10}$ alkoxy, $C_{1-10}$ alkylthio, $C_{1-6}$ alkylsulfonyl, and di-$C_{1-10}$ alkylamine;

Wherein optionally, (i) $R^1$ and $R^3$ link up to form a 4 to 8 membered ring; or (ii) $R^2$ and $R^3$ link up to form a 5 to 8 membered ring;

$R^4$ is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, or (mono-, di-, or trihalogeno)methyl;

$R^5$ represents an optional substituent of L and is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, (mono-, di-, or trihalogeno) methyl, or $C_{1-10}$ alkoxy;

D represents an optional aromatic ring (e.g. phenyl ring fused to acridine ring).

The method includes treating an intermediate of Formula I-C with an oxidizing agent. The substituents of Formula I-C are the same as defined for Formula I-B except the absence of Y in I-C. In some embodiments, each Y is chloride.

In some embodiments, the oxidizing agent is PhICl2, and the reaction proceeds at a temperature below 20° C., below 10° C., below 5° C., below 0° C., below −5° C., below −10° C., below −20° C., below −40° C., below −60° C., or below −70° C. In some embodiments, the reaction proceeds in a non-aqueous solution. Suitable solvents include for example polar protic solvent or polar aprotic solvent. Examples of polar protic solvent include methanol, ethanol, propanol and any combination thereof. Examples of polar aprotic solvent include DMF, DMSO, THF, dioxane, NMP and any combination thereof. In some embodiments, the reaction proceeds at a temperature below −70° C. in methanol.

Synthesis of compounds of Formula II-B

The compound of Formula II-B can be prepared in one or more steps from intermediates IV and V. The substituents of IV and V-1 are the same as defined in II-B. Each substituent of a formula in each instance can be different from that of another formula as long as the scope of the substituent is within the definition. For instance, p in Formula IV is 1 and X can be chloride or nitrate depending on the stage of the reaction. Formula V-1 can be in the form of an acid salt (e.g. 2HCl). Ligand Y can be introduced as described above.

In some exemplary embodiment, the counter ion of Formula IV is replaced from chloride to nitrate via the reaction with $AgNO_3$ in an organic solvent. After filtration of AgCl, reaction with V-1 leads to an adduct, which after treatment with an acid provides compound of II-B with two counter anions.

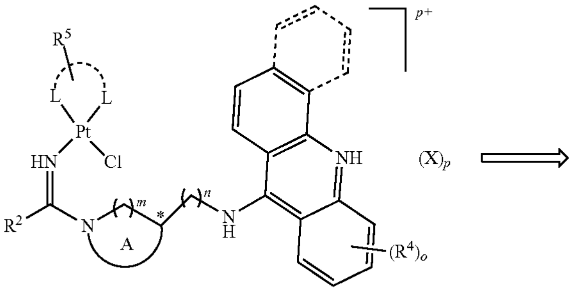

II-B

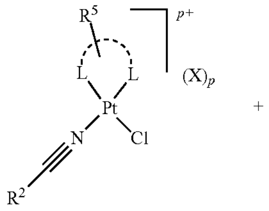

IV

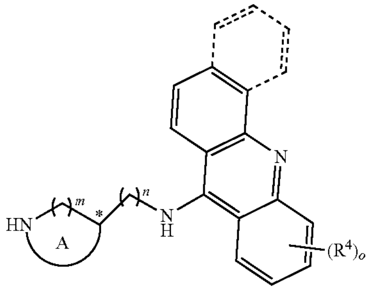

V-1

Formula V-1 can be derived from the reaction between V-2 and V-3. For instance, heating V-2 and V-3 in an organic solvent followed by removal of Boc protecting group will lead to V-1.

2 HX

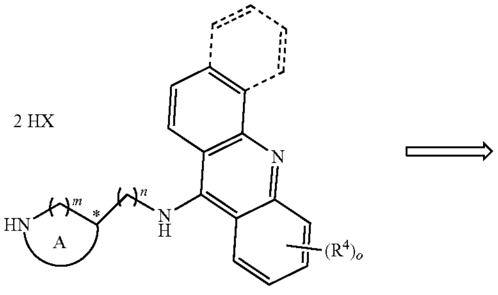

V-2

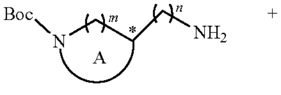

V-3

-continued

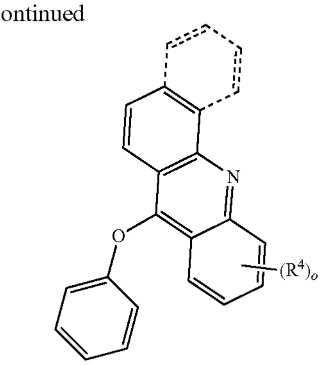

V-1

Synthesis of compounds of Formula III-B

Compounds of Formula III-B can be prepared from intermediates VI and VII-1. VI may go through a ligand exchange reaction to replace one of the chlorides before reacting with VII-1. The resulting product can be further treated with an acid (e.g. $HNO_3$) to introduce an additional counter anion (e.g. increasing p from 1 to 2). Ligand Y can be introduced as described above.

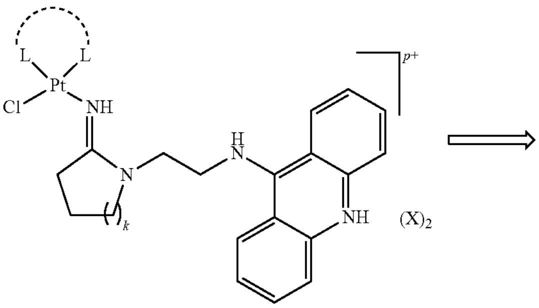

III-B

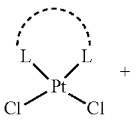

VI

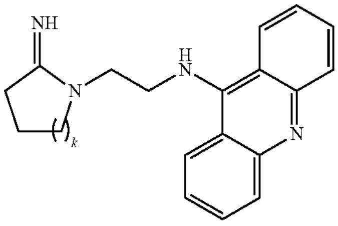

VII-1

The compound of Formula VII-1 can be prepared from VII-2 and VII-3. The compound of VII-3 may be in its acid salt form. VII-3 can be derived from VII-4 and VII-5 through addition reaction followed by removal of Boc protecting group.

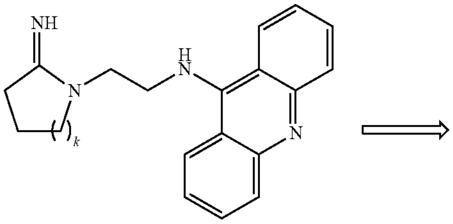

VII-1

-continued

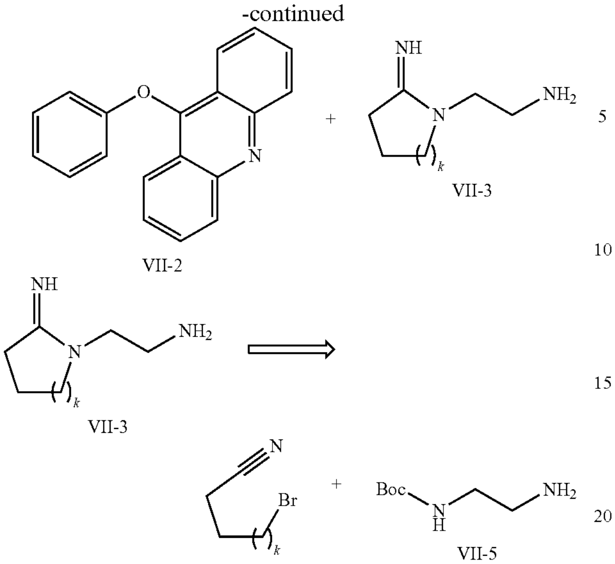

VII-2 VII-3

VII-3

VII-4 VII-5

Isomers of particular configuration (R or S) can be prepared by using starting materials (e.g. V-2) of the corresponding steric configuration. Alternatively, the stereoisomer can be obtained by chiral chromatography separation of a mixture of stereoisomers.

Pharmaceutical Composition

Another aspect of this patent document provides a pharmaceutical composition of any compound disclosed herein. The pharmaceutical composition contains one or more physiologically acceptable carriers.

Non-limiting examples of carriers include physiologically acceptable surface-active agents, glidants, plasticizers, diluents, excipients, smoothing agents, suspension agents, film forming substances, and coating assistants. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents. Suitable exemplary binders include crystalline cellulose, sucrose, D-mannitol, dextrin, hydroxypropylcellulose, hydroxypropylmethylcellulose, polyvinylpyrrolidone, and the like. Suitable exemplary disintegrants include starch, carboxymethylcellulose, calcium carboxymethylcellulose, croscarmellose sodium, sodium carboxymethylstarch, and the like. Suitable exemplary solvents or dispersion media include water, alcohol (for example, ethanol), polyol (for example, glycerol, propylene glycol, and polyethylene glycol, sesame oil, corn oil, and the like), and suitable mixtures thereof that are physiologically compatible. Suitable exemplary solubilizing agents include polyethylene glycol, propylene glycol, D-mannitol, benzylbenzoate, ethanol, trisaminomethane, cholesterol, triethanolamine, sodium carbonate, sodium citrate, and the like. Suitable exemplary suspending agents include surfactants such as stearyltriethanolamine, sodium laurylsulfate, laurylaminopropionic acid, lecithin, benzalkonium chloride, benzethonium chloride, glycerin monostearate, coconut oil, olive oil, sesame oil, peanut oil, soya and the like; and hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose, and the like. Suitable exemplary isotonic agent includes sodium chloride, glycerin, D-mannose, and the like. Suitable exemplary buffer agents include buffer solutions of salts, such as phosphate, acetates, carbonates, and citrates. Suitable exemplary soothing agents include benzyl alcohol, and the like. Suitable exemplary antiseptic substances include para-oxybenzoic acid esters, chlorobutanol, benzyl alcohol, phenethyl alcohol, dehydroacetic acid, sorbic acid, and the like. Suitable exemplary antioxidants include sulfite salts, ascorbic acid, and the like. Suitable exemplary sealers include, but are not limited to HPMC (or hypromellose), HPC, PEG and combinations thereof. Suitable exemplary lubricants include magnesium stearate, calcium stearate, talc, colloidal silica, hardened oil and the like.

In further exemplary embodiments for solid preparations, carriers or excipients include diluents, lubricants, binders, and disintegrants. In exemplary embodiments for liquid preparations, carriers include solvents, solubilizing agents, suspending agents, isotonic agents, buffer agents, soothing agents, and the like. Acceptable additional carriers or diluents for therapeutic use and the general procedures for the preparation of pharmaceutical compositions are well known in the pharmaceutical art, and are described, for example, in Remington's Pharmaceutical Sciences, 18th Ed., Mack Publishing Co., Easton, PA (1990), which is incorporated herein by reference in its entirety.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

Method of Cancer Treatment

Another aspect of the patent document provides methods of cancer treatment using the compounds disclosed herein. These compounds bind to DNA by a mechanism that involves intercalation and platination nucleobase nitrogen, a more severe form of DNA damage than the cross-links observed for cisplatin. On a per-adduct basis, the hybrid agents are more potent inhibitors of DNA synthesis than cisplatin, which induce replication fork arrest and a high level of DNA double-strand breaks requiring specialized DNA repair modules. They are also more efficient inhibitors of RNA polymerase II (Pol II) and have been demonstrated to target the cell's nucleoli, the sites of ribosomal DNA (rDNA) transcription. These mechanisms most likely contribute to the high cytotoxicity of compounds such as platinum-acridines. The results from mechanistic studies in cell-free systems, human cancer cells, and chemical genomic fitness profiling in *S. Cerevisiae* are consistent with nuclear DNA as the principal target of these agents, which suggests that these compounds overcome chemoresistance to cisplatin at the DNA level. Most compellingly, the compounds such as platinum-acridines maintain up to 1000-fold higher activity than cisplatin in notoriously DNA repair-proficient NSCLC, even though the hybrid adducts are repaired more rapidly than the classical cross-links in these cells.

The platinum-based compounds disclosed herein exhibit potent activities against various cancers including for example mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and biliary duct), primary or secondary central nervous system tumors, primary or secondary brain tumors, Hodgkin's disease, chronic or acute leukemias, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non-Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, and retinoblastoma.

In some embodiments, the cancer to be treated with the compound disclosed herein is metastatic cancer. In some embodiments, the cancer has developed resistance to a conventional anti-cancer agent (e.g. secondary agents disclosed herein). In some embodiments, the cancer has developed resistance to conventional platinum agent (e.g. cisplatin).

In some embodiments, the cancer naturally expresses high levels of hMATE1 (SLC47A1). Non-limiting examples of such cancer include non-small cell lung cancers, renal cell carcinoma, melanoma, glioblastoma, pancreatic cancer, hepatocellular carcinoma, and breast cancer.

In some embodiments, the cancer has hMATE1 expression that is epigenetically repressed or the cancer has high stem cell population. Non-limiting examples of such cancer include small-cell lung cancer (SCLC), hematological cancers (AML, ALL, CML, CLL, multiple myeloma), mesothelioma, colorectal cancers, esophageal/stomach cancer, and ovarian cancer.

Cancer Treatment with a Compound of Formula I

In some embodiments, the method including administering to a subject in need thereof a therapeutically effective amount of a compound of Formula I. The substituents and various sub-embodiments of Formula I are as described above.

In some embodiments of any methods disclosed herein, the cancer that can be treated with compounds disclosed herein include non-small cell lung cancer (NSCLC), renal cell carcinoma (RCC), melanoma, glioblastoma, pancreatic cancer, hepatocellular carcinoma, breast cancer, small-cell lung cancer (SCLC), hematological cancers (AML, ALL, CML, CLL, multiple myeloma), mesothelioma, colorectal cancer, esophageal/stomach cancer, ovarian cancer, and endometrial cancer. In some embodiments, these cancers may have epigenetically repressed hMATE1 expression.

In some embodiments of any methods disclosed herein, there is included a step of determining expression of MATE1 in the cancer tissue. In some embodiments, the cancer tissue has been determined as having higher than a normal level prior to administering the compound. In some embodiments, the cancer has been determined to have an elevated level (e.g., the subject has a level higher than a normal level or a reference (such as the level in a sample from a healthy tissue) by more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, more than 100%, more than 150%, more than 200%, more than 300%, more than 400%, more than 500%, or more. In some embodiments, there is included a step of adjusting the dosage or administration schedule of the compound according to the MATE1 level.

In some embodiments of any methods disclosed herein, there is included a step, before, simultaneously with or after administering the compound disclosed here, of administering to the subject an agent to enhance the expression of the MATE1. In some embodiments, the agent is selected from EPZ-6438, EED226, GSK-126, Trichostatin A, SAHA, valproic acid, romidepsin, entinostat, nicotinamide, decitabine, 5-azacytidine, GS-5829, molibresib, and ABBV-075.

In some embodiments of any methods disclosed herein, the cancer tissue has been determined as having epigenetically repressed hMATE1 expression prior to administering the compound. In some embodiments, after the administration of the agent to enhance the expression of the MATE1, the MATE1 level increases, relative to before administering the MATE1 enhancing agent, by more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, more than 95%, more than 100%, more than 150%, more than 200%, more than 300%, more than 400%, more than 500%, or more. In some embodiments, there is included a step of adjusting the dosage or administration schedule of the compound according to the MATE1 level.

In some embodiments of any of the methods disclosed herein, there is included a step of administering to the subject one, two, three or more of the anticancer agents disclosed herein or therapies including chemotherapy, biologics, immunotherapy, HER2 targeted therapy, or curative-intent radiotherapy for the treatment of the cancer.

Cancer treatment with a compound of Formula I'

It is surprisingly discovered that human multidrug and toxin extrusion protein hMATE1 (SLC47A1) is a predictive marker of chemosensitivity to the platinum-acridines compounds and analogs disclosed herein. This epigenetically activatable transporter can thus serve as a target for personalized cancer treatment.

Accordingly, a method of cancer treatment includes (a) obtaining a biological sample from the subject; (b) detecting expression of MATE1 in the biological sample. If the MATE1 exceeds a reference for achieving efficacy, then a compound of Formula I' is administered to the subject.

Formula I' is represented as:

Formula I'

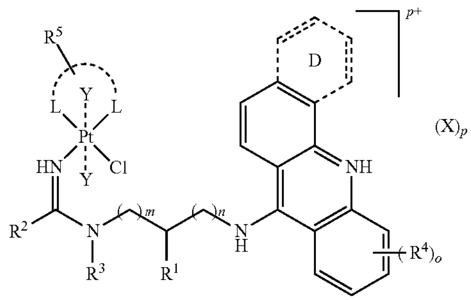

wherein each L independently represents monodentate $NH_3$ or an amine ligand wherein the nitrogen coordinates to Pt, further wherein the two amine ligands optionally link up to form a diamine ligand (chelate);

X represents nitrate or halide;

Each Y independently represents a ligand selected from the group consisting of halide, hydroxide, pseudohalide, acetate, and

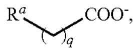

wherein q is an integer from 1 to 6 inclusive, $R^a$ represents OH, SH, $NH_2$, COOH, amino acids, CN, an alkyne-containing group, $N_3$, $(OCH_2CH_2)_rOC_{1-4}$alkyl or $(NHCH_2CH_2)_rNHC_{1-4}$alkyl, wherein r is an integer from 1 to 4 inclusive;

is 0, 1, 2 or 3;

p is 1 or 2;

m is 0, 1, 2 or 3;

n is 0, 1, 2 or 3;

D is an optional aromatic ring;

$R^1$, $R^2$ and $R^3$ each independently represents a $C_{1-10}$ alkyl, wherein one or more carbons of the $C_{1-10}$ alkyl is optionally (a) replaced with a moiety selected from the group consisting of amino, oxygen, sulfur, amide, ester, carbamate, sulfonamide, sulfonyl, carbonate, ketone, and disulfide; or (b) substituted with a moiety selected from the group consisting of hydroxy, imino, oxo, cyano, $C_{1-10}$ alkoxy, $C_{1-10}$ alkylthio, $C_{1-6}$ alkylsulfonyl, and di-$C_{1-10}$ alkylamine;

$R^4$ is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, or (mono-, di-, or trihalogeno)methyl;

$R^5$ represents an optional substituent of L and is selected from the group consisting of halogen, cyano, nitro, $C_{1-10}$ alkylthio, $C_{2-10}$ alkenyl, $C_{2-10}$ alkynyl, $C_{1-10}$ alkoxy, $C_{1-10}$ dialkylamino, $C_{1-10}$ alkyl, (mono-, di-, or trihalogeno)methyl, or $C_{1-10}$ alkoxy.

Various sub-embodiments of Formula I' are the same as that of Formula I. In some embodiments, Formula I' meets one of (i), (ii) and (iii):

(i) $R^1$ and $R^3$ link up to form a 4 to 8 membered ring;

(ii) $R^2$ and $R^3$link up to form a 5 to 8 membered ring; and (iii) at least one of the two Ys is selected from the group consisting of OH, chloride, acetate and

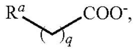

wherein q is an integer from 1 to 6 inclusive, $R^a$ represents OH, SH, $NH_2$, COOH, CN, an alkyne-containing group, $N_3$, $(OCH_2CH_2)_rOC_{1-4}$alkyl or $(NHCH_2CH_2)_rNHC_{1-4}$alkyl, wherein r is an integer from 1 to 4 inclusive.

In some embodiments, the compound is not

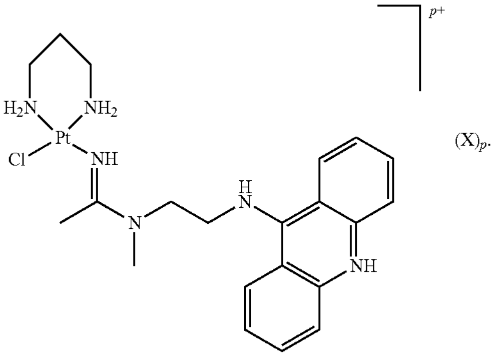

PA-0

Example compounds for treating cancers with elevated expression of MATE1 include the following:

PA-1

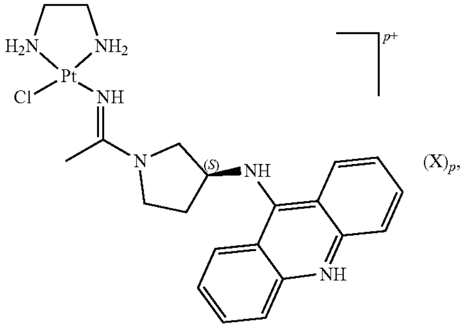

PA-2

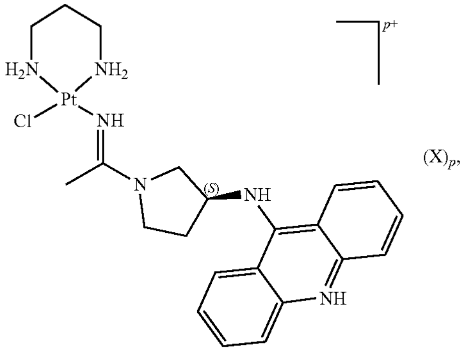

-continued
PA-3
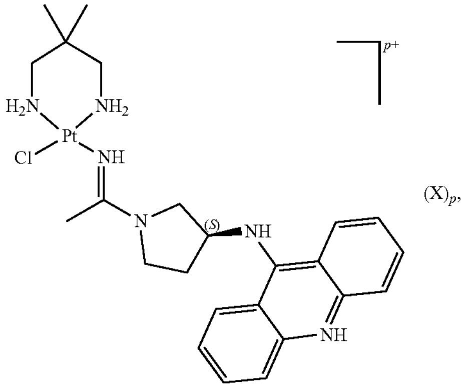
PA-4
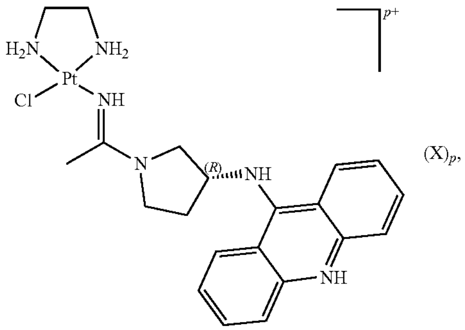
PA-5
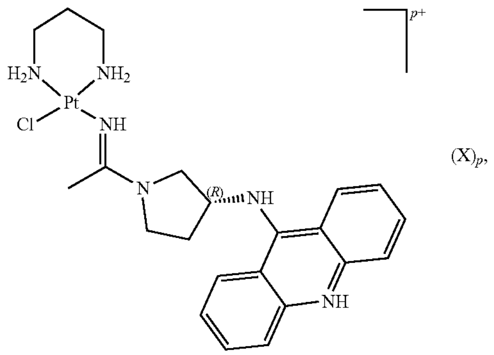
PA-6
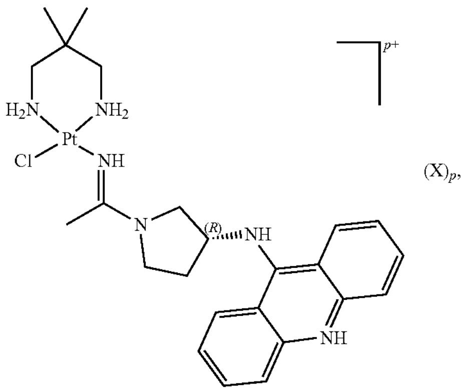
-continued
PA-7
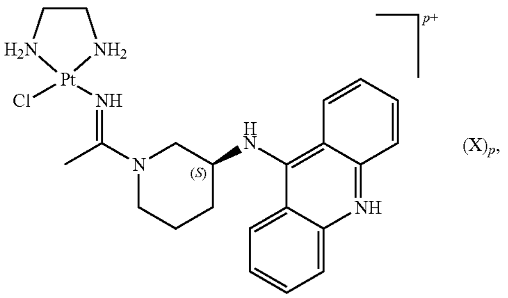
PA-8
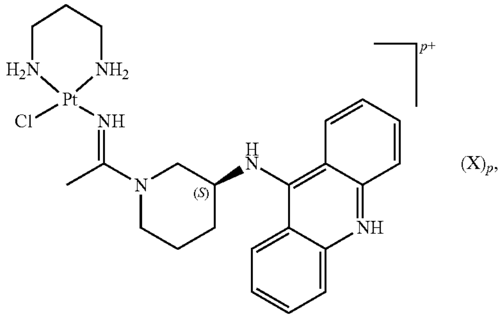
PA-9
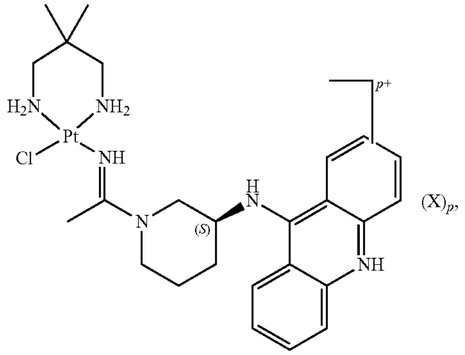
PA-10
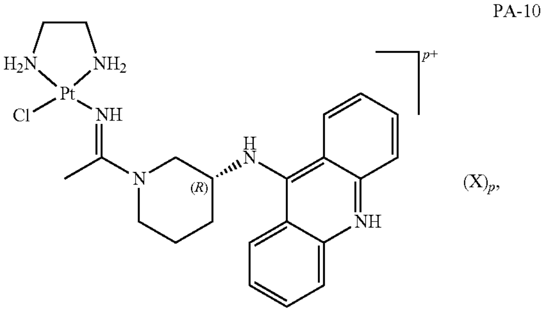
PA-11
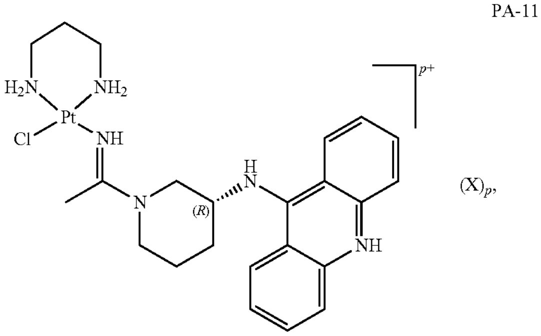

-continued
PA-12
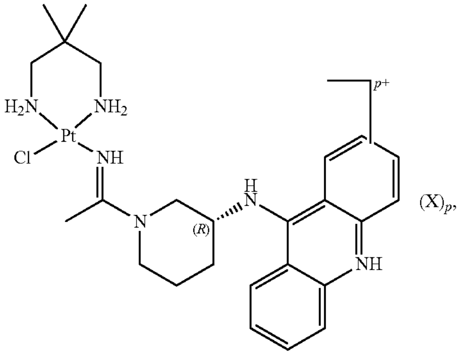
PA-21
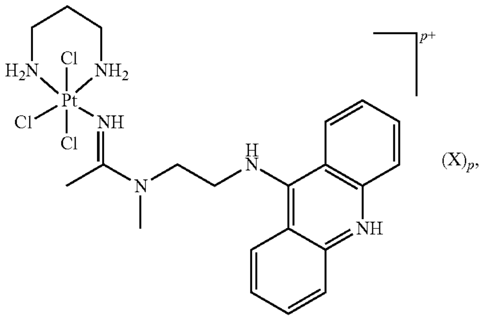
PA-22
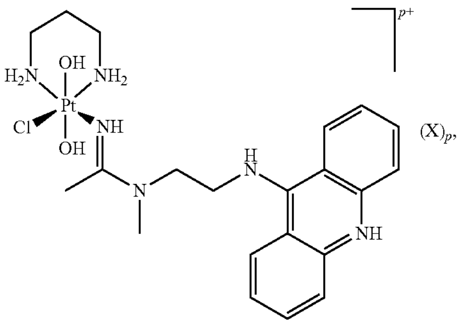
PA-23
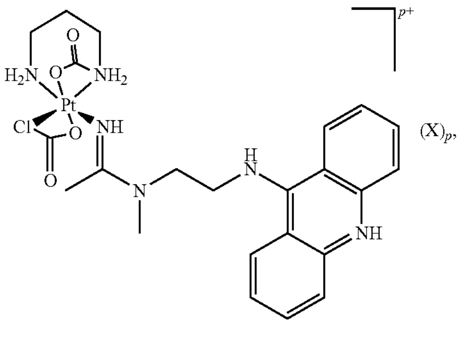
-continued
PA-24
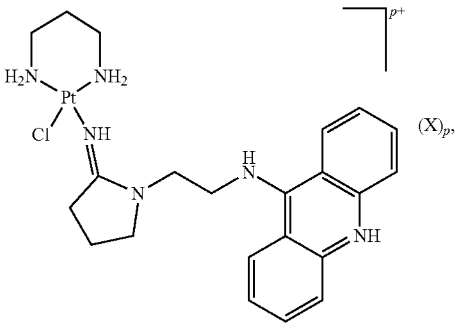
PA-13
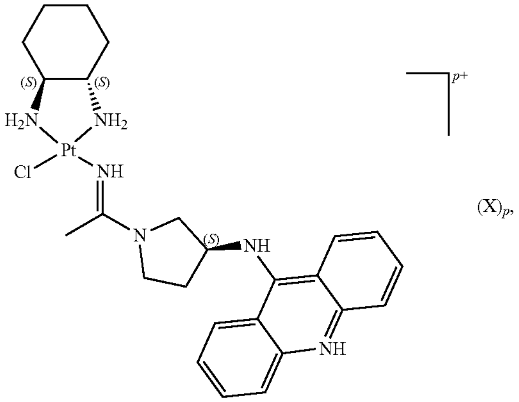
PA-14
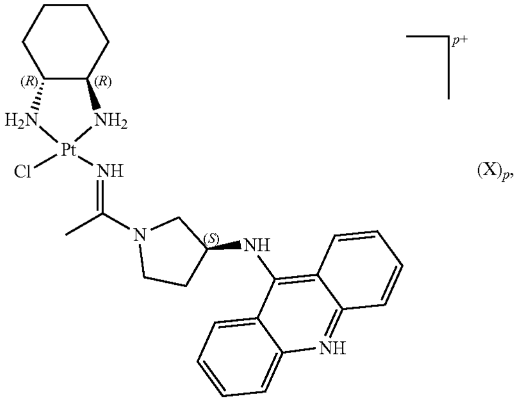
PA-15
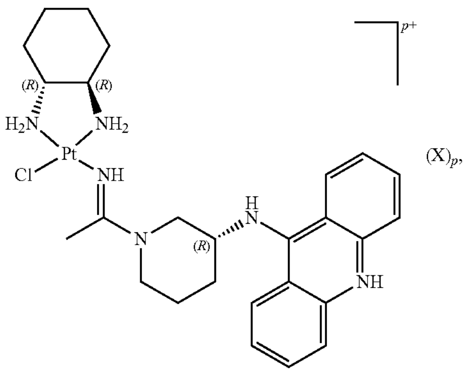

-continued

PA-16

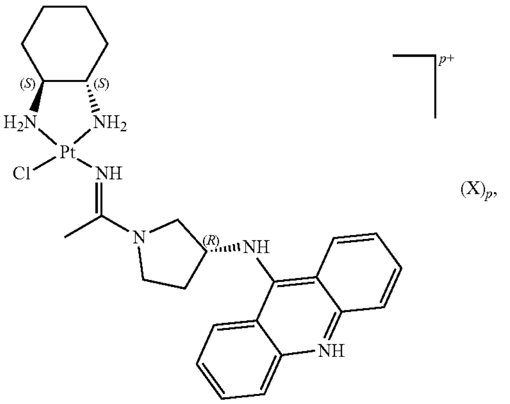

PA-17

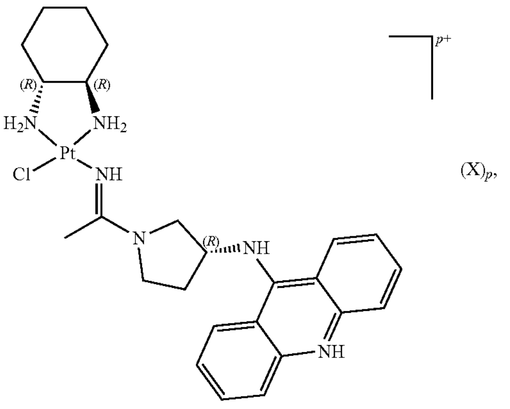

PA-18

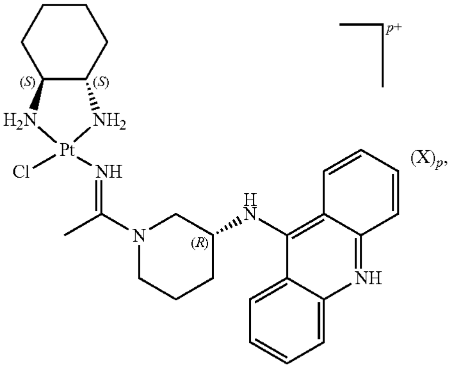

PA-19

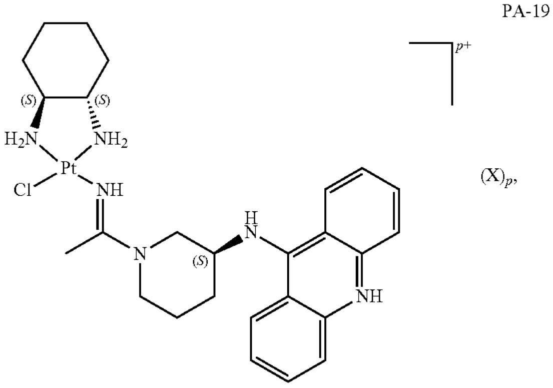

-continued

PA-20

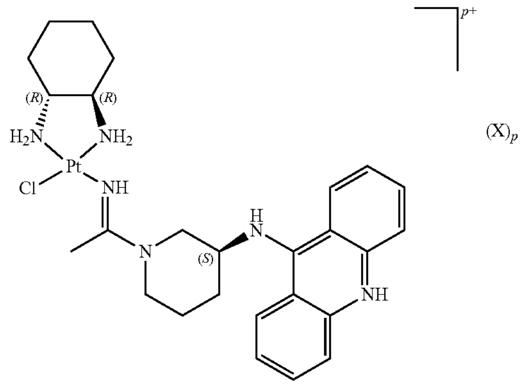

and

PA-0

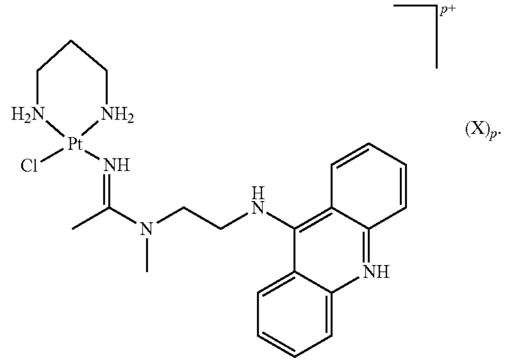

Sample Collection and Detection of MATE1 Expression

In some embodiments, the method includes screening the subject in need of treatment and determining the expression of MATE1, the level of which is a biomarker for the efficacy of the platinum-acridines or analogs thereof. In some embodiments, the MATE1 is human MATE1 (hMATE1). In some embodiments, the MATE1 has least 50%, 55%, 60%, 65%, 70%, 75%, 80%, 85%, 90%, 91%, 92%, 93%, 94%, 95%, 96%, 97%, 98%, 99% or most preferably 100% sequence identity or similarity with a wild type (NCBI Reference Sequence: NP_060712.2; SEQ No. 1), or encoded by a nucleotide sequence having at least 90% sequence identity with SLC47A1 (mRNA, NCBI Reference Sequence: NM_018242.3; SEQ No. 2).

The sample to be analyzed can be any bodily tissue or fluid that includes nucleic acids from the cancer in the subject. In certain embodiments, the sample will be a blood sample comprising circulating tumor cells or cell free DNA. In other embodiments, the sample can be a tissue, such as a lung tissue. The tissue can be from a tumor tissue and may be fresh frozen or formalin-fixed, paraffin-embedded (FFPE). In certain embodiments, a tumor FFPE sample is obtained.

Samples that are suitable for use in the methods described herein contain genetic material, e.g., genomic DNA (gDNA). Genomic DNA is typically extracted from biological samples such as blood or mucosal scrapings of the lining of the mouth, but can be extracted from other biological samples including urine, tumor, or expectorant. The sample itself will typically include nucleated cells (e.g., blood or buccal cells) or tissue removed from the subject including normal or tumor tissue. Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

In some cases, a biological sample may be processed for DNA isolation. For example, DNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al. (2003). The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAamp® Tissue Kit (Qiagen, Chatsworth, Calif.) and the Wizard® Genomic DNA purification kit (Promega). Non-limiting examples of sources of samples include urine, blood, and tissue.

The level of MATE1 expression, as described herein can be determined using methods known in the art. For example, gel electrophoresis, capillary electrophoresis, size exclusion chromatography, sequencing, and/or arrays can be used to detect the presence or absence of insertion mutations.

A reference or standard or range thereof for the level MATE1 expression can be determined through in vitro and in vivo experiments. Such a reference or range correlates with a desirable efficacy for a platinum-acridine or analog thereof for the treatment of a particular cancer. By comparing the detected the MATE1 level in a subject against the reference, the prognosis of the treatment with the compound of Formula I' can be reasonably predicted. In some embodiments, the MATE1 level is projected to be sufficient for the treatment of a cancer (e.g. slowing down the progress of the cancer or improving the survival rate or enhancing objective response rate) with the compound of Formula I', then the compound is administered to the subject.

In some embodiments, the MATE1 level is determined to be insufficient for the administration of the compound of Formula I'. The method thus provide a useful guidance on whether or not to proceed with the treatment.

In some embodiments, a sensitizing agent is administered to the subject in order to enhance the expression of the MATE1 when the detected level is insufficient. In some embodiments, the sensitizing agent improves the expression of MATE1 by at least 2%, at least 5%, at least 10%, at least 15%, at least 20%, at least 30%, at least 40%, or at least 50% after being administered to the subject. Once the expression reaches a desirable level or a reference, the compound of Formula I' is administered. Even when the detected MATE1 reaches or exceeds reaches a desirable level or a reference, a sensitizing agent can be administered to further enhance the therapeutic effect of the compound of Formula I'.

In some embodiments, MATE1 is detected to be over-expressed without the sensitizing agent and therefore the compound of Formula I' is administered. In some embodiments, the sensitizing agent is administered until MATE1 is over-expressed before the administration of the compound of Formula I'. As used herein, "over-expressed" or "over-expression" indicates that the protein is expressed at a higher level than normal cells. The expression level can be measured using immunohistochemistry, fluorescence in situ hybridization (FISH), or chromogenic in situ hybridization (CISH).

Any agent that epigenetically enhances the expression of SLC47A1 gene can be employed in the method described herein. Nonlimiting examples include inhibitors of proteins of polycomb repressive complex 2 (PRC2), such as EZH2 and EED, histone deacetylases (HDAC), DNA methyltransferase 1 (DNMT1), and BET bromodomain proteins. In some embodiments, the sensitizing agent is EPZ-6438 (tazemetostat), GSK-126, or EED226. In additional embodiments, the sensitizing agent is Trichostatin A, SAHA (vorinostat), valproic acid, romidepsin, entinostat, nicotinamide. In additional embodiments, the sensitizer is decitabine (5-aza-dC) or 5-azacytidine (5-aza-C). In additional embodiments, the sensitizer is GS-5829, molibresib, or ABBV-075. One or more sensitizing agents against the same or different targets can be used in combination to enhance the level of MATE1.

In exemplary embodiments for detection and quantification of hMATE1/SLC47A1 in human biopsy specimens, immunohistochemistry (IHC) or RNA expression profiling can be used to (i) determine the level of hMATE1/SLC47A1 expression in tumor biopsies, (ii) identify hMATE1-positive cancers for proposed treatment with platinum-acridines in treatment-naïve patients and patients previously treated with chemotherapy, and (iii) monitor changes in hMATE1/SLC47A1 expression levels after treatment with other anticancer agents and/or pre-exposure epigenetic drugs. Applications under (iii) include (A) measuring differential expression of hMATE1 after epigenetic repression of hMATE1 and other epigenetically regulated genes (e. g., tumor suppressors) as a form of acquired resistance to previously administered oncology drugs, and (B) measuring differential expression of hMATE1 after pre-treatment of patient with epigenetic drugs to enhance hMATE1 expression in never-treated tumors or restore hMATE1 expression due to the adverse effects of prior treatments.

IHC of formalin-fixed and paraffin-embedded biopsied tissues relies on visual scoring or computer-aided analysis of digitized images after detection of membrane and cytoplasmic hMATE1 protein using appropriate polyclonal anti-MATE1 antibodies for IHC/IHC-p: e.g. LSBio: aa492-519; Thermo Fisher: PAS-545442, PAS-25272; abcam: ab224440. Scoring schemes include counting % positive cells and determining H scores (H core=0-300=[1×(% cells 1+)+2×(% cells 2+)+3×(% cells 3+)], where 1+, 2+, and 3+ refer to weakly, moderately, and strongly stained, respectively) based on the staining intensity of a secondary color-producing reaction or immunofluorescence. The tissue samples are then categorized as "hMATE1-positive" or "hMATE1-negative" on the basis of a tissue-specific discretionary threshold. Alternatively, annotations of normal and cancer tissue can be performed using fixed guidelines for classification of immunohistochemical results (The Human Protein Atlas; proteinatlas.org). Basic annotation parameters include an evaluation of i) staining intensity (negative, weak, moderate or strong), ii) fraction of stained cells (<25%, 25-75% or >75%) and iii) subcellular localization (nuclear and/or cytoplasmic/membranous).

RNA expression profiling by reverse transcription quantitative polymer chain reaction (RT-qPCR) involves the following steps: (i) extraction of total RNA from homogenized tissue samples using the appropriate RNeasy Qiagen Kit; (ii) determination of RNA purity by absorbance ratio $A_{260}/A_{280}$; (iii) confirmation of RNA integrity by agarose gel electrophoresis; (iv) conversion of RNA into cDNA using a reverse transcription kit; (v) PCR amplification using PCR master mix and the appropriate primers for SLC47A1 and appropriate housekeeping genes (controls); (vi) normalization of data as ratios of SLC47A1 and housekeeping genes e.g., GAPDH). Changes in SLC47A1 expression (e.g., due to acquired resistance or upon treatment with epigenetic drug) are monitored by the comparative threshold cycle (Ct) method (deltaCt, 2^deltaCt).

Administration Regimen

The compound or of a pharmaceutically composition thereof disclosed herein for cancer treatment may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; as well as (d) administration topically; as deemed appropriate by those of skill in the art for bringing the active compound into contact with living tissue.

Advantageously, the compound or a pharmaceutically composition thereof for administrations described herein are prepared into dosage forms in a unit dose suited to fit a dose of the active ingredients. Such dosage forms in a unit dose include, for example, tablets, pills, capsules, injections (ampoules), suppositories, etc.

In exemplary embodiments of the compound or a pharmaceutically composition thereof for oral administration, the composition can be a tablet, coated tablet, capsule, caplet, cachet, lozenges, gel capsule, hard gelatin capsule, soft gelatin capsule, troche, dragee, dispersion, powder, granule, pill, liquid, an aqueous or non-aqueous liquid suspension, an oil-in-liquid or oil-in-water emulsion, including sustained release formulations that are known in the art. For pediatric and geriatric applications, suspensions, syrups and chewable tablets are especially suitable.

The therapeutically effective amount of the compound or of a pharmaceutically composition thereof required as a dose will depend on the route of administration, the type of subject, including human, being treated, and the physical characteristics of the specific subject under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively, dosages may be based and calculated upon the surface area of the patient, as understood by those of skill in the art.

The exact formulation, route of administration and dosage for the compound or of a pharmaceutically composition thereof s can be chosen by the individual physician in view of the patient's condition. (see e.g., Fingl et al. 1975, in "The Pharmacological Basis of Therapeutics", which is hereby incorporated herein by reference in its entirety, with particular reference to Ch. 1, p. 1). In some embodiments, the dose range of compound or of a pharmaceutically composition thereof administered to the subject or patient can be from about 0.5 to about 1000 mg/kg of the patient's body weight. The dosage may be a single one or a series of two or more given in the course of one or more days, as is needed by the patient. In instances where human dosages for compounds have been established for at least some conditions, those same dosages, or dosages that are about 0.1% to about 500%, more preferably about 25% to about 250% of the established human dosage may be used.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of the active ingredient, preferably about 1 mg to about 500 mg, e.g. 5 to 200 mg. In other embodiments, an intravenous, subcutaneous, or intramuscular dose of the active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free acid. In some embodiments, the composition is administered 1 to 4 times per day. Alternatively, the compound or of a pharmaceutically composition thereof may be administered by continuous intravenous infusion, preferably at a dose of up to about 1000 mg per day. As will be understood by those of skill in the art, in certain situations it may be necessary to administer a compound or a pharmaceutical composition thereof herein in amounts that exceed, or even far exceed, the above-stated, preferred dosage range in order to effectively and aggressively treat particularly aggressive diseases or infections. In some embodiments, the compound or of a pharmaceutically composition thereof will be administered for a period of continuous therapy, for example for a week or more, or for months or years.

In some embodiments, the compound or of a pharmaceutically composition thereof is formulated into a dosage form for release for a period of 1 to 12, typically 3 to 12 hours, more typically 6-12 hours after administration. In some embodiments, the oral pharmaceutical compositions described herein may be administered in single or divided doses, from one to four times a day. The oral dosage forms may be conveniently presented in unit dosage forms and prepared by any methods well known in the art of pharmacy.

The compound or of a pharmaceutically composition thereof can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans Alternatively, the toxicity in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans Secondary Agent In any of the methods or kit described herein, the administration or inclusion of a secondary agent having a cytotoxic effect on a cancer cell is contemplated. A cytotoxic effect refers to the depletion, elimination and/or the killing of target cells (i.e., tumor cells). The cytotoxic agent may be at least one selected from the group consisting of an antimetabolite, a mitotic inhibitor, an alkylating agent, an antibody-based EGFR inhibitor, an antibody based HER2/3 inhibitor, an angiogenesis inhibitor, a mTOR inhibitor, a CDK4 and CDK6 inhibitor or an aromatase inhibitor. The combination may include at least two cytotoxic agents. For example, the combination may include at least 2, at least 3, or at least 4 selected from the group consisting of an antimetabolite, a mitotic inhibitor, an alkylating agent, an angiogenesis inhibitor, or all of them.

The antimetabolite may be a drug that inhibits DNA synthesis in cells by suppressing formation of purines or pyrimidines, which are bases of a nucleotide. In one embodiment, the antimetabolite may be selected from the group consisting of Capecitabine, 5-Fluorouracil, Gemcitabine, Pemetrexed, Methotrexate, 6-Mercaptopurine, Cladribine, Cytarabine, Doxifludine, Floxuridine, Fludarabine, Hydroxycarbamide, decarbazine, hydroxyurea, and asparaginase. In a more specific embodiment, the antimetabolite is a base analog, with the term base analogs herein including nucleotide and nucleoside analogs in addition to purine base analogs such as 5-fluorouracil.

The mitotic inhibitor may be a microtubule-destabilizing agent, a microtubule-stabilizing agent, or a combination thereof. The mitotic inhibitor may be selected from taxanes, vinca alkaloids, epothilone, or a combination thereof. In a specific embodiment, the mitotic inhibitor is a taxane, for example including but not limited to, paclitaxel, docetaxel and cabaitaxel. In another specific embodiment, the mitotic inhibitor is a vinca alkaloid or its derivative, for example including but not limited to, vinblastine, vincristine, vinflunine, vinorelbine, vincaminol, vinburnine, vineridine and vindesine.

The mitotic inhibitor may be selected from BT-062, HMN-214, eribulin mesylate, vindesine, EC-1069, EC-1456, EC-531, vintafolide, 2-methoxyestradiol, GTx-230, trastuzumab emtansine (T-DM1), crolibulin, D1302A-maytansinoid conjugates IMGN-529, lorvotuzumab mertansine, SAR-3419, SAR-566658, IMP-03138, topotecan/vincristine combinations, BPH-8, fosbretabulin tromethamine, estramustine phosphate sodium, vincristine, vinflunine, vinorelbine, RX-21101, cabazitaxel, STA-9584, vinblastine, epothilone A, patupilone, ixabepilone, Epothilone D, paclitaxel, docetaxel, DJ-927, discodermolide, eleutherobin, and pharmaceutically acceptable salts thereof or combinations thereof.

As used herein, an "alkylating agent" is a substance that adds one or more alkyl groups ($C_nH_m$, where n and m are integers) to a nucleic acid. In the present invention, an alkylating agent is selected from the group consisting of nitrogen mustards, nitrosoureas, alkyl sulfonates, triazines, ethylenimines, and combinations thereof. Non-limiting examples of nitrogen mustards include mechlorethamine, chlorambucil, cyclophosphamide, bendamustine, ifosfamide, melphalan, melphalan flufenamide, and pharmaceutically acceptable salts thereof. Non-limiting examples of nitrosoureas include streptozocin, carmustine, lomustine, and pharmaceutically acceptable salts thereof. Non-limiting examples of alkyl sulfonates include busulfan and pharmaceutically acceptable salts thereof. Non-limiting examples of triazines include dacarbazine, temozolomide, and pharmaceutically acceptable salts thereof. Non-limiting examples of ethylenimines include thiotepa, altretamine, and pharmaceutically acceptable salts thereof. Other alkylating agents include ProLindac™, Ac-225 BC-8, ALF-2111, trofosfamide, MDX-1203, thioureidobutyronitrile, mitobronitol, mitolactol, nimustine, glufosfamide, HuMax-TAC and PBD ADC combinations, BP-C1, treosulfan, nifurtimox, improsulfan tosilate, ranimustine, ND-01, HH-1, 22P1G cells and ifosfamide combinations, estramustine phosphate, prednimustine, lurbinectedin, trabectedin, altreatamine, SGN-CD33A, fotemustine, nedaplatin, heptaplatin, apaziquone, SG-2000, TLK-58747, laromustine, procarbazine, and pharmaceutically acceptable salts thereof.

The angiogenesis inhibitors are substances that inhibits the growth of new blood vessels (angiogenesis). Some angiogenesis inhibitors are endogenous and a normal part of the body's control and others are obtained exogenously through pharmaceutical drugs or diet. In at least one embodiment, the angiogenesis inhibitors include bevcizumab, sunitinib, sorafenib or pazopatinib.

The secondary agent can also be a molecularly targeted agent may be selected from epidermal growth factor receptor family inhibitors (EGFRi), mammalian target of rapamycin (mTOR) inhibitors, immune checkpoint inhibitors, anaplastic lymphoma kinase (ALK) inhibitors, B-cell lymphoma-2 (BCL-2) inhibitors, B-Raf inhibitors, cyclin-dependent kinase inhibitors (CDKi), such as the CDK4/CDK6 inhibitor, palbociclib, ERK inhibitors, histone deacetylase inhibitors (HDACi), heat shock protein-90 inhibitors (HSP90i), Janus kinase inhibitors, mitogen activated protein kinase (MAPK) inhibitors, MEK inhibitors, such as the MEK1/MEK2 inhibitor trametinib, poly ADP ribose polymerase (PARP) inhibitors, phosphoinositide 3-kinase inhibitors (PI3Ki), Ras inhibitors, sodium-glucose linked transporter (SGLT) inhibitors and combinations thereof.

Non-limiting examples of checkpoint inhibitors include those that target PD-1, PD-L1, CTLA4 and TIGIT (T cell immunoglobulin and ITIM domain). Further examples include Ipilimumab (Yervoy®; blocking a checkpoint protein called CTLA-4); pembrolizumab (Keytruda®), Cemiplimab (Libtayo) and nivolumab (Opdivo®) (targeting another checkpoint protein called PD-1); atezolizumab (Tecentriq®), Avelumab (Bavencio), and Durvalumab (Imfinzi) (targeting PD-L1); MK-7684, Etigilimab/OMP-313 M32, Tiragolumab/MTIG7192A/RG-6058, BMS-986207, AB-154 and ASP-8374 (targeting TIGIT), and V-domain Ig suppressor of T cell activation (VISTA).

The molecularly targeted agent may be selected from ado-trastuzumab emtansine (T-DM1), alemtuzumab, cetuximab, ipilimumab, ofatumumab, panitumumab, pertuzumab, rituximab, tositumomab, 131I-tositumomab, trastuzumab, brentuximab vedotin, denileukin diftitox, ibritumomab tiuxetan, axitinib, bortezomib, bosutinib, cabozantinib, crizotinib, carfilzomib, dasatinib, erlotinib, gefitinib, imatinib mesylate, lapatinib, nilotinib, pazopanib, ponatinib, regorafenib, ruxolitinib, sorafenib, sunitinib, tofacitinib, vandetanib, vemurafenib, alitretinoin, bexarotene, everolimus, romidepsin, temsirolimus, tretinoin, vorinostat, and pharmaceutically acceptable salts thereof or combinations thereof. The molecularly targeted agent may include an antibody or an antibody moiety or an antibody-drug conjugate.

The EGFR inhibitors may be selected from erlotinib, gefitinib, lapatinib, canetinib, pelitinib, neratinib, (R,E)-N-(7-chloro-1-(1-(4-(dimethylamino)but-2-enoyl)azepan-3-yl)-1H-benzo[d]imidazol-2-yl)-2-methylisonicotinamide, Trastuzumab, Margetuximab, panitumumab, matuzumab, necitumumab, pertuzumab, nimotuzumab, zalutumumab, cetuximab, icotinib, afatinib, and pharmaceutically acceptable salt thereof. In one embodiment the EGFR inhibitor may be an antibody based EGFR inhibitor such as cetuximab and in another embodiment, it is necitumumab and yet in another embodiment it is pantitumumab. The molecularly targeted agent may be an anti-EGFR family antibody or a complex including the anti-EGFR family antibody. The anti-EGFR family antibody may be an anti-HER1 antibody, an anti-HER2 antibody, or an anti-HER4 antibody.

Further examples of agent for chemotherapy include SHP2 inhibitors (e.g. RMC-4550 and RMC-4630), phosphatase inhibitors (e.g. Tautomycin), CDK 4/6 inhibitors (abemaciclib (Lilly), palbociclib (Pfizer)), protein-protein interaction disruptors (BI 1701963), HSP90 inhibitor, tubulin inhibitor, apoptosis inhibitor, chemopreventative agent, and therapies targeting PBK/AKT/mTOR pathway.

Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. Another example is Trastuzumab duocarmazine. There are currently more than 30 ADC drug candidates in various stages of clinical trials for cancer treatment. As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

Kit

Another aspect of the patent document provides a kit, which includes the compounds disclosed herein or a pharmaceutically acceptable salt thereof, or a pharmaceutical composition thereof and an instruction for treating cancer. In some embodiments, the kit further includes a secondary agent descried herein. In some embodiments, the components may be provided in a form which is suitable for sequential, separate and/or simultaneous administration.

In some embodiments, the kit also includes assays and/or equipments for detecting the expression of MATE1. In some embodiments, the kit includes the sensitizing agent described above.

The kit can also be provided with instruction, such as dosage and administration instructions. Such dosage and administration instructions can be of the kind that is provided to a doctor, for example by a drug product label, or they can be of the kind that is provided by a doctor, such as instructions to a patient.

The compound or of a pharmaceutically composition thereof may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions or kits comprising the compound or of a pharmaceutically composition thereof formulated in a compatible pharmaceutical carrier may also be prepared, placed in an appropriate container, and labeled for treatment of an indicated condition.

The compounds and methods described in this patent document are further illustrated by the examples below. These examples serve only to illustrate the invention and should not be interpreted as limiting the scope of the invention in any way, since further modifications encompassed by the disclosed invention will be apparent to those skilled in the art. All such modifications are deemed to be within the scope of the invention as defined in the present specification and claims.

EXAMPLES

Study of Compound Activities and Mechanism

Using the 60-cell line screen maintained by the Developmental Therapeutics Program of the National Cancer Institute (NCI-60) in combination with the COMPARE analysis tools, the biological activity of compound 1 and to mechanistic differences from clinically relevant oncology drugs were studied. Compound 1 was screened twice in a library of 59 cell lines from nine different tissues of origin, including hematological cancers and solid tumors. Among the 10 cell lines most sensitive to compound 1 (50% growth inhibition end point: log $GI_{50}$<−7.75, which corresponds to $GI_{50}$<18 nM) are NCI-H460, NCI-H226, NCI-H522, and A549 (all NSCLC), SF-295 (glioblastoma), SN12C (renal cell carcinoma), SK-MEL-5 and UACC-62 (both melanoma), DU-145 (prostate), and T-47D (triple-negative breast cancer), representing cancer models from six different tissues of origin and of varying oncogene and tumor suppressor status (Table 1). In six of these cell lines (incl. 3 NSCLC), compound 1 resulted in 50% growth inhibition at single-digit nanomolar concentrations (log $GI_{50}<-8$). Compound 1 showed approximately two orders of magnitude higher activity across the entire spectrum of cell lines than cisplatin to result in an average growth inhibition similar to that achieved by doxorubicin and topotecan, two oncology drugs also acting through DNA damage-mediated mechanisms. While the two topoisomerase poisons kill cancer cells at similar inhibitory concentrations as compound 1, they do not show the cell line-specific cytotoxic enhancement of our hybrid agent, which is most notable in NSCLC. Of the four agents in comparison, compound 1 shows the widest range of activity from low nanomolar to micromolar $GI_{50}$ values with a more than 2000-fold difference between the most sensitive and the most resistant cell lines ($\Delta\log GI_{50}>3.3$).

TABLE 1

Ten NCI-60 cell lines most sensitive to compound 1 and their genetic backgrounds

| Tissue of Origin | Cell Line | $log_{10}GI_{50}$ | Mutated Cancer Genes CDKN2A | TP53 | PTEN | RB1 | PIK3CA | KRAS | BRAF |
|---|---|---|---|---|---|---|---|---|---|
| Lung | NCI-H460 | <−8.00 | ■ | | | | ▲ | ■ | |
| | NCI-H226 | <−8.00 | ■ | | | | | | |
| | NCI-H522 | −7.92 | | ■ | | | | | |
| | A549 | <−8.00 | ■ | | | | | ■ | |
| CNS | SF-295 | −7.88 | ■ | ■ | ■ | | | | |
| Renal | SN12C | <−8.00 | | ■ | | | | | |
| Melanoma | SK-MEL-5 | −7.75 | ■ | | | | | | ▲ |
| | UACC-62 | <−8.00 | ■ | | ■ | | | | ■ |
| Prostate | DU-145 | <−8.00 | ■ | ▲ | | ■ | | | |
| Breast | T-47D | −7.83 | | ■ | | | ▲ | | |

■ Homozygous mutation/deletion

▲ Heterozygous mutation/deletion

Using the COMPARE algorithm in conjunction with Pearson correlation analysis, NCI database for test compounds that resulted in NCI-60 activity patterns similar to that of compound 1 was analyzed. The results demonstrate that the mechanism of compound 1 is unique among DNA-targeted cytotoxic drugs and other classes of cancer chemotherapeutics ($R<0.5$) (Table 2). Of the approved oncology drugs tested in NCI-60, transcription inhibitors and topoisomerase poisons revealed the greatest similarity with compound 1. Importantly, cisplatin and oxaliplatin were among the drugs that showed the lowest level of correlation. These results suggest that our hybrid molecule and the traditional platinum-based drugs may not share any relevant mechanistic features except their proven ability to form adducts with nuclear DNA. This raises the question as to whether the unique activity profile of compound 1 might be associated with specific molecular targets or gene expression patterns in cancer cells. In these cases, correlations were based on analysis of alternative concentration ranges for test compounds.

The chemosensitivity of cancer cells from various tissues of origin to compound 1 is highly positively correlated with hMATE1 (SLC47A1) expression. To gain insight into the factors driving the unique activity profile of compound 1, a comparative analysis of cell growth inhibition data and global gene expression in NCI-60 cell lines was performed, based on gene transcript (mRNA) levels determined on multiple microarray platforms, which are available as part of the COMPARE tools. COMPARE analysis yielded 806 unique genes correlated positively, and 849 genes correlated negatively ($p<0.05$) with the growth inhibition of compound 1 ($GI_{50}$ end point) across the entire range of cell lines. The strongest relationship at an unusual high level of positive correlation was observed for the gene SLC47A1 ($R=0.69$, $p<10^{-5}$), which encodes a member of the solute carrier (SLC) family of proteins: human multidrug and toxin extrusion protein 1, hMATE1. When total growth inhibition ($GI_{100}$, TGI) was selected as the endpoint, an even higher level of correlation was observed ($R=0.79$). hMATE1, a 13-helix transmembrane protein, shows high expression levels in normal liver and renal tissue, where it serves as a proton-coupled antiporter (see Twelve transmembrane helices form the functional core of mammalian MATE1 (multidrug and toxin extruder 1) protein. J Biol Chem 2012, 287 (33), 27971-82; MATE1 has an external COOH terminus, consistent with a 13-helix topology. Am J Physiol Renal Physiol 2009, 297 (2), F263-71; and Structural basis for the drug extrusion mechanism by a MATE multidrug transporter. Nature 2013, 496 (7444), 247-51, the entire of disclosure of these references are hereby incorporated by reference). Its major function is the ATP-independent excretion of organic cations across apical membranes into the bile and urine, which renders hMATE1 an important modulator of drug response, drug toxicity, and drug-drug interactions. Aberrantly high expression of hMATE1 is also found in cancerous tissues.

TABLE 2

COMPARE analysis of chemosensitivity profiles for compound 1 and selected anticancer drugs

| Test compound | DNA damage | Mechanism | Pearson's R |
|---|---|---|---|
| Compound 1 | Pt-IC hybrid | Inhibitor of DNA synthesis and transcription | 1 |
| Mitomycin C | Alk, XL | Inhibitor of rRNA synthesis | 0.499* |
| Doxorubicin | IC | Topo II poison, oxidative stress | 0.449 |
| Topotecan | IC | Topo I poison | 0.344 |
| Actinomycin D | IC | Transcription inhibitor | 0.286 |

TABLE 2-continued

COMPARE analysis of chemosensitivity profiles for compound 1 and selected anticancer drugs

| Test compound | DNA damage | Mechanism | Pearson's R |
|---|---|---|---|
| Bleomycin | SC | $O_2$-dependent DNA double-strand breaks | 0.221* |
| Erlotinib | N/A | Protein kinase inhibitor | 0.187 |
| Gemcitabine HCl | N/A | Inhibitor of DNA synthesis | 0.18 |
| Rapamycin | N/A | Inhibitor of mTOR-mediated growth signaling | 0.123 |
| Paclitaxel (Taxol) | N/A | Microtubule-targeted mitotic inhibitor | 0.123* |
| Cisplatin | Pt, XL | Transcription inhibitor | 0.116 |
| Vinblastine Sulfate | N/A | Microtubule-targeted mitotic inhibitor | 0.099* |
| Oxaliplatin | Pt, XL | Inhibitor of replication and transcription, non-DNA damage mediated mechanisms | 0.015 |

Abbreviations:
Pt, platinating agent;
XL, cross-linker;
IC, intercalator;
Alk, alkylating agent.
SC, strand cutter.
Asterisks indicate drugs for which no five-dose NCI-60 data were available in the concentration range $-8 < \log[\text{drug}] < -4$ (used for screening compound 1).

The chemosensitivity of cancer cells from various tissues of origin to compound 1 is highly positively correlated with hMATE1 (SLC47A1) expression. To gain insight into the factors driving the unique activity profile of compound 1, a comparative analysis of cell growth inhibition data and global gene expression in NCI-60 cell lines was performed, based on gene transcript (mRNA) levels determined on multiple microarray platforms, which are available as part of the COMPARE tools. COMPARE analysis yielded 806 unique genes correlated positively, and 849 genes correlated negatively ($p<0.05$) with the growth inhibition of compound 1 (GIs( )end point) across the entire range of cell lines. The strongest relationship at an unusual high level of positive correlation was observed for the gene SLC47A1 (R=0.69, $p<10^{-5}$), which encodes a member of the solute carrier (SLC) family of proteins: human multidrug and toxin extrusion protein 1, hMATE1. When total growth inhibition ($GI_{100}$, TGI) was selected as the endpoint, an even higher level of correlation was observed (R=0.79). hMATE1, a 13-helix transmembrane protein, shows high expression levels in normal liver and renal tissue, where it serves as a proton-coupled antiporter. Its major function is the ATP-independent excretion of organic cations across apical membranes into the bile and urine, which renders hMATE1 an important modulator of drug response, drug toxicity, and drug-drug interactions. Aberrantly high expression of hMATE1 is also found in cancerous tissues.

The above analysis is consistent with a mechanism by which MATE promotes uptake of compound 1 into cancer cells rather than acting as an efflux pump, which would cause a more resistant phenotype and would have resulted in a negative correlation. A comparison of the NCI-60 screening results for compound 1 with the hMATE1 (SLC47A1) expression profile supports the findings of the COMPARE analysis and illustrates the extent to which the transport protein dominates chemosensitivity. With a few exceptions, cell lines expressing high levels of hMATE1 (based on transcript levels) are generally exquisitely sensitive to compound 1, while the opposite is true for cell lines expressing low levels of the transporter (visually compare, e.g., the activity/expression profiles for NSCLC (LC) and melanoma (ME) cell lines). For example, compound 1 performs poorly relative to other DNA-targeted drugs (e. g., doxorubicin and topotecan) across all leukemia cell lines, which invariably show low hMATE1 expression. In cell lines representing solid tumors, a greater cell line-dependent variability exists. For instance, in the two prostate cancer cell lines tested, PC-3 ($GI_{50}\approx5$ μM, low hMATE1 expression) and DU-145 ($GI_{50}<10$ nM, high hMATE1 expression), compound 1 shows a more than 500-fold difference in growth inhibition, which is not observed for any other oncology drug in NCI-60. Likewise, the renal carcinoma cell line, SN12C, which shows the highest level of hMATE1 (SLC47A1) expression of all NCI-60 cell lines, most likely due to a gene copy number alteration (amplification) was also the most sensitive to compound 1.

SLC47A1 is not the only solute carrier gene whose expression showed a positive correlation with growth inhibition in NCI-60, but only SLC47A1 correlated at such a high level ($p<10^{-5}$ vs. $p<0.01$ for all other SLC genes; see Table 3), suggesting a specific and dominant role of this transporter in the mechanism of compound 1. When calculating overlaps between the >800 genes that were positively correlated with the activity of compound 1 and gene ontology (GO) gene sets maintained by the Molecular Signatures Database (MSigDB), GO terms such as plasma membrane function and components, and intracellular transport ranked highest. This is in stark contrast to doxorubicin and topotecan, which showed the greatest overlap with GO sets annotated chromatin, DNA damage recognition and repair, and chromosome organization (data not shown), as would be expected for a DNA damaging agent. These observations underpin the notion that, contrary to our expectation, the chemosensitivity of cancer cells to compound 1 is not controlled at the genome level, but by the transportome. This led us to the hypothesize that efficient cellular uptake via selective hMATE1-mediated transport across the plasma membrane ultimately determines the sensitivity of cancer cells to the hybrid agent.

TABLE 3

NCI-60/COMPARE analysis: Summary of SLC genes whose mRNA expression is positively or negatively correlated with chemosensitivity to compound 1 ($\log GI_{50}$)

| Gene | Pearson's R[a] | Function | P value[b] |
|---|---|---|---|
| SLC11A2 | 0.328 | $H^+$-coupled Cu and $M^{2+}$ symporter | * |
| SLC12A4 | 0.352 | $K^+/Cl^-$ coupled transporter | ** |
| SLC16A1 | 0.327 | lactate/pyruvate transporter | * |
| SLC16A4 | 0.358 | monocarboxylic acid transporter | ** |
| SLC17A9 | −0.366 | ATP/mononucleotide vesicular uptake | ** |
| SLC22A17 | 0.374 | multi-specific cation transporter (brain) | ** |
| SLC22A5 | 0.38 | carnitine transporter | ** |
| SLC22A7 | −0.397 | multi-specific anion transporter | ** |
| SLC24A2 | −0.427 | $Ca^{2+}$/cation antiporter | *** |
| SLC25A32 | −0.318 | mitochondrial folate transporter | * |
| SLC26A8 | −0.36 | anion transporter | ** |
| SLC27A7 | −0.352 | fatty acid transporter | ** |
| SLC2A9 | −0.374 | uric acid transporter GLUT9 | ** |
| SLC30A1 | 0.371 | cation transporter | ** |
| SLC30A5 | 0.404 | $Zn^{2+}$ transporter | ** |
| SLC35E3 | 0.419 | putative transporter | ** |
| SLC35F6 | 0.353 | carbohydrate/$H^+$ symporter | ** |
| SLC38A7 | 0.362 | $Na^+$ coupled amino acid transporter | ** |
| SLC39A8 | 0.381 | $Zn^{2+}$ and $Cd^{2+}$ transporter | ** |
| SLC3A2 | 0.392 | amino acid transporter | ** |
| SLC41A3 | −0.318 | cation transporter | * |
| SLC43A3 | −0.415 | putative transporter | ** |
| SLC47A1 | 0.692 | $H^+$-coupled organic cation antiporter | ***** |
| SLC48A1 | 0.38 | heme transporter | ** |

TABLE 3-continued

NCI-60/COMPARE analysis: Summary of SLC genes whose mRNA expression is positively or negatively correlated with chemosensitivity to compound 1 ($logGI_{50}$)

| Gene | Pearson's R[a] | Function | P value[b] |
|---|---|---|---|
| SLC51B | 0.393 | bile acid transporter | ** |
| SLC6A19 | −0.38 | $Na^+$ dependent neutral amino acid transporter | ** |
| SLC6A2 | 0.371 | $Na^+$/neurotransmitter symporter | ** |
| SLC7A11 | 0.328 | anionic amino acid transporter | * |
| SLC8A1 | 0.364 | $Na^+$/$Ca^{2+}$ exchanger | ** |
| SLCO4A1 | −0.328 | organic anion transporter | * |

[a]N = 58.

[b]* P < 0.05;  P < 0.01; * P < 0.001; ***** P < 0.00001.

Pyrimethamine, a selective hMATE1 inhibitor, effectively blocks cellular accumulation of compound 1 and quenches its cytotoxicity in A549 cells.

While the results from the combined cell line screening and transcriptomics are highly suggestive of a functional role of hMATE1 protein in the mechanism of compound 1, experimental validation of the gene product is required as statistical correlations do not necessarily indicate an underlying causal relationship. To demonstrate a direct involvement of hMATE1 protein as a mediator of chemosensitivity, we first performed a transporter inhibition assay in A549 human lung adenocarcinoma cells. A549 expresses high levels of hMATE1 (SLC47A1) (The Human Genome Database), which we confirmed by Western blot analysis. Unsurprisingly, the cell line proved to be highly sensitive to compound 1 both in the NCI-60 screen ($GI_{50}$<10 nM) and in previous colorimetric cell proliferation assays ($IC_{50}$=3.9 nM). Prior to treatment with compound 1, cultured A549 cells were pre-treated with the antimalarial drug pyrimethamine, a potent and selective inhibitor of hMATE1 (reported $K_i$ values: 77-93 nM). Since the assay required co-incubation of compound 1 and PM, we first confirmed that no undesired reactivity exists between the two agents. Taking advantage of the fluorescent properties of the 9-aminoacridine chromophore in compound 1, confocal fluorescence microscopy was initially used to quantify the accumulation of the hybrid agent. When A549 cells were pre-treated with PM, followed by a 4-hour exposure to compound 1, confocal images showed a reduction of intracellular blue fluorescence by 60% relative to cells not treated with PM. These results suggest that hMATE1-mediated transport across the plasma membrane is involved in the cellular uptake of compound 1.

Because the microscopy experiments were performed at relatively high concentrations of platinum-acridine and PM (10 μM), contributions from non-specific transport by other membrane proteins cannot be completely ruled out under these conditions. To overcome this drawback, we took advantage of the parts-per-trillion-level limit of detection of inductively coupled plasma mass spectrometry (ICP-MS) and also quantified uptake of compound 1 from cellular platinum levels under therapeutically more relevant conditions. When cells were pre-incubated with 100 nM PM, to avoid non-specific inhibition of other organic cation transporters, and subsequently treated with 100 nM compound 1, corresponding to the compound's $IC_{90}$ in A549, a decrease of uptake by 85% was observed. Together, these findings corroborate that compound 1 is selectively transported across the plasma membrane by hMATE1.

Finally, we performed a colorimetric cell proliferation assay to determine if blocking hMATE1 by PM had an effect on the cytotoxicity of compound 1 toward A549 cells. Exposure to 100 nM compound 1 for 72 hours causes a robust cell kill with less than 10% of the cells surviving treatment. When A549 cells were pre-treated with PM at concentrations that did not compromise cell viability, a pronounced cytoprotective effect was observed. PM at a concentration of 10 nM was able to significantly (p<0.01) increase the population of viable cells to 20%, while 100 nM inhibitor resulted in 90% survival (p<0.0001) of cells treated with compound 1. The level of protection achieved at the latter concentration of PM correlates well with the reduced (85%) platinum levels determined by ICP-MS, providing additional support for the notion that hMATE1-mediated transport is the key to compound 1's high potency.

Gene knockdown by RNA interference (RNAi) validates the role of hMATE1 protein in the mechanism of compound 1. Ultimate evidence for a direct role of hMATE1 transporter in promoting the cellular accumulation and cytotoxicity of compound 1 came from gene knockdown experiments using RNAi interference. Using transfection of appropriate siRNAs, we were able to generate a A549 model in which hMATE1 was transiently reduced by 40-50% relative to scrambled control, which is consistent with reported knockdown efficiencies achieved for the SLC47A1 gene in this cells line using RNAi. Knockdown was confirmed by Western blot analysis and immunofluorescence staining of transfected cells. Cellular uptake of compound 1 was studied under the same conditions as in the transporter inhibition assay using PM. In hMATE1 knockdown cells, accumulation of platinum was significantly (p=0.0091) reduced by 50% relative to control cells transfected with a scrambled RNA sequence. We then designed a 96-well plate assay that allowed us to assess the performance of compound 1 in A549 cells after hMATE1 knockdown. After 24 hours of continuous treatment, the dose- and time-dependent cytotoxicity of compound 1 was reduced in A549 cells at concentrations of 100 nM and 1 μM by 12% and 35%, respectively. At the higher concentration, the level of protection persists after 48 hours of treatment, which resulted in a 36% higher survival of hMATE1-silenced cells compared to mock-treated cells. These results unequivocally confirm that hMATE1 protein plays a direct role in the mechanism of compound 1 by mediating its cellular uptake, which ultimately controls the chemosensitivity of the lung cancer cell line.

Correlation and gene set overlap analysis suggest that hMATE1 expression is epigenetically regulated in many types of cancer. SN12C renal carcinoma cells show the greatest copy number alteration (CNA, 4.75 copies) and the highest transcript level for the SLC47A1 gene. Across the entire range of cell lines, SLC47A1 gene copy number and transcript levels are positively correlated with Pearson's R=0.398 and p<0.01, suggesting that genetic alterations contribute to differential hMATE1 expression. Closer analysis of the NCI CellMiner database reveals that epigenetic modifications are also a major regulator of hMATE1 (SLC47A1) expression. This reasoning is based on correlations observed between SLC47A1 transcript levels and DNA methylation status (CpG islands, CGI) of the gene (p<0.001), as well as correlations with epigenetic repressors of gene expression, such as DNA methyltransferase I (DNMT1) and the histone methyltransferase, enhancer of zeste homolog 2 (EZH2). Analysis of an extended set of 963 cell lines in the Genomics of Drug Sensitivity in Cancer database (GDSC, Sanger Institute) shows that SLC47A1 expression is strongly negatively correlated with CGI methylation (Pearson's R=−0.32, $p=4.9\times10^{-25}$), which corroborates the above findings (Table 4). A recent study demonstrates that hMATE1 (SLC47A1) expression in normal liver tissue is attenuated epigenetically by promoter hypermethylation, which supports these observations.

TABLE 4

Summary of significant ($p < 0.05$) correlations identified between CPI methylation status and expression levels of the SLC47A1 gene in 963 cancer cell lines[a] of different tissues of origin and cell types

| Cell Line Origin | Pearson's R | P value |
|---|---|---|
| Multiple Myeloma | −0.55 | 0.028 |
| Colon | −0.33 | 0.025 |
| Esophagus/Stomach | −0.41 | $7.6 \times 10^{-4}$ |
| Liver | −0.56 | 0.02 |
| Lung | −0.32 | $8.2 \times 10^{-6}$ |
| NSCLC | −0.43 | $1.1 \times 10^{-5}$ |
| Lung Adenocarcinoma | −0.47 | $4.7 \times 10^{-4}$ |
| Ovaries | −0.32 | 0.032 |
| Pancreas | −0.47 | $8.1 \times 10^{-3}$ |
| Epithelial | −0.16 | $4.4 \times 10^{-3}$ |
| Epithelial—Mesenchymal | −0.43 | $2.7 \times 10^{-7}$ |
| Mesenchymal | −0.23 | $1.3 \times 10^{-5}$ |

[a]Genomics of Drug Sensitivity in Cancer (GDSC) database (CellMinerCDB, version 1.1, discover.nci.nih.gov/cellminercdb).

A link was discovered between genes whose methylation status is negatively correlated with SLC47A1 transcript levels in NCI-60 (CellMiner), including SLC47A1 itself, and specific MSigDB gene sets (Table 5). Hypergeometric distribution analysis of our unranked list of genes (Supplementary Table S8) showed the highest correlation with genes epigenetically silenced in embryonic stem cells. The process involves EZH2-mediated histone protein H3 trimethylation at lysine 27 (H3K27me3) by the polycomb repressive complex 2 (PRC2) and downstream CGI hypermethylation. These data provide additional clues about hMATE1 (SLC47A1) regulation at the epigenome level and a potential link between hMATE1 expression, cancer sternness, and drug resistance. Taken together, these observations led us to hypothesize that epigenetic drugs reversing the repression of hMATE1 (SLC47A1) should increase the uptake of compound 1 and sensitize resistant cancer cells to this agent.

TABLE 5

Summary of correlations between chemosensitivity, MATE-1 (SLC47A1) expression, and epigenetic factors for compound 1.

| Data in Comparison | | Pearson's R | P value |
|---|---|---|---|
| NCI-60, $logGI_{50}$ | SLC47A1 transcript level | 0.692[a] | <.00001 (*****)[a] |
| NCI-60, $logGI_{50}$ | DNMT1 transcript level | −0.378[a] | 0.0034 (**)[a] |
| SLC47A1 transcript level | SLC47A1 CGI methylation | −0.416[b] | <0.001 (***)[b] |
| SLC47A1 transcript level | SLC47A1 gene copy number | 0.398[b] | <0.001 (***)[b] |
| SLC47A1 transcript level | EZH2 transcript level | −0.289[b] | 0.025 (*)[b] |
| SLC47A1 CGI methylation | DNMT1 transcript level | 0.311[b] | 0.015 (*)[b] |
| EZH2 transcript level | DNMT1 transcript level | 0.479[b] | <0.001 (***)[b] |

[a]NCI COMPARE analysis, n = 58.
[b]NCI CellMiner analysis tool, database version 2.2, n = 60.

Treatment of HCT-116 colon cancer cells with epigenetic drugs activates hMATE1 expression and enhances the cellular uptake and cytotoxicity of compound 1. To test our hypothesis of chemosensitization at the epigenome level we chose a colon cancer cell line as a model. HCT-116 shows low levels of hMATE1 (SLC47A1) and hypermethylation of promoter CGI and proved to be relatively resistant to compound 1 in NCI-60. We first pre-screened several epigenetic drugs in cultured HCT-116 cells in a multi-well plate format for their ability to increase the uptake of compound 1 using confocal fluorescence microscopy. Cells were treated with EPZ-6438 (tazemetostat, a potent inhibitor of EZH2), EED226 (an allosteric inhibitor of PRC2), decitabine (a DNMT1 inhibitor), and valproic acid (a histone deacetylase, HDAC, inhibitor), as well as combinations of these drugs. EZH2 inhibitors, decitabine, and valproic acid have previously been demonstrated to enhance the expression of epigenetically silenced genes in HCT-116, including SLC47A1. EPZ-6438 and EED226, alone or in combination, were the only treatments that resulted in enhanced uptake of compound 1, based on the observation of increased acridine-associated, blue fluorescence, without causing changes in cell morphology and viability. These compounds were then tested again at escalating doses (2.5-20 mM). A combination of EPZ-6438 and EED226 ("E/E") resulted in the most pronounced increase in uptake of compound 1 in a dose-dependent manner Additionally, confocal fluorescence images of representative cells stained with hMATE1 antibody showed a higher level of immunofluorescence compared to the no-treatment control, which was considered preliminary evidence of increased hMATE1 expression.

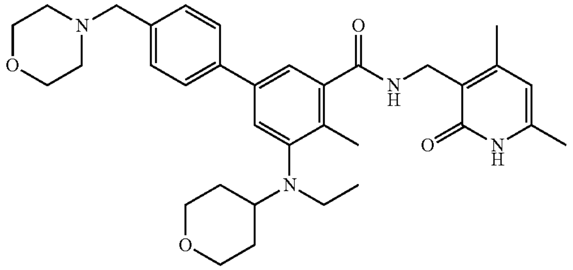

EPZ-6438

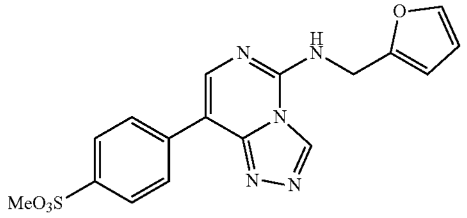

EED226

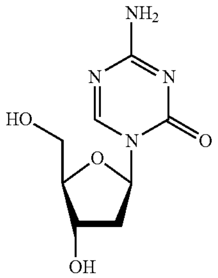

decitabine

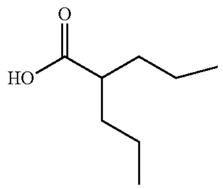

valproic acid

We then used a cell proliferation assay to determine if pre-exposing HCT-116 cells to non-toxic concentrations of EPZ-6438 and EED226 sensitized them to compound 1. At higher concentrations, the epigenetic drugs alone also caused significant changes in the cells' growth characteristics and significant cell death. Because of this limitation, the experiments were performed with 2.5 μM and 5 μM E/E. When cells were treated with 10 μM compound 1, pre-exposure to E/E resulted in a pronounced decrease in cell viability that was dependent on the dose of epigenetic drug. At 5.0 μM E/E, the maximum enhancement in cell growth inhibition relative to unsensitized control was 45%. Under these ad hoc conditions, Western blot analysis of lysates from HCT-116 cells show a 20% and 70% increase in hMATE1 levels relative to control at the lower and the higher concentration, respectively. This observation in conjunction with the confocal microscopy results confirms that hMATE1 protein is the mediator of the chemosensitizing effect. The results of this proof-of-concept experiment demonstrate the feasibility of sensitizing cancer cells to compound 1 using nontoxic epigenetic drugs.

The current study sheds light on the unique mechanism of action of a potent hybrid anticancer agent, which is structurally and functionally distinct from cytotoxic chemotherapies in clinical use. Compound 1 has emerged from a pipeline of platinum-acridine agents that were designed based on the guiding principle that rapid formation of unique DNA adducts would overcome tumor resistance to DNA-targeted drugs, including platinum-based pharmaceuticals. While DNA damage indisputably is the ultimate cause of cancer cell death produced by the hybrid agent, its low-nanomolar activity critically depends on a transport protein, which is an unprecedented feature among cytotoxic drugs in the NCI-60 database. Cancer cells overexpressing hMATE1 protein appear to be highly sensitive to compound 1 regardless of genetic background and phenotypic abnormalities. The membrane transporter controls the pattern of sensitivity with a high level of predictability reminiscent of the selectivity of targeted anticancer therapies. This unexpected feature may translate into new treatment modalities that specifically (i) overcome resistance observed with current cytotoxic drugs, (ii) exploit hMATE1 as a biomarker for personalized therapy, (iii) take advantage of efficient uptake to achieve clinically useful efficacy, and (iv) sensitize cancers to the hybrid agents by priming cancer tissue with epigenetic drugs.

At physiological pH, compound 1 and its derivatives exist as 2+ charged, hydrophilic cations comprising a positively charged platinum(II) moiety and a protonated 9-aminoacridine chromophore ($pK_a$=9-10). In earlier work, we have demonstrated that the most potent platinum-acridines accumulate in NSCLC cells at a 60-100-fold faster rate than cisplatin, which is consistent with efficient, transporter-mediated uptake. The current study confirms this supposition and provides the mechanistic basis of this critical step in the mechanism of platinum-acridines. High intracellular drug concentrations achieved by efficient transmembrane transport may outcompete common resistance mechanisms such as DNA repair and P-glycoprotein 1 (multi-drug resistance protein 1, MDR1, ABCB1)-promoted drug efflux. ABCB1 is the gene most negatively correlated with drug activity for doxorubicin (R=−0.65, NCI-60/COMPARE), which has been validated at the protein level, but it ranks low in the corresponding gene set for compound 1 (Supplementary Table S2). Comparatively fewer examples exist of membrane transporters typically involved in drug elimination that may also enhance drug uptake into tumor tissue. Organic cation transporter 2 (hOCT2, SLC22A2) is an example of such a dual pharmacokinetic role. The major function of basolateral hOCT2-mediated cellular uptake, in concert with apical hMATE1-mediated cellular efflux, is the renal excretion of xenobiotics, including the (cationic) metabolites of platinum drugs. Disruption of this pathway may cause kidney and liver toxicity. On the other hand, hOCTs have also been shown to enhance the cytotoxicity and efficacy of platinum-containing drugs. hOCT proteins, which are overexpressed in colorectal cancer tissue, assist in the cellular uptake of oxaliplatin, which has provided a rationale for the drug's therapeutic use in this form of cancer. It is noteworthy to mention that NCI-60/COMPARE analyses do not show any correlations between expression levels of SLC22A2 gene and oxaliplatin activity. This suggests that hOCT2 may not have the same level of predictive utility for global chemosensitivity to oxaliplatin as hMATE1 has for compound 1. hMATE1 protein, which mediates efflux of substrate from polarized epithelial cells in excretory organs, also transports substrates across the plasma membrane in the opposite direction. Recently, a unique case of sensitization by this membrane transporter has been reported. hMATE1 promotes accumulation of the clinical kinase inhibitor imatinib (Gleevec) in chronic myeloid leukemia (CML) cells, which enhances the drug's potency in this hematological cancer. In the same study, hMATE1 expression levels have been validated as a predictor of interindividual differences in imatinib response and outcome in CML patients.

Compound 1 is the first chemotherapeutic agent for which bioinformatics and high-throughput screening tools have predicted an overexpressed transport protein as a target that confers a high level of chemosensitivity to cancer cells. hMATE1 expression is high in most NSCLC cell lines, which explains why the advantage of platinum-acridines over cisplatin and other cytotoxic agents was first noted in this aggressive type of cancer. The relevance of a potential dual pharmacokinetic role of hMATE1 in the uptake and extrusion of compound 1 remains to be investigated. Membrane transporters that mediate rapid uptake into tumors while also promoting efficient renal clearance may reduce side effects, such as nephrotoxicity, a common limitation of clinical platinum drugs, and ultimately result in a more favorable therapeutic window for systemic treatment. Compound 1 has already demonstrated efficacy in A549 xenograft models in mice, when injected intravenously, both directly and as liposomal formulation. Using a non-optimized dosing schedule, the agent was able to reduce tumor growth by up to 65% with less than 20% weight loss in test animals, which was reversible, and without other signs of systemic toxicity. These results indicate that the cytotoxicity of compound 1 in vitro in this hMATE1 expressing cancer also translates into promising efficacy in vivo.

Finally, we provide preliminary proof-of-concept data to demonstrate that colorectal cancer cells treated with epigenetic drugs can be sensitized to the cytotoxic effects of compound 1 and that the effect is caused by enhanced hMATE1 mediated drug accumulation. A growing body of evidence supports the clinical utility of co-administering cytotoxic drugs with epigenetic drugs, several of which have entered clinical trials as single treatments and combination therapies (clinicaltrials.gov). It has been demonstrated that renal cell carcinoma (RCC) cells can be sensitized to oxaliplatin by pre-treatment with the hypomethylating agent decitabine, which promotes hOCT2 expression and oxaliplatin accumulation. While decitabine in the above study was itself quite cytotoxic and directly contributed to the synergistic RCC cell kill, we were able to achieve sensitization with nontoxic concentrations of the PRC2-directed inhibitors EPZ-6438 and EED226. A compelling case of translatable epigenetic sensitization of a chemoresistant cancer has recently been reported by Gardner et al. for the Schlafen-11 protein (SLFN11), a putative RNA/DNA helicase that acts as a sensor of replicative stress and tumor suppressor. In patient-derived small-cell lung cancer (SCLC) tissue, Schlafen-11, which sensitizes cancer cells to topoisomerase I poisons, was epigenetically silenced. SLFN11 is the gene most positively correlated with $GI_{50}$ values for topotecan and irinotecan (R=0.69) based on NCI-60/COMPARE analysis, which suggests it plays a similar dominant role in sensitizing cancer cells to the topoisomerase I poisons as SLC47A1 does in sensitizing cancer cells to compound 1. The study demonstrates that treatment with epigenetic drugs restores Schlafen-11 levels, which reverses acquired resistance in SCLC and re-sensitizes cells to the drug topotecan. There also appears to be an epigenetic component to hMATE1 (SLC47A1) expression in SCLC (sclccelllines-.cancer.gov). Since topotecan is a substrate of hMATE1, the reported level of sensitization to the topoisomerase I poison in SCLC cell lines after treatment with the EZH2 inhibitor EPZ-6438 may also reflect higher drug accumulation due to increased levels of hMATE1. Using compound 1 as a cytotoxic component in similar combination regimens to treat this highly aggressive form of lung cancer and other major forms of the disease currently not responding optimally to this compound (e.g., leukemias, ovarian cancer), would be an attractive opportunity.

Method and Agents

Cell culture in general. The human cell lines, A549 (adenocarcinomas) and HCT-116 (colorectal carcinoma) were obtained from the American Type Culture Collection (ATCC). A549 cells were cultured in DMEM/F12 (1:1) media (Thermo Fisher, 11330-032) supplemented with 10% FBS (Thermo Fisher), 10% penstrep (Thermo Fisher, 15070-063). HCT-116 cells were cultured in RPMI 1640 (Gibco, A10491-01) with the same additives as above. Cells were incubated at a constant temperature at 37° C. in a humidified atmosphere containing 5% $CO_2$ and were subcultured every 2-3 days to maintain cells in logarithmic growth. All experiment used cells with passage number of times less than 20.

Reagents, siRNA and antibodies. Pyrimethamine was purchased from (Cat. No.). hMATE1 siRNA and scrambled siRNA were purchased from Thermo Fisher. RNAiMAX were purchased from Invitrogen (13778100). Opti-Mem was purchased from Gibco (31985062). Epigenetic drugs, EED226 (HY-101117), Tazemetostat (EPZ-6438) (HY-13803), Valproic acid (HY-10585) and Decitabine (HY-A0004) were purchased from MedChemExpress. Celltiter 96 AQueous MTS Reagent Powder was purchased from Promega (G1112). RIPA buffer was purchased from Thermo Fisher (89901). Protease inhibitors was purchased from Thermo Fisher (87785). BCA Protein Assay Kit was purchased from Thermo Fisher (23227).

The following antibodies were purchased from indicated suppliers and used at indicated concentrations: anti-MATE1 antibody was purchased from Abcam (ab104016), 1:1000 for immunoblotting. GAPDH antibody was purchased from Bethyl (A300-639A-M), 1:1000 for immunoblotting. Goat anti-rabbit IgG-HRP secondary antibody was purchased from Thermo Fisher (G-21234), 1:10,000 for immunoblotting. SLC47A1 Polyclonal Antibody was purchased from Thermo Fisher (PA5-25272), 1:300 for immunofluorescence. Goat anti-Rabbit IgG Alexa Fluor 635 was purchased from Invitrogen (A-31576) 1:400 for immunofluorescence.

Silencer AM16708 slc47a1

```
sense
5'-CCGAGACAUCAUUAAUCUGtt-3'

Antisense
5'-CAGAUUAAUGAUGUCUCGGtc-3'
```

Silencer Select s30533 slc47a1 (Silencer Select siRNA1)

```
Sense
5'-CAAACUUGAUUUCCCAGUAtt-3'

Antisense
5'-UACUGGGAAAUCAAGUUUGcc-3'
```

Silencer Select s30534 (Silencer Select siRNA2)

```
Sense
5'-GAUCGUAACUGGAGUUGCAtt-3'

Antisense
5'-UGCAACUCCAGUUACGAUCtg-3'
```

Scrambled siRNA Control:

Silencer Negative Control #3 siRNA (AM4615)

Silencer Select Negative Control #1 siRNA (4390843)

LC-MS analysis. 20 □M pyrimethamine and compound 1 solutions were prepared in buffer. These solutions were then mixed in a 1:1 ratio and the resulting solution was kept at 37° C. and shaken for 72 hours. The solutions were then equilibrated to remove of buffer salts using Pierce C18 Spin Columns (Thermo Fisher, Cat. No. 89870) according to manufacturer's protocol. The procured solution was prepared in HPLC grade solvent for LC-MS analysis. Data acquired from Bruker Amazon-SL LC-MS system equipped with an electrospray source using an Agilent ZORBAX SB-C18 analytical column (5 mm, 4 6×150 mm, PN 883975-902). This experiment was performed with both PBS and Tris-HCl buffers.

Confocal fluorescence microscopy. Cells were seeded and allowed to attach overnight before any treatment. After cells were treated depend on purposes of different experiments, media was removed and dishes were rinsed 3 times with 1 mL of pre-warmed PBS buffer. Cells were then used fixed with 4% formaldehyde in PBS buffer for 15 minutes. Dishes were then washed an additional 3 times with 1 mL of pre-warmed PBS before imaging. Images were collected using a LSM 880 Confocal Microscope (Carl Zeiss Microscopy) using a 63X/1.4NA Plan-Apochromatic objective. The fluorescence of acridine was excited with a 405 nm (15 mW) laser at 4.4% and collected between 405-481 nm. To allow comparative fluorescence intensity analysis, excitation power, pinhole settings, PMT gain, and offset values across and within imaging sessions for each respective channel were not changed. The intensity of acridine-related fluorescence in treated cells was estimated by drawing a region of interest around each cell. A total of more than 100 individual cells across 3 views of 2 independent experiments were analyzed in this fashion. Zen software 2.5 (blue edition, Carl Zeiss Microscopy GmbH, 2018) was used for image processing. Panels were assembled and annotated without any additional manipulation of images in Adobe Photoshop CC, version 2017.1.1.

For transporter inhibition assay, cells were seeded on into 35 mm poly-D-lysine-coated glass bottom dishes (MatTek Corporation, Ashland, MD) at a density of $10^5$ cells/mL in 2 mL of medium per dish. Two dishes were pre-treated with 10 □M pyrimethamine for 20 minutes. Then all 4 dishes were treated with 10 □M compound 1. After 4 hours incubations, all four dishes were properly washed and fixed for imaging.

Uptake studied by ICPMS. The protocol used in this experiment is modified from previous publication. Briefly, cells were collected into 15 mL conical tube and centrifuged down to cell pellet and remove supernatant. To each tube, 1 mL of milliQ water was added. The pellet was broken down into suspension by pipetting in and out a few times with a micropipettor. The suspension was transferred into a Teflon microwave vessel followed by washing the centrifuge tube with 1 mL of milliQ water for 3 times. To each vessel, 5 mL of deionized water was added, followed by the addition of 0.5 mL concentrated HCl and 0.5 mL of concentrated $HNO_3$ to reach a total volume of 10 mL. Blanks were also prepared that only contained the same ratio of water and acid. All Teflon tubes were assembled into scaffolds and microwaved. Once finished, each solution was transferred to a 50 mL centrifuge tube, Teflon tubes were rinsed three times and the solution was diluted to a final volume of 50 mL and a final acid concentration of 2% v/v.

The 1000-ppm Pt standard was diluted with 2% v/v acid to prepare standard solutions with concentrations of 0 ppt, 20 ppt, 50 ppt, 100 ppt, 200 ppt, 500 ppt (5 mL for each solution). Both standard solutions and samples were subject to injection to Agilent ICP-MS spectrometer. Standard curve was acquired with linear $R^2$ higher than 0.9999 and samples exceeding 500 ppt of concentration were further diluted. An ICP-MS (8800 Triple Quadrupole, Agilent, Tokyo, Japan) equipped with a SPS 4 automatic sampler, a Scott-type double pass spray chamber operated at 2° C., and a Micromist concentric nebulizer was used in all determinations. Helium gas (?99.999% purity, Airgas, Colfax, NC, USA) was used in the ICP-MS's collision/reaction cell to minimize potential spectral interferences while monitoring the isotope 195-Pt. Other relevant instrument operating conditions such as radio frequency applied power, sample depth, carrier gas flow rate, reaction gas flow rate, and the number of sweeps per replicate were 1550 W, 10.0 mm, 1.05 L/min, 4.0 mL/min, and 100, respectively.

For transporter inhibition assay, A549 cells were seeded into six T-25 flasks (Cat. No.) with 2.5 mL of F12K media (Cat. No.) which supplemented with 10% fetal bovine serum (FBS), 10% penstrep (penicillin+streptomycin), and 10% L-glutamine Cells were seeded at a density of 700,000 per flask. Incubate cells overnight to grow and attach. Three flasks of cells were pre-treated with 100 nM PM for 25 minutes, then administer compound 1. solution to all six flasks to reach a final concentration of 100 nM. Cells were incubated for 3 hours. After treatment, medium was aspirated followed by three times wash with fresh media, aspirating after each wash. Then add 2 mL of trypsin to each flask to detach cells. Add addition of 3 mL fresh media to each flask and collect cell suspension into 15 mL conical tubes. Centrifuge the conical tubes at 250 G for 3 minutes to pellet cells. Aspirate out supernatant. Then continue to wash with 3 mL PBS solution. Centrifuge again at 250 G for 3 minutes. Aspirate out PBS. Repeat twice. Then store conical tubes with cell pellets at −80° C. for further ICP-MS analysis.

For A549 knock down study, A549 cells were reverse transfected with siRNA (Silencer Select s30533 slc47a1) or Silencer Select Negative Control #1 siRNA (4390843) for 48 hours and replace with fresh antibiotics free DMEM/F12K medium and continue to incubate for an addition 24 hours. Cells were then incubated with 100 nM of compound 1 at 37° C. for 4 hours. Cells were then washed with same medium and detached with trypsin to centrifuged to pellets. Cells pellets were resuspended and wash with PBS for twice. At last, cell pellets were frozen at −80° C. for further analysis. Every incubation condition was done in triplicate. Samples were further digested, and the signals of Pt were analyzed by Agilent ICP-MS spectrometer with detail procedures described as below.

Cell proliferation assay. The cytotoxicity studies were carried out according to a standard protocol using the Celltiter 96 AQueous MTS Reagent Powder (Promega, Madison, WI). Relative cell viability was determined from the viability of treated and untreated (control) cells. $IC_{50}$ values were calculated from sigmoidal curve fits with non-linear regression (Log(inhibitors) vs. response) in GraphPad Prism 5 (GraphPad Software, La Jolla, CA).

Immunoblotting. Cells were lysed in RIPA buffer (Thermo Fisher, 89901. Contents: 25 mM Tris-HCl pH 7.6, 150 mM NaCl, 1% NP-40, 1% sodium deoxycholate, 0.1% SDS) according to manufacturer's protocol. RIPA buffer was freshly supplemented with protease inhibitors (Thermo Fisher, 87785). Briefly, cells were washed twice with cold PBS buffer then lysed with cold RIPA buffer to each well. Keep on ice for 30 mM, swirling the plate occasionally for uniform spreading. The cell lysates were gathered with a cell scraper and collected into a 15 mL microcentrifuge tube. Cell lysates were further sonicated (20 seconds with 10% pulse, 1 second on and 1 second off) and centrifuged at 14,000×g for 15 minutes at 4° C. Protein concentration was quantified using BCA Protein Assay Kit (Thermo, 23227).

Protein samples were denatured with a Sample buffer (Thermo Fisher, 39001) which supplemented with DTT (50 mM at final concentration) and incubated at 46° C. for 30 min Equal amount of total protein was loaded on each lane and separated by electrophoresis in 4-15% Mini-PROTEAN TGX Precast Protein Gels (bio-rad, 456-1083) in Tris-glycine SDS buffer (Fisher, BP13414) (30 min at 50 V and 30 min at 120V). The proteins were subsequently transferred to the nitrocellulose membrane (advansta, L-08002-010) via wet transfer (2 hours at 100V) (Transfer buffer: 25 mM Tris-base, 190 mM glycine, 20% methanol. Adjust pH to 8.3). Membranes were then blocked in TBST buffer (20 mM Tris, 150 mM NaCl and 0.05% Tween 20. Adjust pH to 7.6) supplemented with 5% non-fat milk at room temperature for one hour. Membranes were incubated with anti-MATE1 antibody (1:1000) (abcam, ab104016) or GAPDH antibody (1:1000) (Bethyl, A300-639A-M) in TBST buffer supplemented with 2% non-fat milk at 4° C. for overnight. Membranes were then washed 4 times 5 minutes each with TBST buffer and incubated with goat anti-rabbit IgG-HRP secondary antibody (1:10,000) in TBST buffer with 2% non-fat milk at room temperature for one hour. Membranes were continuously washed with TBST 4 times 5 minutes and finally incubate with SuperSignal West Pico PLUS Chemiluminescent Substrate (Thermo, 34580) at room temperature for 5 minutes. The proteins were visualized by Amersham Imager 600 (GE Healthcare).

Immunofluorescence. In general, cells were washed with warm PBS solution for three times and fixed with 4% paraformaldehyde for 15 minutes at room temperature. After washed with an addition of three times PBS solution, cells were permeabilized with 0.5% Triton X-100 in PBS for 15 minutes. Continuously wash with PBS three times, cells were then block with 5% BSA in PBS for 30 minutes at room temperature and incubated with appropriately diluted primary antibodies (1:300 anti-MATE1) in 1% BSA for 1 hour at room temperature. After three times washed with PBS, the secondary antibody (Goat anti-Rabbit IgG Alexa Fluor 635, Invitrogen A-31576) was diluted in 1% BSA (1:400 anti-rabbit) and added to the cells. Incubations were continued for 1 hour at 37° C. and wash with PBS three times with 5 minutes each wash. In the last step, samples were stored in PBS at 4° C. for further testing.

Compound Synthesis

Synthetic Scheme and Procedure for New Platinum-Acridines

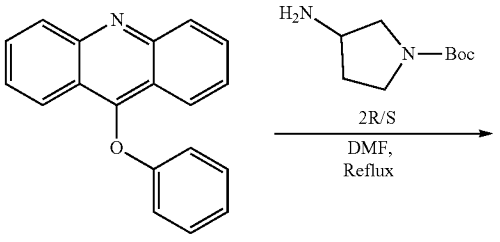

1

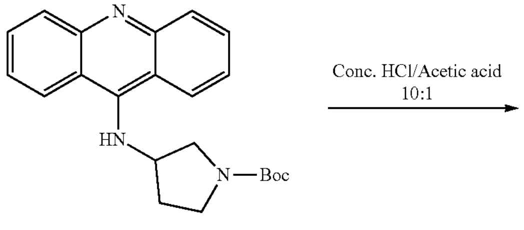

3

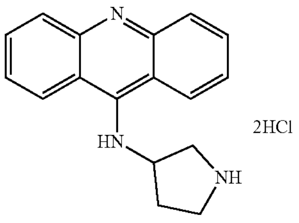

4R/S

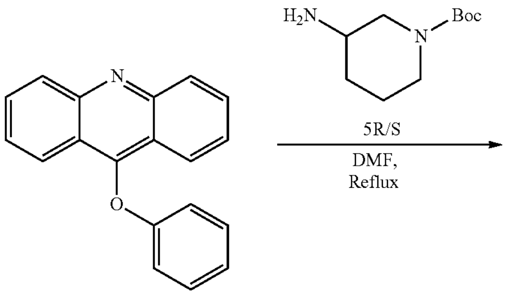

1

-continued

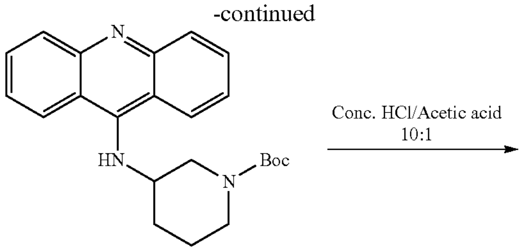

6

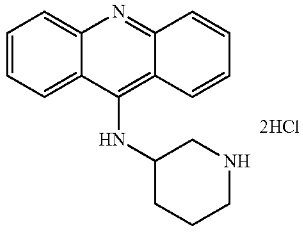

7R/S

Compound 1 (542 mg, 2 mmol, 1eq) was refluxed with the appropriate, enantiomerically pure form (commercially available) of Compound 2R/S (1eq) or 5R/S (1eq) in DMF overnight. DMF was removed under reduced pressure. The crude product was washed by distilled water 3 times and extracted by DCM. DCM was removed to get orange oil. Concentrated HCl and acetic acid mixture (1:10) was added to remove the tert-butyl group to afford the 9-aminoacridines. The mixture was stirred for an hour at room temperature and red oil was collected. Certain amount of ethanol was added to oil and refluxed for 30 minutes. A yellow precipitate formed and recovered by filtration, as dihydrochloride salts Compound 4R/S or 7R/S. Yield: 4R 580 mg, 86.56%; 4S: 586 mg, 87.3%; 7R 654 mg, 93.43%;7S 620 mg, 84.21%

4R (the Enantiomer 4S Gives Identical Spectra, Not Shown)

1H NMR (400 MHz, Deuterium Oxide) δ 8.08 (dd, J=8.8, 1.2 Hz, 2H), 7.87 (ddd, J=8.2, 6.8, 1.1 Hz, 2H), 7.63-7.41 (m, 4H), 5.22 (tt, J=7.4, 5.6 Hz, 1H), 3.78 (dd, J=12.9, 7.5 Hz, 1H), 3.63 (ddd, J=12.1, 8.1, 6.2 Hz, 1H), 3.53 (dd, J=12.9, 5.3 Hz, 1H), 3.45 (dt, J=12.1, 7.7 Hz, 1H), 2.67 (dtd, J=13.9, 7.6, 6.3 Hz, 1H), 2.34 (dtd, J=13.9, 7.9, 5.8 Hz, 1H). 13C NMR (101 MHz, Deuterium Oxide) δ 157.41, 139.00, 135.57, 124.40, 124.30, 118.47, 112.04, 56.88, 49.86, 44.69, 31.54. MS (ESI, positive-ion mode): calculated for C17H18N3 ($[M+H]^+$), 264.15; found: 264.08

7R (the Enantiomer 7S Gives Identical Spectra, Not Shown)

1H NMR (400 MHz, Deuterium Oxide) δ 8.04-7.91 (m, 2H), 7.86 (ddd, J=8.6, 7.1, 1.1 Hz, 2H), 7.60-7.41 (m, 4H), 4.58 (td, J=11.0, 5.4 Hz, 1H), 3.65-3.52 (m, 1H), 3.40 (d, J=12.9 Hz, 1H), 3.18 (dd, J=12.6, 11.2 Hz, 1H), 2.97 (td, J=12.8, 3.4 Hz, 1H), 2.22 (d, J=13.0 Hz, 1H), 2.13-1.98 (m, 1H), 1.91 (qd, J=12.6, 3.4 Hz, 1H), 1.84-1.67 (m, 1H). 13C NMR (101 MHz, Deuterium Oxide) δ 157.77, 138.93, 135.69, 124.59, 124.03, 118.54, 112.34, 52.68, 46.35, 43.33, 29.21, 20.65. MS (ESI, positive-ion mode): calculated for C18H2ON3 ([M+H]+), 278.16; found: 278.12

Procedure for the Preparation of Platinum-Acridine Derivatives:

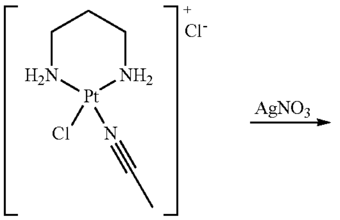

8

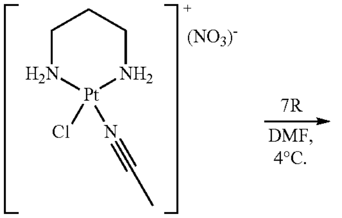

9

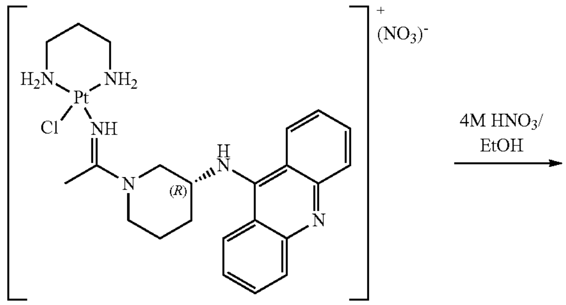

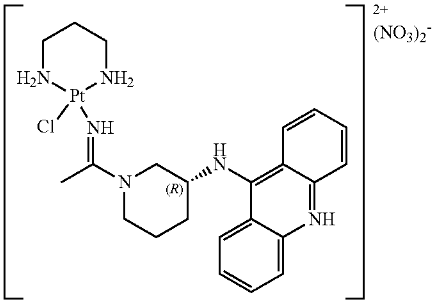

PA-2

Platinum complex 8 (65 mg, 0.17 mmol) was converted to its nitrate salt 9 by reaction with $AgNO_3$ (27 mg, 0.17 mmol)in anhydrous DMF. AgCl was removed by syringe filtration, and the filtrate was cooled to −10° C. Acridine precursor (7R) (47 mg, 0.017 mmol) was added to the solution, and the suspension was stirred at2) 4° C. for 24 h. The reaction mixture was added into vigorously stirred diethyl ether. The yellow precipitate was stirred for approximately 30 min and then recovered by membrane filtration and dried in a vacuum overnight. The solid was dissolved in anhydrous ethanol containing 1 eq. of $HNO_3$ (4M) and stirred at room temperature for 30 min, and the crude dinitrate salt was precipitated with anhydrous diethyl ether. The product PA-2 was further purified by recrystallization from hot ethanol to give dinitrate salt as a yellow microcrystalline solid. Yield: 90 mg, 77.59%

PA-2 and PA-5

$^1$H NMR (400 MHz, DMF-d7) δ 13.97 (s, 1H), 8.73 (d, J=8.7 Hz, 2H), 8.12-7.99 (m, 5H), 7.62 (ddd, J=8.4, 6.4, 1.6 Hz, 2H), 5.68 (d, J=196.9 Hz, 4H), 5.01 (s, 2H), 4.45-4.10 (m, 2H), 4.09-3.59 (m, 3H), 3.50 (s, 4H), 2.91 (s, 3H), 2.88-2.64 (m, 10H), 2.61 (s, 3H), 1.84 (d, J=7.7 Hz, 2H). MS (ESI, positive-ion mode): calculated for $C_{22}H_{31}ClN_6Pt$ ($[M+H]^+$), 609.19; found: 608.14

Synthesis of Acridines Containing Cyclic Amidine Donor Groups

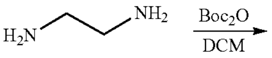

10

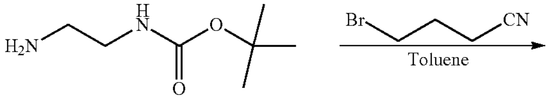

11

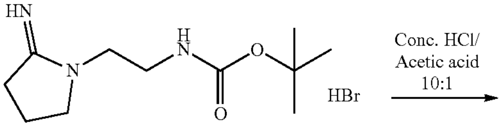

12

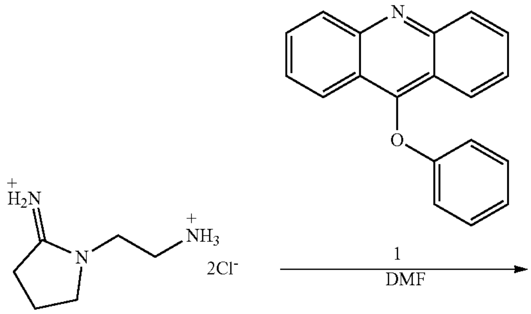

13

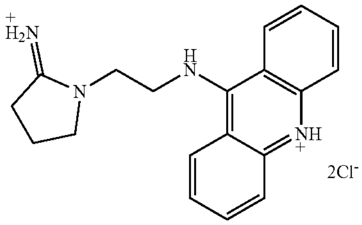

A-24

Ethylenediamine (10) (12 g, 0.2 mol)was reacted with Di-tert-butyl dicarbonate ($Boc_2O$) (4.36 g, 0.02 mol)to get mono-Boc-protected ethylenediamine (11). The ratio between the two reactants was 10:1. $Boc_2O$ was dissolved in DCM and added dropwise into the ethylemediamine solution. Solvent was removed via rotary evaporation after 8 h. Water was added into the residue and formed white precipitate which was removed by vacuum filtration. The filtrate was extracted by DCM three times. The final mono-Boc-protected ethylenediamine (11) was a clear oil. Yield: 2.86 g (89.93%)

4-bromobutanenitrile (2.66 g, 18 mmol) reacted overnight with compound 11 (2.86 g, 18 mmol) in toluene to generate a terminal nitrile. A white precipitate formed, and the rest of the toluene was removed under reduced pressure. The residue was dissolved in DCM and recrystallized in the freezer to produce white crystals of compound 12 as the hydrobromide salt (1.49 g, 4.9 mmol). The protecting group was then removed in acetic acid/concentrated HCl (10:1) or 4 M HCl in dioxane to produce compound 13. Yield: 0.97 g, 27%

9-Phenoxyacridine (1) (1.46 g, 5.39 mmol) was added to compound 13 (0.97 g, 4.9 mmol) in DMF and stirred for 72 hours. An orange precipitate formed, which was filtered off to yield A-24 as the dihydrochloride salt. Yield: 1.84 g (98%).

Compound 12

$^{1}$H NMR (400 MHz, Chloroform-d) δ 9.43 (s, 1H), 9.07 (s, 1H), 6.05 (t, J=6.6 Hz, 1H), 3.81 (q, J=7.6, 6.9 Hz, 4H), 3.53-3.39 (m, 2H), 3.10 (t, J=8.0 Hz, 2H), 2.18 (p, J=7.7 Hz, 2H), 1.43 (s, 9H) $^{13}$C NMR (101 MHz, Chloroform-d) δ 168.83, 156.61, 79.58, 53.47, 46.89, 36.87, 31.80, 28.37, 19.25. MS (ESI, positive-ion mode): calculated for $C_{11}H_{22}N_3O_2$ ($[M+H]^+$), 228.17; found: 228.13

Reaction Scheme for Synthesizing the Corresponding Platinum-Acridine from A-24:

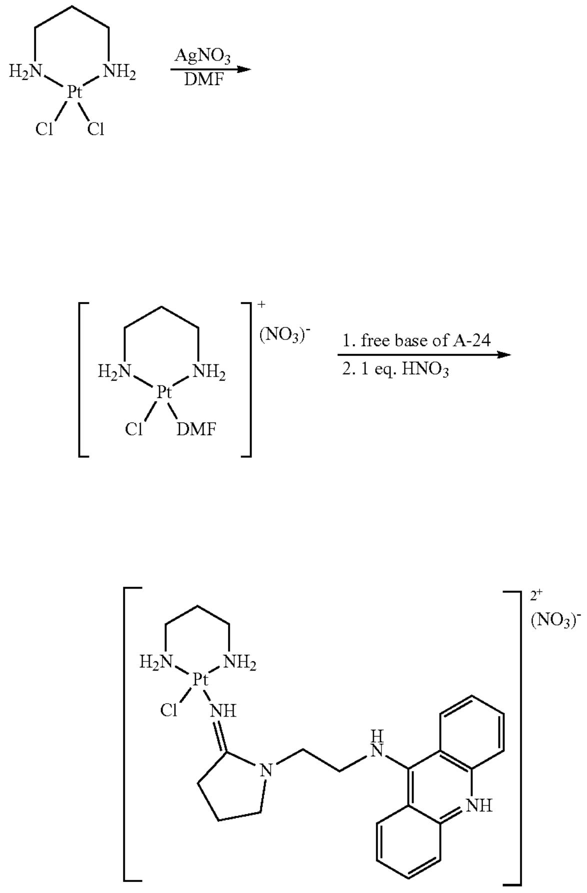

PA-24

The complex $[PtCl_2(pn)]$ is activated with 1 eq. of $AgNO_3$ in DMF, which replaces one chloro ligand with a labile DMF ligand and the precipitated AgCl will be filtered off. What follows is a simple ligand substitution reaction in which DMF is substituted with the amidine donor groups to form the corresponding platinum-acridine. Compound A-24 is converted into its free base with 2 M $NH_3$(aq) and added to the filtrate, and the suspension is stirred at ~60° C. for 3 hrs. in the dark. One equiv. of $HNO_3$ is added to generate the diprotonated form, which is precipitated in diethyl ether and recrystallized from hot ethanol.

Synthesis of Pt(IV) Complexes

Synthesis of PA-21

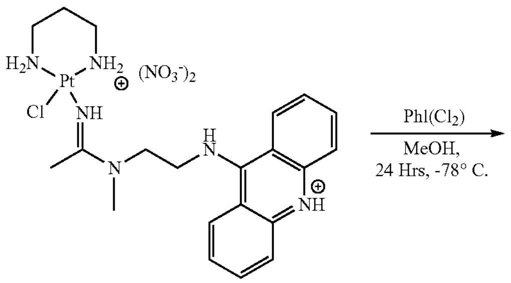

PA-0

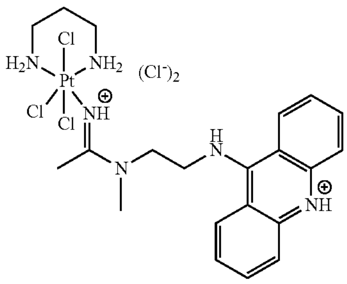

PA-21

PA-0 (50 mg, 69 μmol) was dissolved in dry methanol (750 μL) and was cooled down to −78° C. using a dry ice/acetone bath. Iodobenzene Dichloride (24 mg, 90 μmol) was dissolved in dry methanol (1 mL). The iodobenzene dichloride solution was then added dropwise to the PA-0 solution which was stirred for 24 hours at room temperature. The solution was allowed to warm up to room temperature and was added into vigorously stirred diethyl ether (100 mL) overnight. Yield: 77%

$^{1}$H NMR (400 MHz, Methanol-$d_4$) δ 8.68-8.50 (m, 2H), 8.07-7.97 (m, 2H), 7.89 (dt, J=8.6, 1.7 Hz, 2H), 7.65 (ddd, J=8.5, 6.9, 1.2 Hz, 2H), 4.58-4.46 (m, 2H), 4.29-3.95 (m, 2H), 3.27-2.95 (m, 3H), 2.87-2.56 (m, 5H), 2.53-2.43 (m, 3H), 2.14-1.70 (m, 2H). MS (ESI, positive-ion mode): calculated for $[PtCl_3(pn)C_{18}HN_4]$ ($[M+H]^+$), 667.13; found: 667.06

Synthesis of PA-22

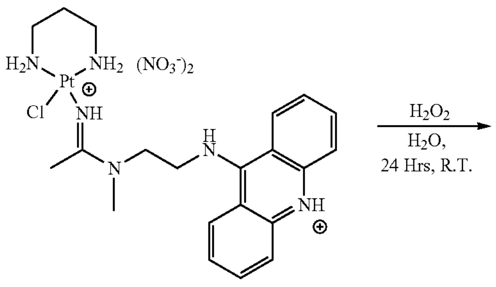

PA-0

-continued

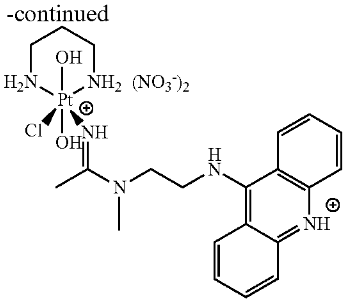

PA-22

Method A: PA-0 (100 mg, 0.132 mmol) is stirred with 100 fold $H_2O_2$ (1.41 mL, 30%) in 17 mL of water at room temperature for 24 hours. Half of the solvent was removed via rotary evaporation, with the remaining solution being added to stirred THF (250 mL). After 5 minutes the solution was allowed to stand at −20° C. for a week. The solution was allowed to warm up to room temperature and the precipitate was filtered and dried in vacuo overnight. Yield: 82%.

Method B: PA-0 (100 mg, 0.132 mmol) was dissolved in 17 mL of water and stirred with 100-fold excess $H_2O_2$ (1.41 mL, 30%) at room temperature for 12 hours. 17 mL of DMF were added to the mixture, and the water was removed via rotary evaporation until only one third of the solution remained The solution was then added dropwise to vigorously stirred diethyl ether (250 mL) and stirred for 16 hours. The precipitate was then filtered and dried in vacuo overnight. Yield: 93%.

$^1$H NMR (400 MHz, Methanol-$d_4$) δ 8.44 (dd, J=8.8, 1.2 Hz, 2H), 7.91 (ddd, J=8.3, 6.9, 1.2 Hz, 2H), 7.77 (dd, J=8.7, 1.2 Hz, 2H), 7.53 (ddd, J=8.4, 6.9, 1.3 Hz, 2H), 4.36 (t, J=6.4 Hz, 2H), 3.98 (t, J=6.7 Hz, 2H), 3.11 (d, J=16.3 Hz, 3H), 2.67-2.44 (m, 4H), 2.39 (s, 3H), 1.97-1.84 (m, 2H). MS (ESI, positive-ion mode): calculated for $[Pt(OH)_2Cl(pn)C_{18}H_{21}N_4]$ ($[M+H]^+$), 631.20; found: 631.16.

Synthesis of PA-23

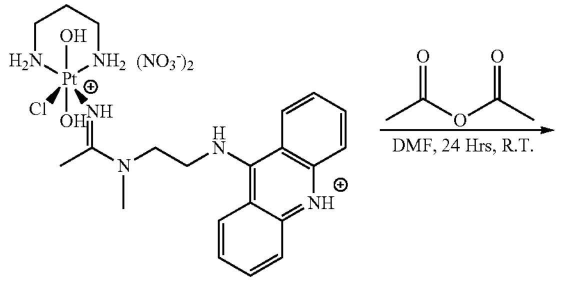

PA-22

-continued

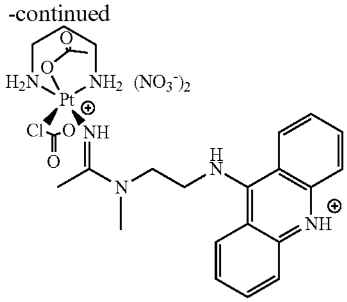

PA-23

Acetic anhydride (4.5 mL, 48 mmol) was mixed with PA-22 (360 mg, 0.476 mmol) in limited amount of dry DMF for 24 hours. The solution was then added dropwise to vigorously stirred diethyl ether (250 mL) and stirred overnight. The precipitate was filtered and dried in vacuo overnight. Yield: 85%.

$^1$H NMR (400 MHz, DMF-$d_7$) δ 13.98 (s, 1H), 9.95 (s, 1H), 8.70 (d, J=8.7 Hz, 2H), 8.31-8.13 (m, 1H), 8.12-7.99 (m, 6H), 7.78 (d, J=36.9 Hz, 4H), 7.68-7.57 (m, 2H), 4.60 (s, 2H), 4.29 (t, J=6.7 Hz, 2H), 3.43 (s, 1H), 3.28 (s, 2H), 2.96 (s, 2H), 2.79 (d, J=0.6 Hz, 2H), 2.67 (s, 4H), 2.42 (d, J=30.0 Hz, 3H), 2.13 (s, 2H), 2.02 (s, 4H), 1.90 (s, 2H). $^{13}$C NMR (101 MHz, DMF-d7) δ 180.71, 168.30, 160.18, 141.72, 136.81, 127.35, 125.42, 120.54, 114.60, 53.27, 49.04, 42.61, 40.82, 37.63, 27.57, 23.94, 18.55. MS (ESI, positive-ion mode): calculated for $[Pt(OCOCH_3)_2Cl(pn)C_{18}H_{21}N_4]$ ($[M+H]^+$), 715.22; found: 715.16.

While the compounds and methods have been described with an emphasis upon preferred or exemplified embodiments, it will be obvious to those of ordinary skill in the art that variations in the disclosed compounds and methods can be used and that it is intended that the invention can be practiced otherwise than as specifically described herein. Accordingly, this invention includes all modifications encompassed within the spirit and scope of the invention as defined by the claims that follow.

The invention claimed is:

1. A compound represented by Formula I,

Formula I

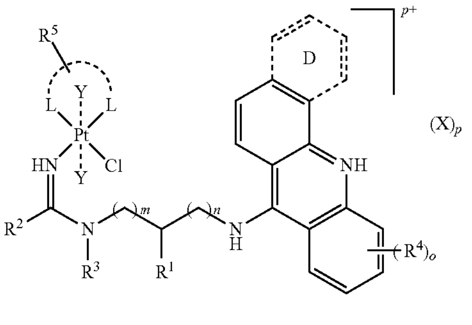

wherein, wherein the two Ls link up to form a diamine ligand (chelate) selected from the group consisting of

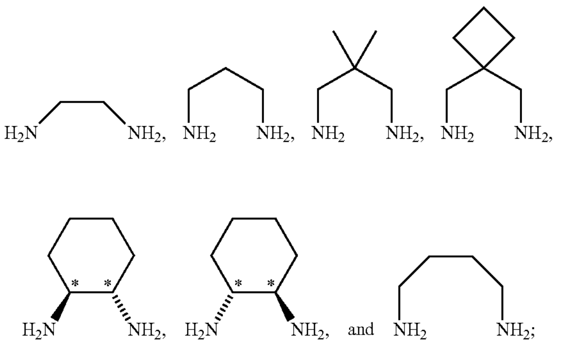

X represents nitrate or halide;

Each Y is optional and independently represents a ligand selected from the group consisting of halide, hydroxide, pseudohalide, acetate, and

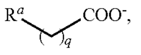

wherein q is an integer from 1 to 6 inclusive, wherein $R^a$ represents (a) $C_{1-4}$alkyl, OH, SH, $NH_2$, COOH, CN, an alkyne-containing group, or $N_3$; or (b) $L_x$-E, wherein E is a terminal electrophilic group selected from the group consisting maleimide-based moiety, 2'-pyridyldithio variant, aromatic or vinyl sulfone, acrylate, haloacetyl, and N-hydroxysuccinimidyl ester;

wherein $L_x$ in (b) is a linker comprising:

(1) a linkage formed from azide and alkyne; and (2) one or more components selected from the group consisting of $—(CH_2)_aC(O)NR^x—$, $—C(O)NR^x—$, $—(CH_2)_aC(O)NR^x(CH_2)_b—$, $—(CH_2)_a—$, $—(CH_2)_aO(CH_2CH_2O)_c—$, $—(CH_2)_a$heterocyclyl-, $—(CH_2)_aC(O)—$, $—(CH_2)_a NR^x—$, $—CR^x{=}N—NR_x—$, $—CR^x{=}N—O—$, $—CR^x{=}N—NR^y—CO—$, $—N{=}N—CO—$, and $—S—S—$, wherein a, b, and c are each an integer selected from 0 to 25, all subunits included, and $R^x$ and $R^y$ independently represent hydrogen or C1-C10 alkyl;

o is 0, 1, 2 or 3 p is 1 or 2;

m is 0, 1, 2 or 3;

n is 0, 1, 2 or 3;

D is an optional 6-membered aromatic ring;

$R^1$ represents H or a $C_{1-10}$ alkyl;

$R^2$ and $R^3$ each independently represents a $C_{1-10}$ alkyl, wherein one or more carbons of the $C_{1-10}$ alkyl is optionally substituted with a moiety selected from the group consisting of hydroxy and $C_{1-10}$ alkoxy;

Each $R^4$ is selected from the group consisting of halogen, cyano, $C_{1-10}$ alkoxy, dialkylamino, $C_{1-10}$ alkyl, and (mono-, di-, or trihalogeno)methyl;

$R^5$ represents an optional substituent of L and is selected from the group consisting of $C_{1-10}$ alkoxy, $C_{1-10}$ dialkylamino, $C_{1-10}$ alkyl, and (mono-, di-, or trihalogeno) methyl;

provided that the compound meets one of (i), (ii), (iii), and (iv):

(i) $R^1$ and $R^3$ link up to form a 4 to 8 membered ring;

(ii) $R^2$ and $R^3$ link up to form a 5 to 8 membered ring;

(iii) two Ys are present and are each independently selected from the group consisting of OH, acetate and

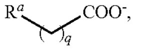

wherein q is an integer from 1 to 6 inclusive, $R^a$ represents $C_{1-4}$ alkyl, OH, SH, $NH_2$, COOH, an alkyne-containing group, or $N_3$; and (iv) two Ys are present and one of the two Ys is

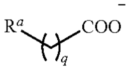

wherein $R^a$ is $L_x$-E;

wherein a dotted line is an optional bond.

2. The compound of claim 1, wherein $R^1$ and $R^3$ link up to form a 4 to 8 membered ring as represented by Formula II Formula II

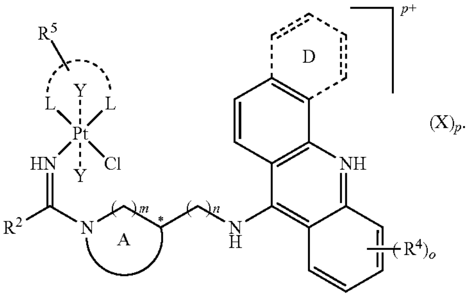

3. The compound of claim 2, wherein m is 1 and n is 0, wherein D is void and $R^5$ represents the optional substituent of L and is $C_{1-10}$ alkoxy or $C_{1-10}$ alkyl.

4. The compound of claim 3, wherein ring A is a 5 or 6-membered ring and o is 0, both Ys are presents.

5. The compound of claim 3, wherein o is 0, both Ys are void, ring A is

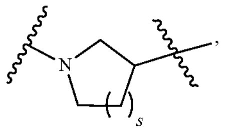

wherein s is 1 or 2.

6. The compound of claim 2, wherein the carbon with asterisk has an R configuration.

7. The compound of claim 2, wherein the carbon with asterisk has an S configuration.

8. The compound of claim 1, which is selected from the group consisting of

PA-1

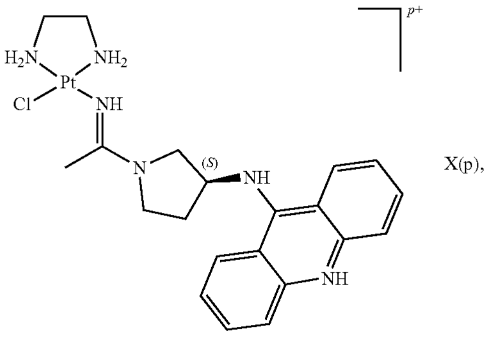

-continued
PA-2
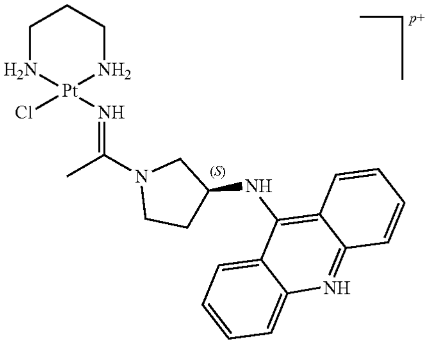
X(p),
PA-3
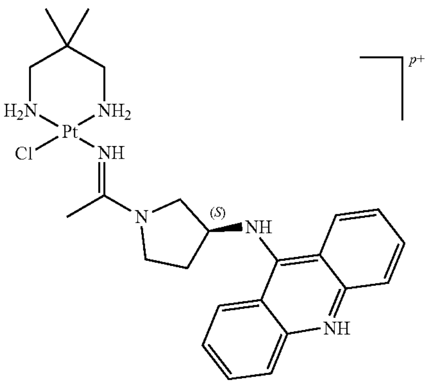
X(p),
PA-4
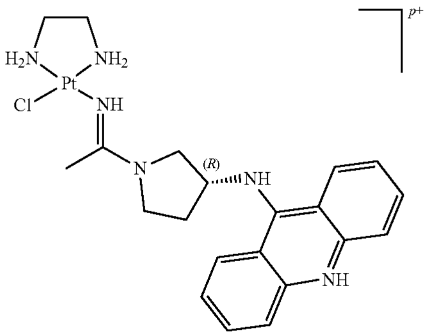
X(p),
PA-5
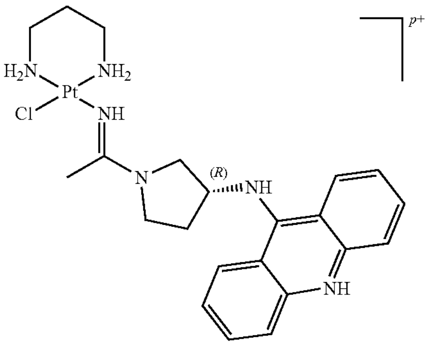
X(p),
-continued
PA-6
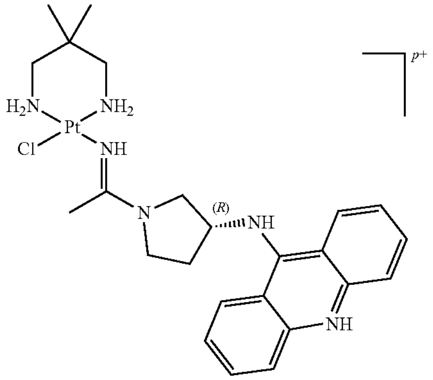
X(p),
PA-7
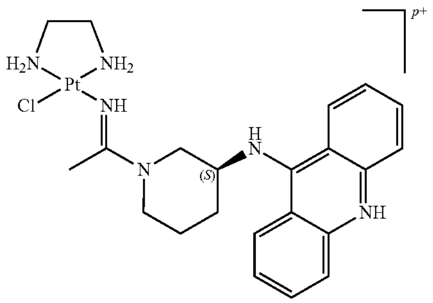
X(p),
PA-8
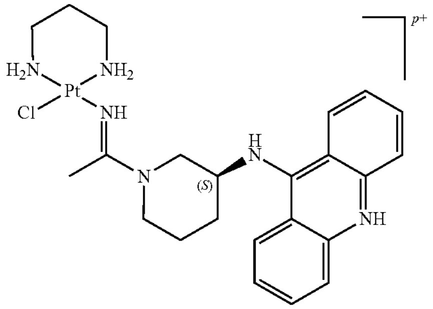
X(p),
PA-9
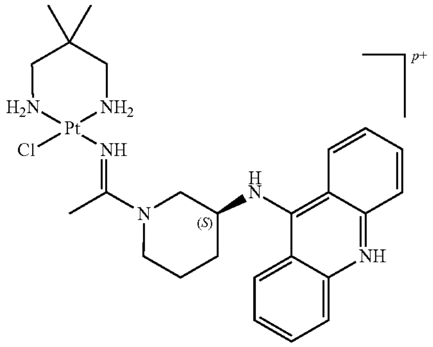
X(p), -continued
PA-10
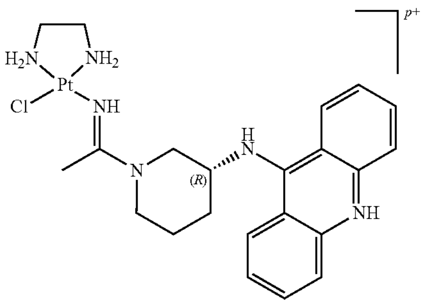
X(p),
PA-11
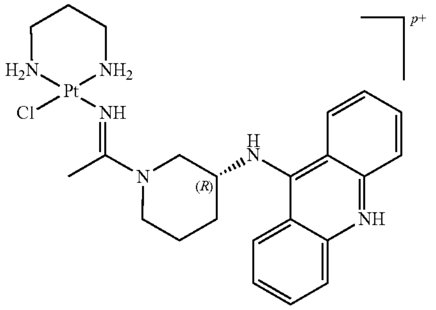
X(p),
PA-12
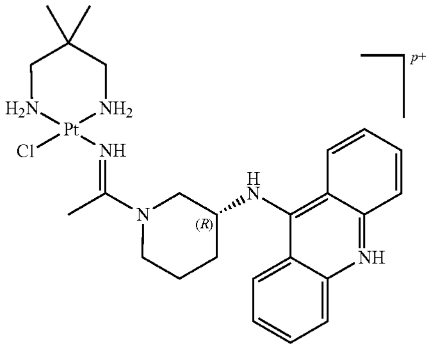
X(p),
PA-13
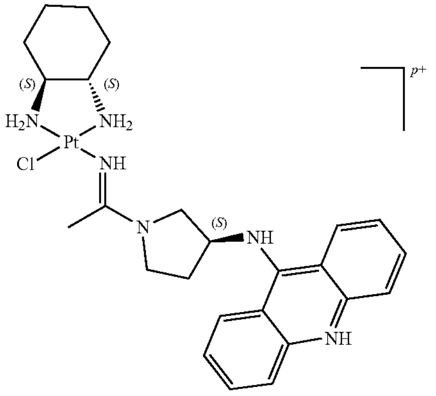
X(p),
-continued
PA-14
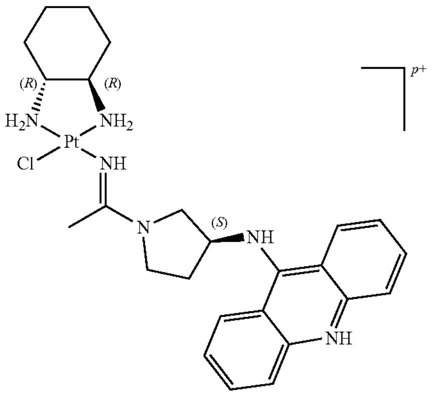
X(p),
PA-15
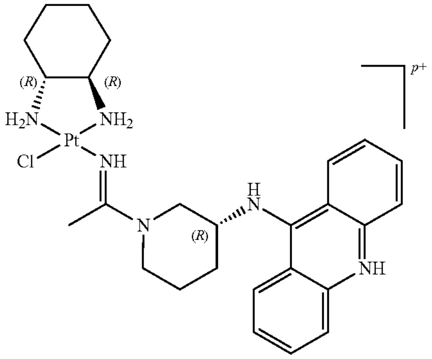
X(p),
PA-16
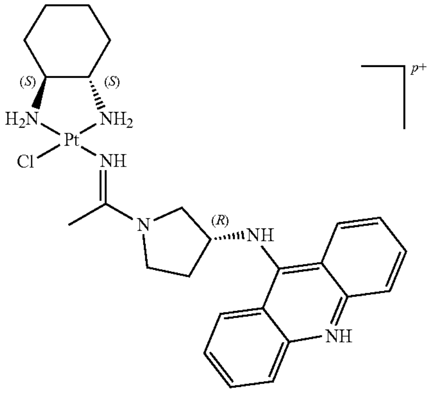
X(p),
PA-17
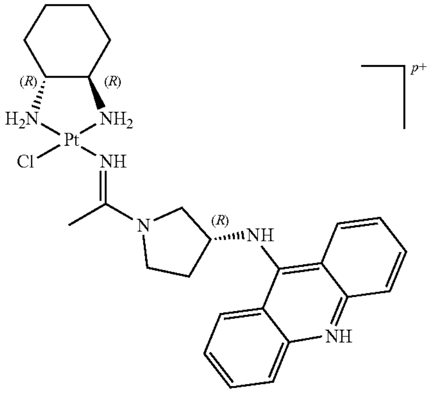
X(p), -continued

PA-18

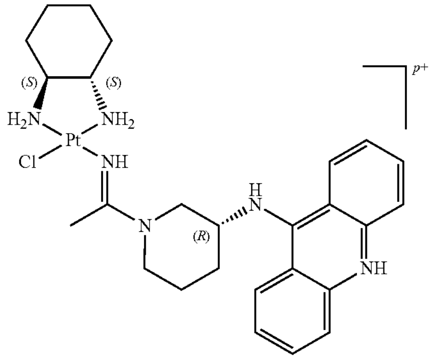

X(p),

PA-19

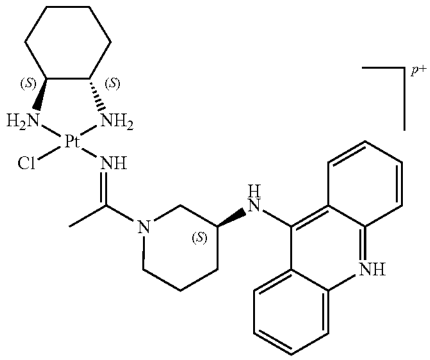

X(p), and

PA-20

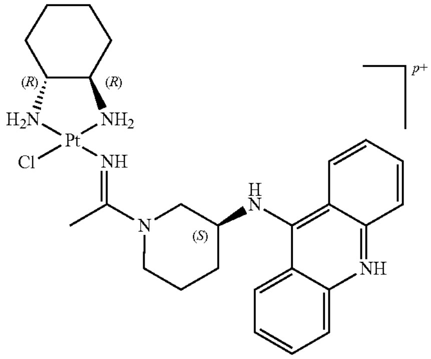

X(p).

9. The compound of claim 1, wherein p is 2 and X is nitrate.

10. The compound of claim 1, wherein $R^2$ and $R^3$ link up to form a 5 to 8 membered ring and the compound is represented by Formula III Formula III

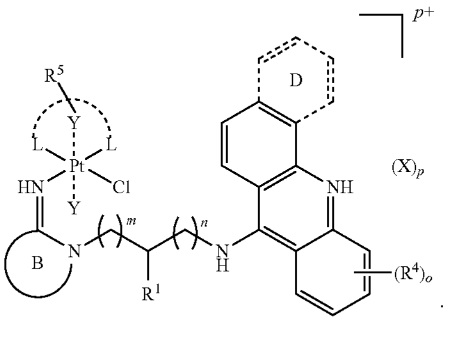

11. The compound of claim 10, wherein ring B is a 5 or 6-membered ring and both Ys are presents, wherein o is 0, m is 1 and n is 0, wherein D is void and $R^5$ represents the optional substituent of L and is $C_{1-10}$ alkoxy or $C_{1-10}$ alkyl.

12. The compound of claim 10, wherein both Ys are void and ring B is

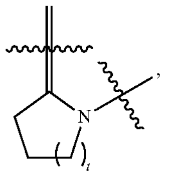

wherein t is 1 or 2, o is 0, m is 1 and n is 0, wherein D is void and $R^5$ represents the optional substituent of L and is $C_{1-10}$ alkoxy or $C_{1-10}$ alkyl.

13. The compound of claim 1, wherein two Ys are present and one of the two Ys is

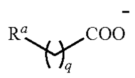

wherein $R^a$ is $L_x$-E, wherein E is maleimido-based moiety or N-hydroxysuccinimidyl ester.

14. The compound of claim 13, wherein the alkyne for forming the linkage is selected from the group consisting of dibenzocyclooctyne (DBCO), bicyclooctanonyne (BCN), and difluorocyclooctyne (DIFO).

15. The compound of claim 13, wherein the linker $L_x$ further comprises $(CH_2)_xO(CH_2CH_2O)_y$, wherein x is an integer selected from 0 to 25 and y is an integer selected from 1 to 25.

16. The compound of claim 13, which is
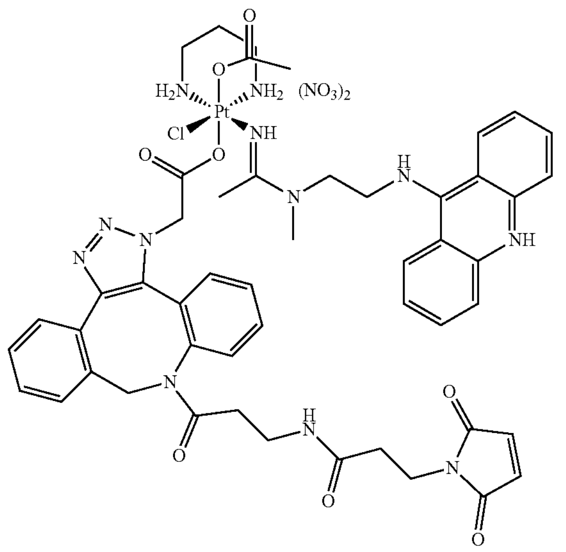
,
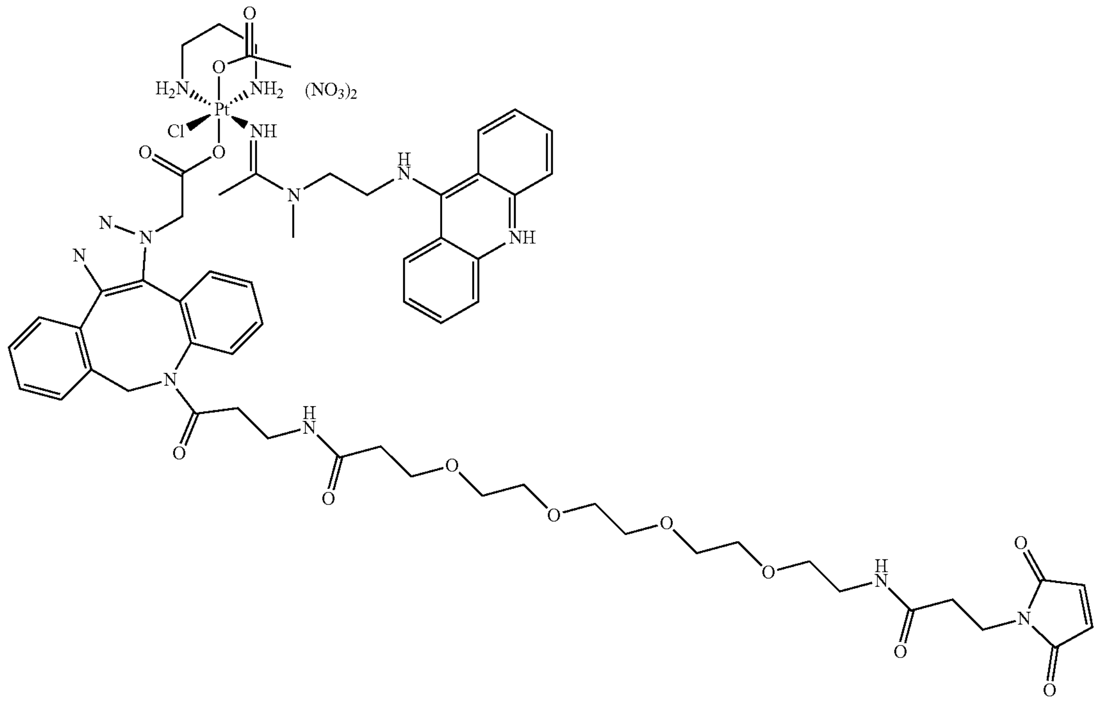
,

-continued
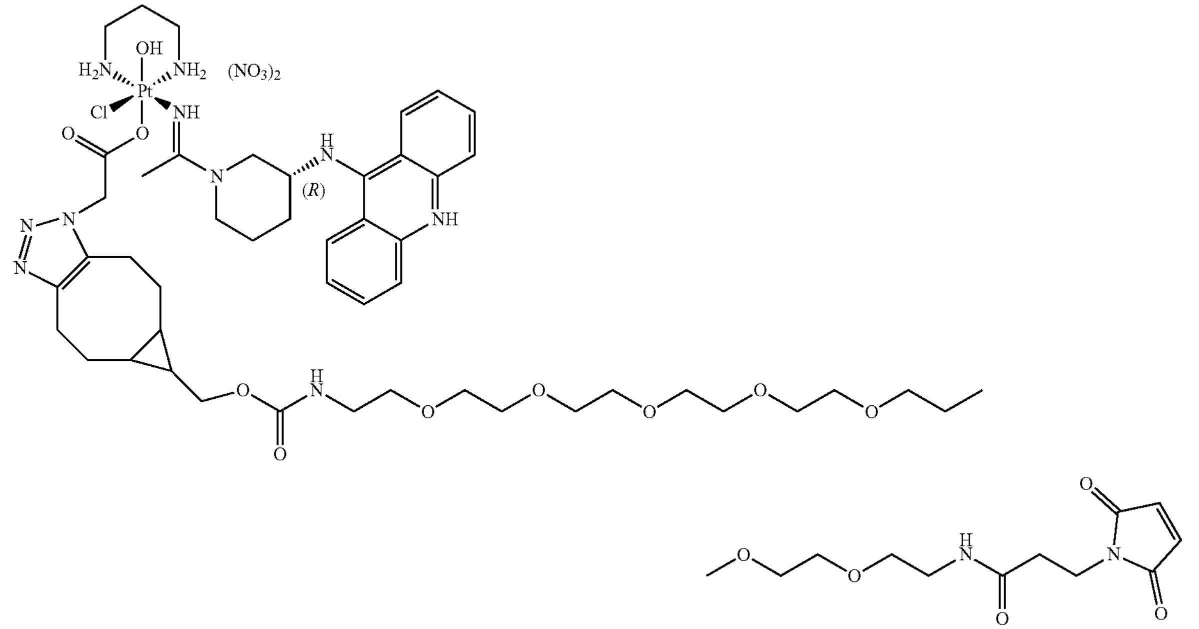
,
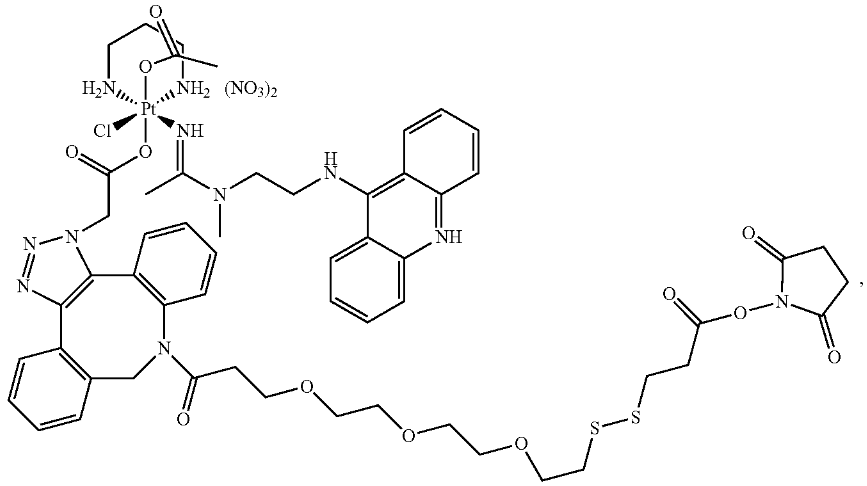
, or
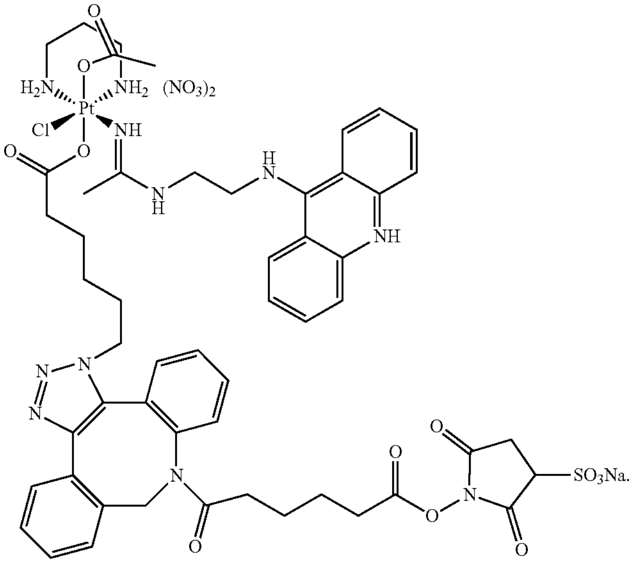

17. A pharmaceutical composition comprising the compound of claim 1, and at least one pharmaceutically acceptable carrier.

18. A method of treating non-small cell lung cancer in a subject, comprising administering to the subject a therapeutically effective amount of the compound of claim 1, wherein:

(i) $R^1$ and $R^3$ link up to form a 4 to 8 membered ring; or (ii) $R^2$ and $R^3$ link up to form a 5 to 8 membered ring.

19. The method of claim 18, further comprising, prior to administering the compound, determining expression of MATE1 in tissues of the cancer.

20. The compound of claim 1, wherein one of the two Ys is OH, and the other is

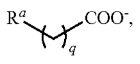

wherein q is 1, and $R^a$ represents $N_3$.

21. The compound of claim 20, wherein ring D is void, and o is 0.

22. The compound of claim 1, wherein one of the Ys is

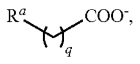

and $R^a$ is $L_x$-E.

23. The compound of claim 1, wherein one of the Ys is

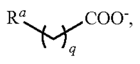

$R^a$ is $L_x$-E, and the one or more components of $L_x$ are selected from the group consisting of $—(CH_2)_a—$, $—(CH_2)_aO(CH_2CH_2O)_c—$, $—(CH_2)_aC(O)—$, and —S—S—.

24. The compound of claim 1, which is selected from the group consisting of

PA-22

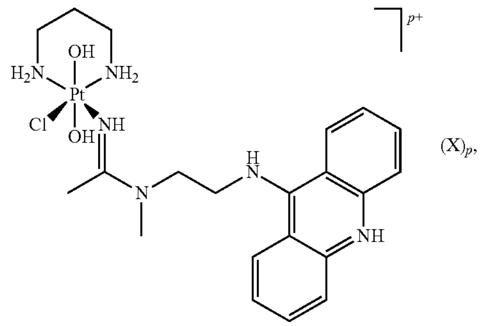

PA-23

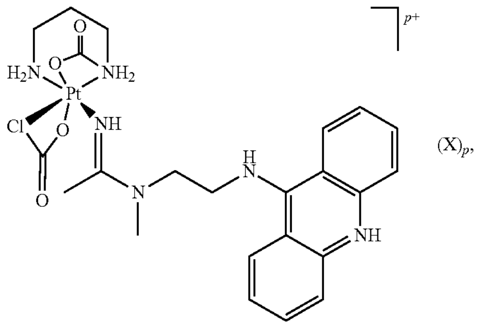

and

PA-24

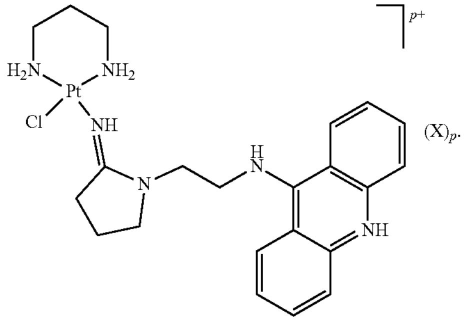

25. The pharmaceutical composition of claim 17, wherein:

(i) $R^1$ and $R^3$ link up to form a 4 to 8 membered ring; or (ii) $R^2$ and $R^3$ link up to form a 5 to 8 membered ring.

* * * * *

SEQUENCE LISTING

<160> NUMBER OF SEQ ID NOS: 8

<210> SEQ ID NO 1
<211> LENGTH: 571
<212> TYPE: PRT
<213> ORGANISM: Homo sapiens

<400> SEQUENCE: 1

-continued

```
Met Glu Ala Pro Glu Glu Pro Ala Pro Val Arg Gly Gly Pro Glu Ala
1               5                   10                  15

Thr Leu Glu Val Arg Gly Ser Arg Cys Leu Arg Leu Ser Ala Phe Arg
            20                  25                  30

Glu Glu Leu Arg Ala Leu Leu Val Leu Ala Gly Pro Ala Phe Leu Val
        35                  40                  45

Gln Leu Met Val Phe Leu Ile Ser Phe Ile Ser Ser Val Phe Cys Gly
    50                  55                  60

His Leu Gly Lys Leu Glu Leu Asp Ala Val Thr Leu Ala Ile Ala Val
65                  70                  75                  80

Ile Asn Val Thr Gly Val Ser Val Gly Phe Gly Leu Ser Ser Ala Cys
                85                  90                  95

Asp Thr Leu Ile Ser Gln Thr Tyr Gly Ser Gln Asn Leu Lys His Val
            100                 105                 110

Gly Val Ile Leu Gln Arg Ser Ala Leu Val Leu Leu Leu Cys Cys Phe
        115                 120                 125

Pro Cys Trp Ala Leu Phe Leu Asn Thr Gln His Ile Leu Leu Leu Phe
    130                 135                 140

Arg Gln Asp Pro Asp Val Ser Arg Leu Thr Gln Thr Tyr Val Thr Ile
145                 150                 155                 160

Phe Ile Pro Ala Leu Pro Ala Thr Phe Leu Tyr Met Leu Gln Val Lys
                165                 170                 175

Tyr Leu Leu Asn Gln Gly Ile Val Leu Pro Gln Ile Val Thr Gly Val
            180                 185                 190

Ala Ala Asn Leu Val Asn Ala Leu Ala Asn Tyr Leu Phe Leu His Gln
        195                 200                 205

Leu His Leu Gly Val Ile Gly Ser Ala Leu Ala Asn Leu Ile Ser Gln
    210                 215                 220

Tyr Thr Leu Ala Leu Leu Leu Phe Leu Tyr Ile Leu Gly Lys Lys Leu
225                 230                 235                 240

His Gln Ala Thr Trp Gly Gly Trp Ser Leu Glu Cys Leu Gln Asp Trp
                245                 250                 255

Ala Ser Phe Leu Arg Leu Ala Ile Pro Ser Met Leu Met Leu Cys Met
            260                 265                 270

Glu Trp Trp Ala Tyr Glu Val Gly Ser Phe Leu Ser Gly Ile Leu Gly
        275                 280                 285

Met Val Glu Leu Gly Ala Gln Ser Ile Val Tyr Glu Leu Ala Ile Ile
    290                 295                 300

Val Tyr Met Val Pro Ala Gly Phe Ser Val Ala Ala Ser Val Arg Val
305                 310                 315                 320

Gly Asn Ala Leu Gly Ala Gly Asp Met Glu Gln Ala Arg Lys Ser Ser
                325                 330                 335

Thr Val Ser Leu Leu Ile Thr Val Leu Phe Ala Val Ala Phe Ser Val
            340                 345                 350

Leu Leu Leu Ser Cys Lys Asp His Val Gly Tyr Ile Phe Thr Thr Asp
        355                 360                 365

Arg Asp Ile Ile Asn Leu Val Ala Gln Val Val Pro Ile Tyr Ala Val
    370                 375                 380

Ser His Leu Phe Glu Ala Leu Ala Cys Thr Ser Gly Gly Val Leu Arg
385                 390                 395                 400

Gly Ser Gly Asn Gln Lys Val Gly Ala Ile Val Asn Thr Ile Gly Tyr
                405                 410                 415

Tyr Val Val Gly Leu Pro Ile Gly Ile Ala Leu Met Phe Ala Thr Thr
```

```
            420                 425                 430

Leu Gly Val Met Gly Leu Trp Ser Gly Ile Ile Ile Cys Thr Val Phe
        435                 440                 445

Gln Ala Val Cys Phe Leu Gly Phe Ile Ile Gln Leu Asn Trp Lys Lys
    450                 455                 460

Ala Cys Gln Gln Ala Gln Val His Ala Asn Leu Lys Val Asn Asn Val
465                 470                 475                 480

Pro Arg Ser Gly Asn Ser Ala Leu Pro Gln Asp Pro Leu His Pro Gly
                485                 490                 495

Cys Pro Glu Asn Leu Glu Gly Ile Leu Thr Asn Asp Val Gly Lys Thr
            500                 505                 510

Gly Glu Pro Gln Ser Asp Gln Gln Met Arg Gln Glu Glu Pro Leu Pro
        515                 520                 525

Glu His Pro Gln Asp Gly Ala Lys Leu Ser Arg Lys Gln Leu Val Leu
    530                 535                 540

Arg Arg Gly Leu Leu Leu Leu Gly Val Phe Leu Ile Leu Leu Val Gly
545                 550                 555                 560

Ile Leu Val Arg Phe Tyr Val Arg Ile Gln Phe
                565                 570


<210> SEQ ID NO 2
<211> LENGTH: 3280
<212> TYPE: RNA
<213> ORGANISM: Homo sapiens

<400> SEQUENCE: 2

acugccggcc ugcgcgguac ucacugccgg ccuccgcggu acccacugcc ggccuccgcg      60

cuacccggcc gcagcgcgcg agucacaugg aagcuccuga ggagcccgcg ccagugcgcg     120

gaggcccgga ggccacccuu gagguccgug ggucgcgcug cuugcggcug uccgccuucc     180

gagaagagcu gcgggcgcuc uugguccugg cuggccccgc guucuugguu cagcugaugg     240

uguuccugau cagcuucaua agcuccgugu ucuguggcca ccugggcaag cuggagcugg     300

augcagucac gcuggcaauc gcgguuauca augucacugg ugucucagug ggauucggcu     360

uaucuucugc cugugacacc cucaucuccc agacguacgg gagccagaac cugaagcacg     420

ugggcgugau ccugcagcgg agugcgcucg uccugcuccu cugcugcuuc cccugcuggg     480

cgcucuuucu caacacccag cacauccugc ugcucuucag gcaggaccca gaugugucca     540

ggcuuaccca gaccuauguc acgaucuuca uuccagcucu uccugcaacc uuucuuuaua     600

uguuacaagu uaaauauuug cucaaccagg gaauuguacu gccccagauc guaacuggag     660

uugcagccaa ccuugucaau gcccucgcca acuaucuguu ucuccaucaa cugcaucuug     720

gggugauagg cucugcacug gcaaacuuga uuucccagua cacccuggcu cuacuccucu     780

uucucuacau ccucgggaaa aaacugcauc aagcuacaug gggaggcugg ucccucgagu     840

gccugcagga cugggccucc uuccuccgcc uggccauccc cagcaugcuc augcugugca     900

uggaguggug ggccuaugag gucgggagcu ucccucagugg cauccucggc augguggagc     960

ugggcgcuca guccaucgug uaugaacugg ccaucauugu guacaugguc ccugcaggcu    1020

ucagugugge ugccagugue cggguaggaa acgcucuggg ugcuggagac auggagcagg    1080

cacggaaguc cucuaccguu ucccugcuga uuacagugcu cuuugcugua gccuucagug    1140

uccugcuguu aagcuguaag gaucacgugg gguacauuuu uacuaccgac cgagacauca    1200

uuaaucuggu ggcucaggug guuccaauuu augcuguuuc ccaccucuuu gaagcucuug    1260
```

-continued cuugcacgag ugguggugau cugaggggga guggaaauca gaagguugga gccauuguga 1320
auaccauugg guacuaugug guuggccucc ccaucgggau cgcgcugaug uuugcaacca 1380
cacuuggagu gaugggucug uggucaggga ucaucaucug uacagucuuu caagcugugu 1440
guuuucuagg cuuuauuauu cagcuaaauu ggaaaaaagc cugucagcag gcucagguac 1500
acgccaauuu gaaaguaaac aacgugccuc ggagugggaa uucugcucuc ccucaggauc 1560
cgcuucaccc agggugcccu gaaaaccuug aaggaauuuu aacgaacgau guuggaaaga 1620
caggcgagcc ucagucagau cagcagaugc gccaagaaga accuuugccg gaacauccac 1680
aggacggcgc uaaauugucc aggaaacagc uggugcugcg gcgagggcuu cugcuccugg 1740
gggucuucuu aaucuugcug guggggauuu uagugagauu cuaugucaga auucagugac 1800
gugguaggaa agaaagucag gucaagugau gcuuuugagc uuacacacaa uucacaggcc 1860
caccagugac aauuuacugu gaguuaaugu cauucaggug ugcccaugga uuuugagggc 1920
uggaaaugca aagacacauu uuucuauaaa aagaaaaagc aacuaagguu aaaagcuaua 1980
uuguggccca agacacuguc ugaaagauga caugaguagu aauucaccac uaucugaacc 2040
aagcaaggau caaugugcug acugcauugg ccaauggcuu ugauacuucu gcuauuuuuu 2100
uagacacaaa cccauaaacu aacugcuuaa gaauucauac ugcuugaauu auguaaaaua 2160
uauuuuacag uauaucuuuc cuugggccuu agauuacuau ucacugggca aaugguauuu 2220
guuuuuguuu uaauuuuuuu uuuaauagac ggaagucuug cucugucaug caggcuggag 2280
ugcgguggug cgaucauagc ucacugcagc cucgaacucu ugggcuucaa gcaauccucc 2340
ugugucagcc accagaguag cugagacuac aggguaugc caccaugccc agcuggcauu 2400
uguuaaucuu cauuugaggu cuagaucuag gcacugugga cacugaaaaa caguugggaa 2460
aucuuucgag cuguggaaau ccaaacaaag acugauaauu ccugguaggg gugugugcgu 2520
gacguacugc agccucaacc uccugggcuc aagugauccu cccaccucag ccuccugagu 2580
agcugagacc acaggcgugu gccaccacgc cuagcuaauu uuuuauacca gggucuaccc 2640
uuuguuuccc aggcuggucu ugaauuccug ggaucaagca auccuuccac cuugccccucc 2700 caaaguguug ggauuauagg caugagccac cacgacuggc cagaggacaa aauuuuaaua 2760
aaggucuuag cuuaagcagu aauccuacuu cauuaagccu uccuggggug cgguacacac 2820
cguuaauuca gcaacccuca guacauacua aguaugcuca gugcugugaa aguggauuac 2880
accaaauuaa gucauucuua ucacacccaa ucaaaaguca agaagccagg gauaaaagca 2940
ccucaggcac auaacauuaa ucuaguaaug uaauucucug cacauccagc uggugaaacu 3000
gcgugcugua agcugggacc agcuuugucc auaacugcug agagaacuug cugaagcucu 3060
aggaauaauu uugccugccc gguugcucac caguuguagc uugccagcuc ccaacacccu 3120
uccuggugcc aauaaacuuu cucaaagagc aauacugaca uuucuuuuga uaaaaccucc 3180
agccuucucu guguuguucc gacauaccga ggaccaacug gucuacaugg augcccugaa 3240
caugcaauuc uuucuuccaa aauaaaacau uaaauagaga 3280

<210> SEQ ID NO 3
<211> LENGTH: 21
<212> TYPE: DNA
<213> ORGANISM: Homo sapiens

<400> SEQUENCE: 3
ccgagacauc auuaaucugt t 21

-continued

<210> SEQ ID NO 4
<211> LENGTH: 21
<212> TYPE: DNA
<213> ORGANISM: Homo sapiens

<400> SEQUENCE: 4
cagauuaaug augucucggt c 21

<210> SEQ ID NO 5
<211> LENGTH: 21
<212> TYPE: DNA
<213> ORGANISM: Homo sapiens

<400> SEQUENCE: 5
caaacuugau uucccaguat t 21

<210> SEQ ID NO 6
<211> LENGTH: 21
<212> TYPE: DNA
<213> ORGANISM: Homo sapiens

<400> SEQUENCE: 6
uacugggaaa ucaaguuugc c 21

<210> SEQ ID NO 7
<211> LENGTH: 21
<212> TYPE: DNA
<213> ORGANISM: Homo sapiens

<400> SEQUENCE: 7
gaucguaacu ggaguugcat t 21

<210> SEQ ID NO 8
<211> LENGTH: 21
<212> TYPE: DNA
<213> ORGANISM: Homo sapiens

<400> SEQUENCE: 8
ugcaacucca guuacgauct g 21